(12) United States Patent
Pluskal et al.

(10) Patent No.: US 11,739,354 B2
(45) Date of Patent: Aug. 29, 2023

(54) ENZYMATIC SYNTHESIS OF KAVALACTONES AND FLAVOKAVAINS

(71) Applicant: Whitehead Institute for Biomedical Research, Cambridge, MA (US)

(72) Inventors: Tomás Pluskal, Boston, MA (US); Jing-Ke Weng, Belmont, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 77 days.

(21) Appl. No.: 17/190,872

(22) Filed: Mar. 3, 2021

(65) Prior Publication Data
US 2022/0002768 A1 Jan. 6, 2022

Related U.S. Application Data

(62) Division of application No. 16/249,758, filed on Jan. 16, 2019, now Pat. No. 10,941,429.

(60) Provisional application No. 62/618,549, filed on Jan. 17, 2018.

(51) Int. Cl.
*C12P 17/06* (2006.01)
*C12P 7/26* (2006.01)

(52) U.S. Cl.
CPC ............... *C12P 17/06* (2013.01); *C12P 7/26* (2013.01); *C12Y 301/27005* (2013.01)

(58) Field of Classification Search
CPC . A61K 31/525; C12N 1/14; C12P 1/04; C12P 17/06; C12P 7/26; C12Y 301/27005
USPC ........................................................ 435/130
See application file for complete search history.

(56) References Cited

U.S. PATENT DOCUMENTS 10,941,429 B2    3/2021   Pluskal et al.

OTHER PUBLICATIONS

Abu et al., The flavokawains: uprising medicinal chaicones. Cancer Cell Int. Oct. 22, 2013;13(1):102. doi: 10.1186/1475-2867-13-102.
Cairney et al., The neurobehavioural effects of kava. Aust N Z J Psychiatry. Oct. 2002;36(5):657-62.
Chua et al., Kavain, the Major Constituent of the Anxiolytic Kava Extract, Potentiates GABAA Receptors: Functional Characteristics and Molecular Mechanism. PLoS One. Jun. 22, 2016;11(6):e0157700. doi: 10.1371/journal.pone.0157700.
Devos et al., Practical limits of function prediction. Proteins. Oct. 1, 2000;41(1):98-107.
Dinh et al., Interaction of various Piper methysticum cultivars with CNS receptors in vitro. Planta Med. Jun. 2001;67(4):306-11.
Kisselev, Polypeptide release factors in prokaryotes and eukaryotes: same function, different structure. Structure. Jan. 2002;10(1):8-9. doi: 10.1016/s0969-2126(01)00703-1.
Lebot et al., The Origin and Distribution of Kava (Piper Methysticum Forst. F., Piperaceae): A Phytochemical Approach. Allertonia. Sep. 1989;5(2):223-81.
Ligresti et al., Kavalactones and the endocannabinoid system: the plant-derived yangonin is a novel CB? receptor ligand. Pharmacol Res. Aug. 2012;66(2):163-9. doi: 10.1016/j.phrs.2012.04.003. Epub Apr. 14, 2012.
Marti-Renom et al., Comparative protein structure modeling of genes and genomes. Annu. Rev. Biophys. Biomol. Struct. 2000;29:291-325.
Pluskal et al., The biosynthetic origin of psychoactive kavalactones in kava. bioRxiv: The Preprint server for Biology. https://doi.org/10.1101/294439. Epub Apr. 4, 2018. 34 pages.
Pluskal et al., The biosynthetic origin of psychoactive kavalactones in kava. Nature Plants. Jul. 22, 2019;5:867-78. doi:10.1038/s41477-019-0474-0.
Sarris et al., Kava: a comprehensive review of efficacy, safety, and psychopharmacology. Aust N Z J Psychiatry. Jan. 2011;45(1):27-35. doi: 10.3109/00048674.2010.522554. Epub Nov. 15, 2010.
Shinomiya et al., Effects of kava-kava extract on the sleep wake cycle in sleep-disturbed rats. Psychopharmacology. Jul. 2005;180(3):564-9. Epub Feb. 8, 2005.
Singh, Kava: an overview. J Ethnopharmacol. Aug. 1992;37(1):13-45.
Wisstock et al., Prediction of protein function from protein sequence and structure. Q Rev Biophys. Aug. 2003;36(3):307-40. doi: 10.1017/s0033583503003901.
Witkowski et al., Conversion of a beta-ketoacyl synthase to a malonyl decarboxylase by replacement of the active-site cysteine with glutamine. Biochemistry. Sep. 7, 1999;38(36):11643-50. doi: 10.1021/bi990993h.

*Primary Examiner* — Tekchand Saidha
*Assistant Examiner* — Mohammad Y Meah
(74) *Attorney, Agent, or Firm* — Wolf, Greenfield & Sacks, P.C.

(57) ABSTRACT

Disclosed are methods, compositions, proteins, nucleic acids, cells, vectors, compounds, reagents, and systems for the preparation of kavalactones, flavokavains, and kavalactone and flavokavain biosynthetic intermediates using enzymes expressed in heterologous host cells, such as microorganisms or plants, or using in vitro enzymatic reactions. This invention also provides for the expression of the enzymes by recombinant cell lines and vectors. Furthermore, the enzymes can be components of constructs such as fusion proteins. The kavalactones produced can be utilized to treat anxiety disorder, insomnia, and other psychological and neurological disorders. The flavokavains produced can be utilized to treat various cancers including colon, bladder, and breast cancers.

16 Claims, 10 Drawing Sheets
Specification includes a Sequence Listing.

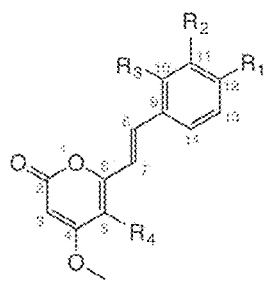

| Kavalactone | R₁ | R₂ | R₃ | R₄ | C₅-C₆ | C₇-C₈ |
|---|---|---|---|---|---|---|
| Kavain | | | | | --- | === |
| Yangonin | OCH₃ | | | | === | === |
| Methysticin | | OCH₂O | | | --- | === |
| 7,8-Dihydrokavain (Marindinin) | | | | | --- | --- |
| Desmethoxyyangonin | | | | | === | === |
| 7,8-Dihydromethysticin | | OCH₂O | | | --- | --- |
| 5-hydroxykavain | | | | OH | --- | === |
| 5,6-dehydromethysticin | | OCH₂O | | | === | === |
| 5,6-dihydro-11-methoxyyangonin | OCH₃ | OCH₃ | | | --- | === |
| 5,6-dihydroyangonin | OCH₃ | | | | --- | === |
| 5,6,7,8-tetrahydroyangonin | OCH₃ | | | | --- | --- |
| 7,8-dihydro-5-hydroxykavain | | | | OH | --- | --- |
| 7,8-dihydro-5,6-dehydrokavain (DDK) | | | | | === | --- |
| 7,8-dihydroyangonin | OCH₃ | | | | === | --- |
| 10-methoxyyangonin | OCH₃ | | OCH₃ | | === | === |
| 11-hydroxy-12-methoxydihydrokavain | OCH₃ | OH | | | --- | --- |
| 11-hydroxyyangonin | OCH₃ | OH | | | === | === |
| 11-methoxy-12-hydroxydehydrokavain | OH | OCH₃ | | | === | === |
| 11-methoxyyangonin | OCH₃ | OCH₃ | | | === | === |
| 11,12-dimethoxydihydrokavain | OCH₃ | OCH₃ | | | --- | --- |

Figure 1

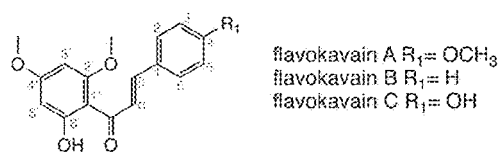

flavokavain A R₁= OCH₃
flavokavain B R₁= H
flavokavain C R₁= OH

Figure 2

SEQUENCE LISTING

<160> NUMBER OF SEQ ID NOS: 16

<210> SEQ ID NO 1
<211> LENGTH: 545
<212> TYPE: PRT
<213> ORGANISM: Artificial Sequence
<220> FEATURE:

<223> OTHER INFORMATION: Synthetic polypeptide

<400> SEQUENCE: 1

```
Met Lys Met Val Val Asp Thr Ile Ala Thr Asp Arg Cys Val Tyr Arg
1               5                   10                  15

Ser Lys Leu Pro Asp Ile Glu Ile Lys Asn Asp Met Ser Leu His Asn
            20                  25                  30

Tyr Cys Phe Gln Asn Ile Gly Ala Tyr Arg Asp Asn Pro Cys Leu Ile
        35                  40                  45

Asn Gly Ser Thr Gly Glu Val Tyr Thr Tyr Gly Val Glu Thr Thr
    50                  55                  60

Ala Arg Arg Val Ala Ala Gly Leu His Arg Met Gly Val Gln Gln Arg
65                  70                  75                  80

Glu Val Ile Met Ile Leu Leu Pro Asn Ser Pro Glu Phe Val Phe Ala
                85                  90                  95

Phe Leu Gly Ala Ser Phe Arg Gly Ala Met Ser Thr Thr Ala Asn Pro
            100                 105                 110

Phe Tyr Thr Pro Gln Glu Ile Ala Lys Gln Val Lys Ala Ser Gly Ala
        115                 120                 125

Lys Leu Ile Val Thr Met Ser Ala Tyr Val Asp Lys Val Arg Asp Leu
    130                 135                 140

Ala Glu Glu Arg Gly Val Lys Val Val Cys Val Asp Ala Pro Pro Pro
145                 150                 155                 160

Gly Cys Ser His Phe Ser Glu Leu Ser Gly Ala Asp Glu Ser Glu Leu
                165                 170                 175

Pro Glu Val Asp Ile Asp Pro Asp Val Val Ala Leu Pro Tyr Ser
            180                 185                 190

Ser Gly Thr Thr Gly Leu Pro Lys Gly Val Met Leu Thr His Arg Ser
        195                 200                 205

Gln Val Thr Ser Val Ala Gln Gln Val Asp Gly Glu Asn Pro Asn Leu
    210                 215                 220

Tyr Phe Arg Pro Asp Asp Val Leu Leu Cys Val Leu Pro Leu Phe His
225                 230                 235                 240

Ile Tyr Ser Leu Asn Ser Val Leu Phe Cys Gly Leu Arg Val Gly Ala
                245                 250                 255

Ala Ile Leu Ile Met Gln Lys Phe Glu Ile Thr Ala Leu Met Glu Leu
            260                 265                 270

Val Gln Lys Tyr Lys Val Thr Ile Ala Pro Ile Val Pro Pro Ile Val
        275                 280                 285

Leu Ala Ile Ala Lys Ser Pro Leu Val Asp Lys Tyr Asp Leu Ser Ser
    290                 295                 300

Ile Arg Thr Val Met Ser Gly Ala Ala Pro Met Gly Lys Glu Leu Glu
305                 310                 315                 320

Asp Ala Val Arg Ala Lys Leu Pro Asn Ala Lys Leu Gly Gln Gly Tyr
                325                 330                 335

Gly Met Thr Glu Ala Gly Pro Val Leu Ser Met Cys Leu Ala Phe Ala
            340                 345                 350

Lys Glu Pro Phe Glu Ile Lys Ser Gly Ser Cys Gly Thr Val Val Arg
        355                 360                 365

Asn Ala Gln Leu Lys Ile Val Asp Pro Glu Thr Gly Ala Tyr Leu Pro
    370                 375                 380

Arg Asn Gln Pro Gly Glu Ile Cys Ile Arg Gly Ser Gln Ile Met Lys
385                 390                 395                 400
```

```
Gly Tyr Leu Asn Asp Ala Ala Ala Thr Gln Arg Thr Ile Asp Lys Glu
                405                 410                 415

Gly Trp Leu His Thr Gly Asp Ile Gly Tyr Val Asp Asp Glu Glu
        420                 425                 430

Leu Phe Ile Val Asp Arg Leu Lys Glu Ile Ile Lys Tyr Lys Gly Phe
            435                 440                 445

Gln Val Ala Pro Ala Glu Leu Glu Ala Ile Leu Ile Thr His Pro Asn
    450                 455                 460

Ile Ala Asp Ala Ala Val Val Pro Met Lys Asp Glu Ala Ala Gly Glu
465                 470                 475                 480

Val Pro Val Ala Phe Val Val Thr Ser Asn Gly Ser Val Ile Ser Glu
                485                 490                 495

Asp Glu Ile Lys Gln Phe Ile Ser Lys Gln Val Val Phe Tyr Lys Arg
                500                 505                 510

Ile Asn Arg Val Phe Phe Val Asp Ser Ile Pro Lys Ala Pro Ser Gly
            515                 520                 525

Lys Ile Leu Arg Lys Asp Leu Arg Gly Arg Leu Ala Ala Gly Ile Pro
530                 535                 540

Lys
545

<210> SEQ ID NO 2
<211> LENGTH: 397
<212> TYPE: PRT
<213> ORGANISM: Artificial Sequence
<220> FEATURE:
<223> OTHER INFORMATION: Synthetic polypeptide

<400> SEQUENCE: 2

Met Ser Lys Thr Val Glu Asp Arg Ala Ala Gln Arg Ala Lys Gly Pro
1               5                   10                  15

Ala Thr Val Leu Ala Ile Gly Thr Ala Thr Pro Ala Asn Val Val Tyr
                20                  25                  30

Gln Thr Asp Tyr Pro Asp Tyr Tyr Phe Arg Val Thr Lys Ser Glu His
            35                  40                  45

Met Thr Lys Leu Lys Asn Lys Phe Gln Arg Met Cys Asp Arg Ser Thr
        50                  55                  60

Ile Lys Lys Arg Tyr Met Val Leu Thr Glu Glu Leu Leu Glu Lys Asn
65                  70                  75                  80

Leu Ser Leu Cys Thr Tyr Met Glu Pro Ser Leu Asp Ala Arg Gln Asp
                85                  90                  95

Ile Leu Val Pro Glu Val Pro Lys Leu Gly Lys Glu Ala Ala Asp Glu
            100                 105                 110

Ala Ile Ala Glu Trp Gly Arg Pro Lys Ser Glu Ile Thr His Leu Ile
        115                 120                 125

Phe Cys Thr Thr Cys Gly Val Asp Met Pro Gly Ala Asp Tyr Gln Leu
    130                 135                 140

Thr Lys Leu Leu Gly Leu Arg Ser Ser Val Arg Arg Thr Met Leu Tyr
145                 150                 155                 160

Gln Gln Gly Cys Phe Gly Gly Gly Thr Val Leu Arg Leu Ala Lys Asp
                165                 170                 175

Leu Ala Glu Asn Asn Ala Gly Ala Arg Val Leu Val Val Cys Ser Glu
            180                 185                 190

Ile Thr Thr Ala Val Asn Phe Arg Gly Pro Ser Asp Thr His Leu Asp
        195                 200                 205
```

```
Leu Leu Val Gly Leu Ala Leu Phe Gly Asp Gly Ala Ala Val Ile
210                 215                 220

Val Gly Ala Asp Pro Asp Pro Thr Leu Glu Arg Pro Leu Phe Gln Ile
225                 230                 235                 240

Val Ser Gly Ala Gln Thr Ile Leu Pro Asp Ser Glu Gly Ala Ile Asn
                245                 250                 255

Gly His Leu Arg Glu Val Gly Leu Thr Ile Arg Leu Leu Lys Asp Val
            260                 265                 270

Pro Gly Leu Val Ser Met Asn Ile Glu Lys Cys Leu Met Glu Ala Phe
        275                 280                 285

Ala Pro Met Gly Ile His Asp Trp Asn Ser Ile Phe Trp Ile Ala His
290                 295                 300

Pro Gly Gly Pro Thr Ile Leu Asp Gln Val Glu Ala Lys Leu Gly Leu
305                 310                 315                 320

Lys Glu Glu Lys Leu Lys Ser Thr Arg Ala Val Leu Arg Glu Tyr Gly
                325                 330                 335

Asn Met Ser Ser Ala Cys Val Leu Phe Ile Leu Asp Glu Val Arg Lys
            340                 345                 350

Arg Ser Met Glu Glu Gly Lys Thr Thr Thr Gly Glu Gly Phe Asp Trp
        355                 360                 365

Gly Val Leu Phe Gly Phe Gly Pro Gly Phe Thr Val Glu Thr Val Val
370                 375                 380

Leu His Ser Met Pro Ile Pro Lys Ala Asp Glu Gly Arg
385                 390                 395

<210> SEQ ID NO 3
<211> LENGTH: 394
<212> TYPE: PRT
<213> ORGANISM: Artificial Sequence
<220> FEATURE:
<223> OTHER INFORMATION: Synthetic polypeptide

<400> SEQUENCE: 3

Met Ser Lys Met Val Glu Glu His Trp Ala Ala Gln Arg Ala Arg Gly
1               5                   10                  15

Pro Ala Thr Val Leu Ala Ile Gly Thr Ala Asn Pro Pro Asn Val Leu
                20                  25                  30

Tyr Gln Ala Asp Tyr Pro Asp Phe Tyr Phe Arg Val Thr Lys Ser Glu
            35                  40                  45

His Met Thr Gln Leu Lys Glu Lys Phe Lys Arg Ile Cys Asp Lys Ser
        50                  55                  60

Ala Ile Arg Lys Arg His Leu His Leu Thr Glu Glu Leu Leu Glu Lys
65                  70                  75                  80

Asn Pro Asn Ile Cys Ala His Met Ala Pro Ser Leu Asp Ala Arg Gln
                85                  90                  95

Asp Ile Ala Val Val Glu Val Pro Lys Leu Ala Lys Glu Ala Ala Thr
            100                 105                 110

Lys Ala Ile Lys Glu Trp Gly Arg Pro Lys Ser Asp Ile Thr His Leu
        115                 120                 125

Ile Phe Cys Thr Thr Cys Gly Val Asp Met Pro Gly Ala Asp Tyr Gln
    130                 135                 140

Leu Thr Thr Leu Leu Gly Leu Arg Pro Thr Val Arg Arg Thr Met Leu
145                 150                 155                 160

Tyr Gln Gln Gly Cys Phe Ala Gly Gly Thr Val Leu Arg His Ala Lys
                165                 170                 175
```

Asp Phe Ala Glu Asn Asn Arg Gly Ala Arg Val Leu Ala Val Cys Ser
            180                 185                 190

Glu Phe Thr Val Met Asn Phe Ser Gly Pro Ser Glu Ala His Leu Asp
        195                 200                 205

Ser Met Val Gly Met Ala Leu Phe Gly Asp Gly Ala Ser Ala Val Ile
    210                 215                 220

Val Gly Ala Asp Pro Asp Phe Ala Ile Glu Arg Pro Leu Phe Gln Leu
225                 230                 235                 240

Val Ser Thr Thr Gln Thr Ile Val Pro Asp Ser Asp Gly Ala Ile Lys
                245                 250                 255

Cys His Leu Lys Glu Val Gly Leu Thr Leu His Leu Val Lys Asn Val
            260                 265                 270

Pro Asp Leu Ile Ser Asn Asn Met Asp Lys Ile Leu Glu Glu Ala Phe
        275                 280                 285

Ala Pro Leu Gly Ile Arg Asp Trp Asn Ser Ile Phe Trp Thr Ala His
    290                 295                 300

Pro Gly Gly Ala Ala Ile Leu Asp Gln Leu Glu Ala Lys Leu Gly Leu
305                 310                 315                 320

Asn Lys Glu Lys Leu Lys Thr Thr Arg Thr Val Leu Arg Glu Tyr Gly
                325                 330                 335

Asn Met Ser Ser Ala Cys Val Cys Phe Val Leu Asp Glu Met Arg Arg
            340                 345                 350

Ser Ser Leu Glu Glu Gly Lys Thr Thr Ser Gly Glu Gly Leu Glu Trp
        355                 360                 365

Gly Ile Leu Leu Gly Phe Gly Pro Gly Leu Thr Val Glu Thr Val Val
    370                 375                 380

Leu Arg Ser Val Pro Ile Ser Thr Ala Asn
385                 390

<210> SEQ ID NO 4
<211> LENGTH: 394
<212> TYPE: PRT
<213> ORGANISM: Artificial Sequence
<220> FEATURE:
<223> OTHER INFORMATION: Synthetic polypeptide

<400> SEQUENCE: 4

Met Ser Lys Thr Val Glu Glu Ile Trp Ala Ala Gln Arg Ala Arg Gly
1               5                   10                  15

Pro Ala Thr Val Leu Ala Ile Gly Thr Ala Ala Pro Ala Asn Val Val
            20                  25                  30

Tyr Gln Ala Asp Tyr Pro Asp Tyr Tyr Phe Arg Ile Thr Lys Ser Glu
        35                  40                  45

His Met Thr Glu Leu Lys Glu Lys Phe Arg Arg Met Cys Asp Lys Ser
    50                  55                  60

Met Ile Thr Lys Arg His Met His Leu Ser Glu Glu Leu Leu Lys Asn
65                  70                  75                  80

Asn Pro Asp Ile Cys Ala Tyr Met Ala Pro Ser Leu Asp Ala Arg Gln
            85                  90                  95

Asp Met Val Val Val Glu Val Pro Lys Leu Gly Lys Glu Ala Ala Ala
        100                 105                 110

Lys Ala Ile Lys Glu Trp Gly Arg Pro Lys Ser Ala Ile Thr His Leu
    115                 120                 125

Ile Phe Cys Thr Thr Ser Gly Val Asp Met Pro Gly Ala Asp Phe Gln
        130                 135                 140

```
Leu Thr Lys Leu Leu Gly Leu Cys Pro Ser Val Arg Arg Thr Met Leu
145                 150                 155                 160

Tyr Gln Gln Gly Cys Phe Ala Gly Gly Thr Val Leu Arg Leu Ala Lys
            165                 170                 175

Asp Leu Ala Glu Asn Asn Ala Gly Ala Arg Val Leu Val Val Cys Ser
        180                 185                 190

Glu Ile Thr Ala Val Thr Phe Arg Gly Pro Ser Glu Thr His Leu Asp
    195                 200                 205

Ser Met Val Gly Gln Ala Leu Phe Gly Asp Gly Ala Ser Ala Ile Ile
210                 215                 220

Val Gly Ala Asp Pro Asp Pro Val Ile Glu Arg Pro Leu Phe Gln Ile
225                 230                 235                 240

Val Ser Ala Ala Gln Thr Ile Leu Pro Asp Ser Asp Gly Ala Ile Asp
            245                 250                 255

Gly His Leu Arg Glu Val Gly Leu Thr Phe His Leu Leu Lys Asp Val
        260                 265                 270

Pro Gly Leu Ile Ser Lys Asn Ile Glu Lys Ser Leu Lys Glu Ala Phe
    275                 280                 285

Ala Pro Leu Gly Ile Asp Asp Trp Asn Ser Ile Phe Trp Ile Val His
290                 295                 300

Pro Gly Gly Pro Ala Ile Leu Asp Gln Val Glu Ala Lys Leu Arg Leu
305                 310                 315                 320

Lys Val Glu Lys Leu Lys Thr Thr Arg Thr Val Leu Ser Glu Tyr Gly
            325                 330                 335

Asn Met Ser Ser Ala Cys Val Leu Phe Ile Leu Asp Glu Met Arg Arg
        340                 345                 350

Asn Ser Met Glu Glu Gly Lys Ala Thr Thr Gly Glu Gly Leu His Trp
    355                 360                 365

Gly Val Leu Phe Gly Phe Gly Pro Gly Leu Thr Val Glu Thr Val Val
370                 375                 380

Leu His Ser Leu Pro Ile Ala Glu Ala Asn
385                 390

<210> SEQ ID NO 5
<211> LENGTH: 361
<212> TYPE: PRT
<213> ORGANISM: Artificial Sequence
<220> FEATURE:
<223> OTHER INFORMATION: Synthetic polypeptide

<400> SEQUENCE: 5

Met Glu Gln Ala Val Phe Lys Asp Gln Ser Pro Ser Arg Asp Asp Ile
1               5                   10                  15

Asp Glu Glu Leu Phe Gln Ser Ala Leu Tyr Leu Ser Thr Ala Val Val
            20                  25                  30

Thr Val Pro Ala Ala Ile Met Ala Ala Asn Asp Leu Asp Val Leu Gln
        35                  40                  45

Ile Ile Ala Lys Ala Gly Pro Gly Ala His Leu Ser Pro Thr Glu Ile
    50                  55                  60

Val Ser His Leu Pro Thr Arg Asn Pro Asn Ala Ala Ala Leu His Arg
65                  70                  75                  80

Arg Ile Leu Arg Val Leu Ala Ser His Ser Ile Leu Glu Cys Ser Ser
            85                  90                  95

Arg Cys Glu Gly Glu Ala Lys Tyr Gly Leu Arg Pro Val Cys Lys Phe
        100                 105                 110
```

Phe Leu Asn Asp Lys Asp Gly Val Ser Leu Asn Ala Met Pro Ser Phe
            115                 120                 125

Val Gln Ser Arg Val Phe Ile Asp Ser Trp Gln Tyr Met Lys Asp Ala
        130                 135                 140

Val Leu Glu Gly Val Val Pro Phe Glu Lys Ala Tyr Gly Met Pro Phe
145                 150                 155                 160

Tyr Gln Phe Gln Ala Val Asn Thr Lys Phe Lys Glu Thr Phe Ala Lys
                165                 170                 175

Ala Met Ala Ala His Ser Thr Leu Val Lys Lys Met Leu Asp Thr
            180                 185                 190

Tyr Asn Gly Phe Glu Gly Leu Thr Glu Leu Met Asp Val Ala Gly Gly
        195                 200                 205

Thr Gly Ser Thr Leu Asn Leu Ile Val Ser Lys Tyr Pro Gln Ile Lys
210                 215                 220

Gly Thr Asn Phe Asp Leu Lys His Val Ile Glu Ala Ala Pro Asn Tyr
225                 230                 235                 240

Pro Gly Val Lys His Leu Ser Gly Asp Met Phe Asp Ser Ile Pro Ser
                245                 250                 255

Ala Lys Asn Ile Ile Met Lys Trp Ile Leu His Asn Trp Ser Asp Glu
            260                 265                 270

His Cys Val Lys Leu Leu Lys Asn Cys Tyr Thr Ser Leu Pro Glu Phe
        275                 280                 285

Gly Lys Leu Ile Val Val Asp Ser Ile Val Gly Glu Asp Val Asp Ala
290                 295                 300

Gly Leu Thr Thr Thr Asn Val Phe Gly Cys Asp Phe Thr Met Leu Thr
305                 310                 315                 320

Phe Phe Pro Asn Ala Lys Glu Arg Thr Arg Glu Glu Phe Gln Asp Leu
                325                 330                 335

Ala Lys Ala Ser Gly Phe Ser Thr Phe Lys Pro Ile Cys Cys Ala Tyr
            340                 345                 350

Gly Val Trp Val Met Glu Phe His Lys
        355                 360

<210> SEQ ID NO 6
<211> LENGTH: 360
<212> TYPE: PRT
<213> ORGANISM: Artificial Sequence
<220> FEATURE:
<223> OTHER INFORMATION: Synthetic polypeptide

<400> SEQUENCE: 6

Met Asn Asp Gln Glu Leu His Gly Tyr Ser Gln Asn Ala Gln Pro Gln
1               5                   10                  15

Leu Trp Asn Leu Leu Leu Ser Phe Ile Asn Ser Met Ser Leu Lys Cys
            20                  25                  30

Ala Val Glu Leu Gly Ile Pro Asp Ile His Ser His Ala Gln Thr
        35                  40                  45

Pro Ile Asn Ile Thr Asp Leu Ala Ala Ser Ile Pro Ile Pro Pro Asn
    50                  55                  60

Lys Thr Ser Gln Phe Arg Arg Leu Met Arg Leu Leu Val His Ser Asn
65                  70                  75                  80

Val Phe Ser Val His Lys Arg Glu Asp Gly Asp Glu Gly Phe Leu Leu
                85                  90                  95

Thr Pro Met Ser Arg Ile Leu Val Thr Ser Asn Asp Asn Asn Gly Gly
            100                 105                 110

Asn Leu Ser Pro Phe Val Ser Met Met Val Asp Pro Ser Leu Val Ser
            115                 120                 125

Pro Trp His Phe Leu Gly Gln Trp Leu Lys Gly Asn Asp Thr Gln Gly
130                 135                 140

Thr Pro Phe Arg Met Cys His Gly Glu Glu Met Trp Asp Trp Ala Asn
145                 150                 155                 160

Lys Tyr Pro Asp Phe Asn Lys Phe Asn Met Ala Met Val Cys Asp
                165                 170                 175

Ser Gln Tyr Leu Met Lys Ile Ile Val Lys Lys Cys Ala Thr Ala Phe
            180                 185                 190

Glu Gly Lys Arg Ser Leu Ile Asp Val Gly Gly Thr Gly Gly Ala
        195                 200                 205

Ala Arg Ser Ile Ala Glu Ala Phe Pro Asp Ile Gln Glu Val Ser Val
210                 215                 220

Leu Asp Leu Pro His Val Ala Gly Leu Pro Asn Asp Ser Arg Val
225                 230                 235                 240

Lys Phe Val Gly Gly Asp Met Phe His Thr Ile Pro Pro Ala Asp Val
                245                 250                 255

Val Leu Leu Lys Ala Ile Phe His Gly Trp Asn Asp Glu Glu Cys Ile
            260                 265                 270

Lys Ile Leu Lys Asn Cys Lys Lys Ala Ile Pro Ser Lys Glu Glu Gly
        275                 280                 285

Gly Lys Val Met Ile Leu Asp Met Val Val Asn Ser Ala Pro Gly Asp
    290                 295                 300

His Met Ile Thr Glu Asp Gln Tyr Phe Met Asp Leu Met Met Ile Thr
305                 310                 315                 320

Tyr Ala Arg Gly Leu Glu Arg Asp Glu Asn Glu Trp Lys Lys Leu Phe
                325                 330                 335

Lys Asp Ala Gly Phe Thr Ser Tyr Lys Ile Thr His Gly Leu Gly Thr
            340                 345                 350

Ser Ser Leu Ile Glu Leu Tyr Pro
        355                 360

<210> SEQ ID NO 7
<211> LENGTH: 511
<212> TYPE: PRT
<213> ORGANISM: Artificial Sequence
<220> FEATURE:
<223> OTHER INFORMATION: Synthetic polypeptide

<400> SEQUENCE: 7

Met Glu Gln Ala Gln Trp Val Asp Pro Thr Leu Leu Pro Ala Phe Val
1               5                   10                  15

Gly Ile Ile Phe Phe Phe Leu Gly Met Phe Phe Gly Arg Ser Ser Leu
            20                  25                  30

Gly Ala Gly Lys Gly Ala Ala Pro Arg Ser Thr Ser Ser Thr Glu Trp
        35                  40                  45

Pro Asp Gly Pro Pro Lys Leu Pro Ile Ile Gly Asn Leu His Gln Leu
50                  55                  60

Asn Lys Gly Gly Glu Leu Val His His Asn Leu Ala Lys Leu Ala Gln
65                  70                  75                  80

Ser Tyr Asp Arg Ala Met Thr Ile Trp Val Gly Ser Trp Gly Pro Met
                85                  90                  95

Ile Val Val Ser Asp Ala Asp Leu Ala Trp Glu Val Leu Val Thr Lys
            100                 105                 110

Ser Pro Asp Phe Ala Gly Arg Val Leu Ser Lys Leu Ser His Leu Phe
115                 120                 125

Asn Ala Asn Tyr Asn Thr Val Val Ala Tyr Asp Ala Gly Pro Gln Trp
130                 135                 140

Gln Ser Leu Arg Arg Gly Leu Gln His Gly Pro Leu Gly Pro Ala His
145                 150                 155                 160

Val Ser Ala Gln Ala Arg Phe His Glu Glu Asp Met Lys Leu Leu Val
                165                 170                 175

Ser Asp Met Met Arg Ala Ala Gln Lys Gly Gly Ser Asn Gly Val Val
            180                 185                 190

Glu Pro Leu Ala Tyr Val Arg Arg Ala Thr Ile Arg Phe Leu Ser Arg
        195                 200                 205

Leu Cys Phe Gly Glu Ala Phe Asn Asp Glu Ala Phe Val Glu Gly Met
210                 215                 220

Asp Glu Ala Val Glu Glu Thr Ile Gly Ala Thr Gly His Ala Arg Ile
225                 230                 235                 240

Leu Asp Ala Phe Tyr Phe Thr Arg His Leu Pro Ile Ile Arg Arg Ser
                245                 250                 255

Phe Ile Asp Thr Val Asn Ala Lys Lys Lys Ile Glu Ser Leu Val Arg
            260                 265                 270

Pro Leu Leu Ser Arg Pro Ala Pro Gly Ser Tyr Leu His Phe Leu
        275                 280                 285

Leu Ser Thr Asp Ala Pro Glu Asn Met Ile Ile Phe Arg Ile Phe Glu
    290                 295                 300

Val Tyr Leu Leu Gly Val Asp Ser Thr Ala Ser Thr Thr Thr Trp Ala
305                 310                 315                 320

Leu Ala Phe Leu Val Ser Asn Gln Gln Ala Gln Glu Lys Leu His Asn
                325                 330                 335

Glu Leu Ala Gln Tyr Cys Ala Ser Gln Asn Asn Gln Ile Ile Lys Ala
            340                 345                 350

Asp Asp Val Gly Lys Leu Ser Tyr Leu Leu Gly Val Val Lys Glu Thr
        355                 360                 365

Met Arg Met Lys Pro Ile Ala Pro Leu Ala Val Pro His Lys Thr Leu
370                 375                 380

Lys Glu Thr Met Leu Asp Gly Lys Arg Val Ala Ala Gly Thr Thr Val
385                 390                 395                 400

Val Val Asn Leu Tyr Ala Val His Tyr Asn Pro Lys Leu Trp Pro Glu
                405                 410                 415

Pro Glu Gln Phe Arg Pro Glu Arg Phe Val Val Gly Ala Ser Gly Gly
            420                 425                 430

Asn Gly Gly Ser Ser Glu Tyr Met Leu Gln Ser Tyr Leu Pro Phe
        435                 440                 445

Gly Gly Gly Met Arg Ser Cys Ala Gly Met Glu Val Gly Lys Leu Gln
    450                 455                 460

Val Ala Met Val Val Ala Asn Leu Val Met Ala Phe Lys Trp Leu Pro
465                 470                 475                 480

Glu Glu Glu Gly Lys Met Pro Asp Leu Ala Glu Asp Met Thr Phe Val
                485                 490                 495

Leu Met Met Lys Lys Pro Leu Ala Ala Lys Ile Val Pro Arg Ala
            500                 505                 510

<210> SEQ ID NO 8
<211> LENGTH: 326
<212> TYPE: PRT

<213> ORGANISM: Artificial Sequence
<220> FEATURE:
<223> OTHER INFORMATION: Synthetic polypeptide

<400> SEQUENCE: 8

```
Met Glu Thr Glu Arg Lys Ser Arg Ile Cys Val Thr Gly Ala Gly Gly
1               5                   10                  15

Phe Val Ala Ser Trp Val Val Lys Leu Phe Leu Ser Lys Gly Tyr Leu
            20                  25                  30

Val His Gly Thr Val Arg Asp Leu Gly Glu Lys Thr Ala His Leu
        35                  40                  45

Arg Lys Leu Glu Gly Ala Tyr His Asn Leu Gln Leu Phe Lys Ala Asp
    50                  55                  60

Leu Leu Asp Tyr Glu Ser Leu Leu Gly Ala Ile Thr Gly Cys Asp Gly
65                  70                  75                  80

Val Leu His Val Ala Thr Pro Val Pro Ser Lys Thr Ala Tyr Ser
                85                  90                  95

Gly Thr Glu Leu Val Lys Thr Ala Val Asn Gly Thr Leu Asn Val Leu
                100                 105                 110

Arg Ala Cys Thr Glu Ala Lys Val Lys Lys Val Ile Tyr Val Ser Ser
                115                 120                 125

Thr Ala Ala Val Leu Val Asn Pro Asn Leu Pro Lys Asp Lys Ile Pro
    130                 135                 140

Asp Glu Asp Cys Trp Thr Asp Glu Glu Tyr Cys Arg Thr Thr Pro Phe
145                 150                 155                 160

Phe Leu Asn Trp Tyr Cys Ile Ala Lys Thr Ala Ala Glu Lys Asn Ala
                165                 170                 175

Leu Glu Tyr Gly Asp Lys Glu Gly Ile Asn Val Ile Ser Ile Cys Pro
            180                 185                 190

Ser Tyr Ile Phe Gly Pro Met Leu Gln Pro Thr Ile Asn Ser Ser Asn
        195                 200                 205

Leu Glu Leu Leu Arg Leu Met Lys Gly Asp Asp Glu Ser Ile Glu Asn
    210                 215                 220

Lys Phe Leu Leu Met Val Asp Val Arg Asp Val Ala Glu Ala Ile Leu
225                 230                 235                 240

Leu Leu Tyr Glu Lys Gln Glu Thr Ser Gly Arg Tyr Ile Ser Ser Pro
                245                 250                 255

His Gly Met Arg Gln Ser Asn Leu Val Glu Lys Leu Glu Ser Leu Gln
                260                 265                 270

Pro Gly Tyr Asn Tyr His Lys Asn Phe Val Asp Ile Lys Pro Ser Trp
            275                 280                 285

Thr Met Ile Ser Ser Glu Lys Leu Lys Lys Leu Gly Trp Lys Pro Arg
        290                 295                 300

Pro Leu Glu Asp Thr Ile Ser Glu Thr Val Leu Cys Phe Glu Glu His
305                 310                 315                 320

Gly Leu Leu Glu Asn Glu
                325
```

<210> SEQ ID NO 9
<211> LENGTH: 1638
<212> TYPE: DNA
<213> ORGANISM: Artificial Sequence
<220> FEATURE:
<223> OTHER INFORMATION: Synthetic polynucleotide

<400> SEQUENCE: 9

| | |
|---|---:|
| atgaagatgg tagtagacac tattgctact gatcgatgtg tataccggtc taagctgccg | 60 |
| gacattgaga tcaagaacga catgtcgttg cacaattatt gtttccagaa cattggtgct | 120 |
| taccgggaca atccttgtct catcaatggc agcaccggcg aggtgtacac gtacggcgag | 180 |
| gtggagacga cggcgaggag ggtggccgcc gggctgcacc ggatgggggt gcagcagcgg | 240 |
| gaggtgatca tgatcctcct ccccaactcg ccggagttcg tcttcgcctt cctcggcgcc | 300 |
| tccttccgcg gggccatgtc caccaccgcc aaccccttct acacgccgca ggagatcgcc | 360 |
| aagcaggtca aggcctccgg cgcgaagctc atcgtcacca tgtccgccta cgtcgacaag | 420 |
| gtcagggacc tggccgagga gcgcggcgtc aaagtggtgt gcgtcgacgc gccgccccg | 480 |
| gggtgctccc acttctccga gctgtccggc gccgacgagt cggagctgcc cgaggtggat | 540 |
| attgaccccg acgacgtggt ggcgctgcca tactcctccg gcaccaccgg cctccctaaa | 600 |
| ggagtgatgc tcacacaccg cagccaggtg acgagcgttg cccagcaagt cgacggcgag | 660 |
| aacccgaatc tatacttccg gccagacgac gtcctgctct gcgttcttcc cctcttccac | 720 |
| atctactccc tcaactcggt gctcttctgc ggcctgcgcg tcggggcggc gatcctcatc | 780 |
| atgcagaagt tcgagatcac ggcgctgatg gagctggtgc agaagtacaa ggtgaccatt | 840 |
| gcgcccatcg ttccgcccat cgttcttgcc atcgccaaga gcccgctcgt cgacaagtac | 900 |
| gacttgtcgt ccattcggac ggtgatgtcc ggcgccgccc cgatggggaa ggagctcgaa | 960 |
| gacgccgtcc gggccaagct tcccaacgcc aagctcggcc agggctatgg gatgacggag | 1020 |
| gcagggccag tgctgtccat gtgtttggcc ttcgccaagg agcccttcga gatcaagtct | 1080 |
| ggttcttgcg gcaccgtggt caggaacgcc cagctcaaga tcgtcgaccc agaaaccggt | 1140 |
| gcctacctgc ccagaaacca acccggcgaa atttgcatcc gaggctccca aatcatgaaa | 1200 |
| gggtatctta atgacgcggc ggctacgcag aggacgatcg acaaggaagg gtggctgcac | 1260 |
| accggcgaca ttggctatgt cgacgacgac gaggagctct tcattgtcga taggttgaag | 1320 |
| gagatcatta agtacaaggg cttccaagtc gcccctgccg agctcgaagc cattctcatt | 1380 |
| actcacccta acattgctga tgccgctgtt gtcccgatga agatgaggc agcagggga | 1440 |
| gtgccagtgg catttgtggt gacctccaat ggatcagtca tcagtgagga tgagatcaag | 1500 |
| cagttcatta gcaagcaggt ggtgttctac aagcgaatca atcgagtctt tttcgttgat | 1560 |
| tcaattccta aagcaccctc tgggaagatt tgaggaagg atttgagggg aagattggca | 1620 |
| gctggtatac ccaagtag | 1638 |

<210> SEQ ID NO 10
<211> LENGTH: 1194
<212> TYPE: DNA
<213> ORGANISM: Artificial Sequence
<220> FEATURE:
<223> OTHER INFORMATION: Synthetic polynucleotide

<400> SEQUENCE: 10

| | |
|---|---:|
| atgtcgaaga cggtggagga tcgggcagcg cagcgggcaa aggggccggc aacagtgctg | 60 |
| gccatcggca cggctacgcc ggccaatgtg gtgtaccaga ccgattatcc ggactactac | 120 |
| ttcagggtca ccaagagcga gcatatgacc aaactcaaga caagtttca acgcatgtgc | 180 |
| gacaggtcga cgataaagaa gaggtacatg gttttgacag aggagctgct agagaagaat | 240 |
| ctgagtttgt gcacctacat ggaaccctcc ctcgacgccc gcaagacat tctcgtgccg | 300 |
| gaggtcccca gctcggcaa ggaggccgcc gacgaggcca tcgccgaatg ggacgcccc | 360 |
| aagtcggaaa tcacccacct catctttttgc actacctgcg gcgtcgacat gcccggcgcc | 420 |

| | |
|---|---|
| gactaccagc tcaccaagct cctcggtctc cgctcctccg tccgtcgcac catgctctat | 480 |
| cagcagggat gctttggcgg aggcaccgtt ctccgcctcg ccaaggacct cgccgagaac | 540 |
| aacgctggtg cccgcgtcct cgtcgtctgc tccgagatca ccactgccgt caacttccga | 600 |
| gggccttccg acacccacct cgacttattg gtcggcttag ccctgttcgg cgacggtgcg | 660 |
| gccgcggtca tagtcggtgc ggatccagat cctaccctcg agcggccgct ctttcaaatc | 720 |
| gtatctggag cacagacgat tctaccggac tcggaggggg ccatcaacgg ccatctccgg | 780 |
| gaggtggggc taaccatccg cctactcaag gacgtacctg gcttgtgtc gatgaacatt | 840 |
| gagaagtgcc tcatggaggc gtttgcaccg atgggcatcc acgactggaa ctccatcttt | 900 |
| tggatagccc atcccggggg gcccaccata ctagaccaag tggaggccaa gctgggtcta | 960 |
| aaggaggaga agctcaagtc gacgagggct gttctgaggg agtatggcaa catgtctagc | 1020 |
| gcctgtgtct tgttcatact ggacgaggta aggaagagga gcatggagga ggggaagacg | 1080 |
| acaaccggtg aggggttcga ttggggagtt ctattcggct ttgggcctgg cttcacagtg | 1140 |
| gagaccgtcg tcttgcacag catgcccatc cccaaagccg atgaaggcag ataa | 1194 |

<210> SEQ ID NO 11
<211> LENGTH: 1185
<212> TYPE: DNA
<213> ORGANISM: Artificial Sequence
<220> FEATURE:
<223> OTHER INFORMATION: Synthetic polynucleotide

<400> SEQUENCE: 11

| | |
|---|---|
| atgtcgaaga tggtggagga gcattgggca gcgcagcggg cgaggggacc ggcgacagtg | 60 |
| ctggccatcg gcactgcaaa tcctcccaat gtgttgtacc aggcagatta tcccgacttc | 120 |
| tactttaggg tcaccaagag tgagcacatg acccagctaa aggagaagtt taaacgtata | 180 |
| tgtgataagt cagcaataag aaagcgccac ctccatctaa ccgaggagct gctggagaag | 240 |
| aaccctaaca tatgtgcaca catggccccc tccctcgacg cccggcaaga cattgcggtg | 300 |
| gtggaggtcc ccaagctagc caaagaagct gcaaccaagg ccatcaagga gtggggcga | 360 |
| cccaagtccg acatcaccca cctcatcttc tgcaccacct gcggcgtgga catgcccggc | 420 |
| gccgactacc aactcaccac gctcctcggc ctccgcccca cggtccgccg caccatgctc | 480 |
| taccaacagg gctgcttcgc cggcggcaca gtccttcgcc atgccaagga cttcgccgag | 540 |
| aacaatagg gtgctcgtgt cctcgccgtc tgctcggagt tcaccgtcat gaacttcagc | 600 |
| ggaccgtcgg aggcccactt agacagcatg gtcggtatgg cgctgttcgg tgatggcgcc | 660 |
| tcggctgtca tcgtcggcgc cgatcctgac tttgccattg aacgaccgct ctttcaactg | 720 |
| gtttctacaa cacaaactat tgtcccggac tcggacggag ccatcaagtg ccatctcaag | 780 |
| gaggtgggcc taaccctgca tctcgttaag aatgtaccag atctcatatc aaataacatg | 840 |
| gacaagatcc tcgaagaggc atttgcacca ttgggcatca gagattggaa ctcaatcttt | 900 |
| tggacagctc atccaggtgg agcagccata ctcgaccagt tggaggccaa gctcggtctg | 960 |
| aacaaggaga agctcaagac tacaagaaca gttctgaggg agtatggaaa catgtccagc | 1020 |
| gcctgtgttt gtttcgtcct ggacgagatg aggagaagta gctggagga ggggaagaca | 1080 |
| acgtccgggg aagggttgga atggggaatt ctgctagggt ttgggcctgg gttgacagtg | 1140 |
| gagacagtcg tcttgcgtag cgtacccatc tcgacagcca attaa | 1185 |

<210> SEQ ID NO 12

<211> LENGTH: 1185
<212> TYPE: DNA
<213> ORGANISM: Artificial Sequence
<220> FEATURE:
<223> OTHER INFORMATION: Synthetic polynucleotide

<400> SEQUENCE: 12

| | | | | | |
|---|---|---|---|---|---|
| atgtcgaaga | ccgtagagga | gatttgggcg | gcgcagcggg | cgaggggacc | agccacggtg | 60 |
| ctggccatcg | gcactgctgc | gccggccaat | gtggtgtacc | aggccgatta | tccggactac | 120 |
| tactttagga | tcaccaagag | cgagcacatg | acagagctca | aggagaagtt | ccgacgaatg | 180 |
| tgtgacaagt | cgatgataac | gaagcggcac | atgcacttgt | cggaggagct | gttgaaaaac | 240 |
| aaccctgaca | tctgtgccta | catggcccct | tccctcgacg | cccgccaaga | tatggtcgtg | 300 |
| gtggaggtac | ccaagctcgg | caaggaggcg | ccgccaagg | ccatcaagga | atggggccgc | 360 |
| ccaaagtcgg | ccatcaccca | cctcatcttc | tgcaccacct | ccggcgtcga | catgcccggc | 420 |
| gccgatttcc | agctcaccaa | gctactcggc | ctctgcccct | ccgttcgccg | caccatgctc | 480 |
| taccagcagg | gctgcttcgc | cggcggtacg | gttctccgcc | ttgccaagga | cctcgccgag | 540 |
| aacaatgcgg | gcgcgagggt | cctcgtcgtc | tgctccgaga | tcaccgccgt | caccttccgc | 600 |
| ggcccctcgg | agactcacct | cgatagcatg | gtcggccagg | ccctgttcgg | tgatggtgcc | 660 |
| tctgccatca | tcgtcggtgc | cgaccccgac | cccgtcatag | aaaggccact | ctttcaaatt | 720 |
| gtatctgcgg | ctcagaccat | ccttcccgac | tcggatgggg | caatagacgg | ccatctccga | 780 |
| gaagtgggtc | taaccttcca | cctcctcaag | gacgtacctg | gctcatctc | aaagaacatc | 840 |
| gagaagagcc | taaggaggc | gtttgcaccg | ctgggcatcg | acgactggaa | ctcgatattt | 900 |
| tggattgttc | atccaggcgg | gccggccatt | ctagaccagg | tggaggcgaa | gctgcgtctg | 960 |
| aaagtggaga | agctgaagac | aacgagaaca | gttttgagtg | agtacgggaa | tatgtcgagc | 1020 |
| gcttgcgtgt | tgttcatact | tgacgagatg | aggaggaaca | gcatggaaga | agggaaggcg | 1080 |
| acgaccggtg | aagggttaca | ttggggagtt | ttgtttggtt | ttgggccggg | cttgacagtg | 1140 |
| gagacggtcg | tcttgcatag | tttgcccatc | gccgaggcca | actaa | | 1185 |

<210> SEQ ID NO 13
<211> LENGTH: 1086
<212> TYPE: DNA
<213> ORGANISM: Artificial Sequence
<220> FEATURE:
<223> OTHER INFORMATION: Synthetic polynucleotide

<400> SEQUENCE: 13

| | | | | | |
|---|---|---|---|---|---|
| atggagcaag | ctgtgttcaa | agaccaatcc | ccaagcaggg | atgatattga | tgaagagctc | 60 |
| tttcaatctg | ctctatatct | tagcactgcg | gttgtcaccg | tgccggcggc | aatcatggct | 120 |
| gcaaatgacc | ttgacgtgct | gcagataatt | gccaaagctg | gcccaggtgc | tcacctatct | 180 |
| ccgacagaga | ttgtcagcca | ccttcccacc | cgtaacccta | tgccgcggc | ggcgcttcac | 240 |
| cggatactcc | gagtactagc | cagccactcc | atccttgaat | gctcgtcgag | atgcgagggc | 300 |
| gaggcaaaat | atggattaag | gccggtgtgc | aagttctttc | tcaatgataa | ggatggtgtc | 360 |
| tccttgaatg | ccatgccatc | cttcgttcaa | agtagagttt | ttatagatag | ctggcaatat | 420 |
| atgaaagatg | ctgttcttga | gggggtagtc | ccctttgaga | aagcctatgg | tatgcctttt | 480 |
| tatcagtttc | aagcagtgaa | caccaaattc | aaagaaacct | tcgccaaagc | catggctgct | 540 |
| cactcaactt | tggtagtaaa | aaagatgctt | gacacataca | atgggtttga | gggactcact | 600 |
| gagttgatgg | atgttgctgg | tggaaccggt | tccaccctca | acctcattgt | ctccaaatac | 660 |

```
ccacaaatca aaggcacaaa ctttgatctc aaacatgtca ttgaggccgc accaaactac    720
cctggggtga agcatttgag tggggacatg tttgatagca ttccaagtgc aaagaacatt    780
attatgaagt ggatactaca taattggagc gacgagcact gtgtaaaact cctcaagaac    840
tgctacactt ccttaccaga atttgggaag ttgattgtgg ttgattccat tgtgggtgag    900
gatgttgatg ctggtttgac gacaacaaat gtctttggat gcgacttcac aatgctaact    960
ttcttcccca atgcaaaaga gaggacccgt gaagaattcc aagacctggc caaagctagt   1020
ggcttctcaa cgttcaaacc gatctgctgc gcctatggcg tgtgggttat ggaatttcac   1080
aaataa                                                              1086

<210> SEQ ID NO 14
<211> LENGTH: 1083
<212> TYPE: DNA
<213> ORGANISM: Artificial Sequence
<220> FEATURE:
<223> OTHER INFORMATION: Synthetic polynucleotide

<400> SEQUENCE: 14
atgaatgatc aagagttgca tggatactca caaaatgctc aacctcagct atggaacctc     60
ctgttgagct tcataaattc catgtccctt aagtgtgcag tggagttggg catcccccgat   120 ataatacata gccatgccca acaccaatc aacataaccg accttgctgc ctccataccc    180
attcccccaa acaaaacaag ccaattccgc cgactcatgc gcctcctggt tcactccaac    240
gtcttttccg tccataaacg tgaggatggt gatgaggggt tcctcctaac tcctatgtcc    300
aggatccttg tcacgtcgaa cgacaataat ggaggtaact tgtcacccct tgtttccatg    360
atggttgatc cgtccctggt gtctccatgg cacttccttg tcaatggct caaaggcaat    420 gacacccaag gcacaccatt tcgcatgtgc catggtgaag aaatgtggga ctgggccaac    480
aagtacccgg acttcaacaa gaagttcaac atggcgatgg tctgtgacag ccagtattta    540
atgaaaatta ttgtgaagaa gtgcgccact gcctttgaag gcaagaggtc cctgattgac    600
gtcggtggcg ggactggtgg cgccgcacgg tctattgccg aagcatttcc agacatacag    660
gaggtgtctg tattggatct tcctcatgtg gttgcaggtt tgcccaatga ctcgagggtg    720
aagtttgttg gaggagacat gttccacacc atccctcccg ctgatgttgt cttattgaag    780 gcgattttc atggttggaa tgatgaggag tgcatcaaga tattgaagaa ctgcaagaag    840
gcaattccaa gcaaggaaga gggaggcaag gtgatgatat tggacatggt ggtcaattcc    900 gccccggggtg accatatgat tacagaagat caatatttta tggatttgat gatgataacc    960
tacgcaagag gattggagag agacgagaat gaatggaaga agctgtttaa agatgcaggt   1020
ttcacatcgt acaagatcac ccacgggctt ggaacgagtt cgcttatcga gctctaccct   1080
tag                                                                 1083

<210> SEQ ID NO 15
<211> LENGTH: 1536
<212> TYPE: DNA
<213> ORGANISM: Artificial Sequence
<220> FEATURE:
<223> OTHER INFORMATION: Synthetic polynucleotide

<400> SEQUENCE: 15
atggagcaag ctcaatgggt cgacccaact ctgctccctg catttgtggg catcatcttc     60
ttcttccttg gcatgttctt tggaaggagt tctttgggag ctgggaaggg tgcagcgcct    120
```

| | |
|---|---:|
| agaagcacca gttctaccga gtggccagac ggccctccaa agctgcccat catcggcaac | 180 |
| ctgcaccagc tcaacaaagg cggggagctg gtccaccaca acctgccaa gctcgcccag | 240 |
| tcctacgacc gcgccatgac catctgggtc ggcagctggg gccccatgat cgtcgtcagc | 300 |
| gacgccgacc ttgcatggga ggtcctcgtc accaagtcgc cggacttcgc cggccgggtg | 360 |
| ctctccaagc tctcgcactt gttcaacgcc aactacaaca ccgtcgtcgc ctacgacgcc | 420 |
| gggccgcaat ggcagtcgct ccggcgaggt ctgcagcacg gccgctcgg ccccgcccat | 480 |
| gtttctgcgc aggctcgttt ccacgaagaa gacatgaagc tcctggtgag cgacatgatg | 540 |
| agagcagcac agaaaggtgg tagcaatgga gtggttgaac ctctggccta tgtccggcga | 600 |
| gccactatcc gatttctgtc tcgtctatgc tttggggagg ccttcaacga cgaggcgttc | 660 |
| gtggagggga tggacgaagc agtggaggag accatcggag ccactggcca tgcacgcatc | 720 |
| ctcgacgcct tctacttcac tcgccacctc cctatcatcc gccgcagctt catagatacc | 780 |
| gtcaacgcca agaagaagat cgagagcctt gtccggccgt tgctctcccg gccggcgcca | 840 |
| ccggggtctt acctccactt cctccttttcc accgacgcgc cggagaatat gatcatcttt | 900 |
| cgaatattcg aagtctactt gctgggcgtg gacagcaccg cctccaccac cacatgggct | 960 |
| ctcgccttcc tcgtctccaa ccaacaggcg caggagaagc tccacaatga gctcgcccag | 1020 |
| tactgcgcca gccagaacaa tcagatcatc aaagcagacg acgtcggaaa gctgtcgtac | 1080 |
| ctgctcgggg tagtgaagga gacgatgagg atgaagccga tagcgccgct ggccgtcccc | 1140 |
| cacaagacgc tcaaggagac gatgctcgac ggaaagaggg tggcggcggg aacgacggtg | 1200 |
| gtagtgaacc tctatgccgt ccactacaac ccgaagctat ggccggagcc ggagcagttc | 1260 |
| cgcccggaga ggttcgtggt cggcgccagc ggcggcaatg gtgggggggtc ttccgagtac | 1320 |
| atgctgcagt cgtacctgcc ctttggaggg gggatgaggg cctgcgcagg gatggaggtg | 1380 |
| ggaaagttgc aggtggcgat ggtcgtggcc aaccttgtga tggcatttaa atggttgccg | 1440 |
| gaggaggagg ggaagatgcc ggaccctggct gaagacatga ccttcgtgct catgatgaag | 1500 |
| aagccattgg ctgccaaaat cgttccacgt gcatga | 1536 |

<210> SEQ ID NO 16
<211> LENGTH: 981
<212> TYPE: DNA
<213> ORGANISM: Artificial Sequence
<220> FEATURE:
<223> OTHER INFORMATION: Synthetic polynucleotide

<400> SEQUENCE: 16

| | |
|---|---:|
| atggagactg agaggaagtc caggatctgt gtcaccgggg caggaggctt tgtagcctct | 60 |
| tgggtcgtca agcttttcct ctccaaaggt tatcttgtcc atggcactgt cagagacctc | 120 |
| ggagaagaga agactgccca tttgaggaag ttggagggtg cgtaccataa tctgcagctg | 180 |
| ttcaaggctg acttgttgga ttatgagtcc ttgctcgggg ccattactgg ctgcgatgga | 240 |
| gttctccatg ttgcaactcc tgttccttcg agtaaaactg cttattccgg aactgagttg | 300 |
| gtcaagactg ctgtgaatgg aactctgaat gtgctcaggg catgtacaga ggcaaaagtg | 360 |
| aaaaaggtca tctatgtttc atctactgcc gctgttttgg tgaatcctaa tttacccaag | 420 |
| gataaaatcc cggacgaaga ttgttggaca gacgaagagt actgcaggac aactccgttc | 480 |
| ttcctgaatt ggtattgcat cgccaaaaca gcagccgaaa agaatgcctt ggaatatgga | 540 |
| gataagaaag ggatcaacgt tatatctatt tgcccttcat acatctttgg acctatgctt | 600 |
| caaccgacaa ttaattcaag caacttggaa ttgttgaggc taatgaaagg agatgacgaa | 660 |

```
agcatagaaa acaaatttct gctgatggtg gatgtgcgag atgttgctga agcaatttta    720
ctattatatg agaagcaaga aacatcaggg agatacattt cttcgccgca tggtatgcga    780
caaagcaact tggttgagaa gctggagagc ctgcagccgg gctacaatta tcataagaac    840
tttgtggata ttaaacctag ttggacaatg atcagctcag aaaagctcaa gaaacttggt    900
tggaaaccta gaccacttga ggacactatt tctgaaacag tgctgtgttt tgaagagcat    960
ggtttgctgg aaaatgaata g                                              981
```

ENZYMATIC SYNTHESIS OF KAVALACTONES AND FLAVOKAVAINS

RELATED APPLICATIONS

This application is a division of U.S. application Ser. No. 16/249,758, filed Jan. 16, 2019, which claims priority under 35 U.S.C. § 119(e) to U.S. Provisional Application No. 62/618,549, filed Jan. 17, 2018, each of which is incorporated by reference herein in its entirety.

GOVERNMENT SUPPORT

This invention was made with government support under grant number 1709616 awarded by the National Science Foundation. The government has certain rights in the invention.

BACKGROUND OF THE INVENTION

Kava or kava-kava (*Piper methysticum*) is a domesticated tropical shrub native to Oceania, where its roots are used to prepare a beverage for medicinal and ceremonial purposes.[1,2] A substantial body of scientific evidence supports positive effects of kava in generalized anxiety disorder,[3] insomnia,[4] and other non-psychotic psychological and neurological disorders[5]. The main bioactive components of kava, called kavalactones (FIG. 1), are known to interact with the human nervous system via $GABA_A$, cannabinoid ($CB_1$), and other molecular receptors.[6,8] Kava-kava is also known to contain several chalconoids called flavokavains (FIG. 2), which show promising anti-cancer activities against various cell lines including colon, bladder, and breast cancer.[9] Therefore, there exists a need for ways to prepare kavalactones and flavokavains for research and medicinal purposes.

SUMMARY OF THE INVENTION

Kavalactones, small hydrophobic polyketides, and flavokavains, chalconoids, are the bioactive ingredients found in the kava drink that is widely commercially available in the form of a dried kava-kava root powder. Despite a long tradition of kava consumption in its native Oceania, it occupies only a niche market in the Western society, likely due to the unpleasant taste of the kava drink. Since scientific literature has already established therapeutic and anxiolytic properties of kava, there is a potential to employ kavalactones as standalone supplements or as additives to various food products. Importantly, the effect on the human brain caused by kava consumption tends to be mild, and kava consumption is non-addictive.

Kavalactone structure is based on a styrylpyrone backbone decorated with various hydroxy and/or methoxy modifications. At least twenty different kavalactone structures are known, although six kavalactones are considered major ones, as together they constitute over 90% of the kavalactone content in the kava kava shrub. The biosynthetic pathway of kavalactones and flavokavains branches off the general phenylpropanoid pathway, utilizing coenzyme A (CoA) esters of cinnamic acids and malonyl-CoA as substrates for a type III polyketide synthase, which forms the structure backbone (FIG. 3). In the case of flavokavains, the chalcone backbone is produced in kava-kava by the chalcone synthase PmCHS. In the case of kavalactones, the corresponding 6-styryl-4-hydroxy-2-pyrone backbone is produced by one of two styrylpyrone synthases, PmSPS1 or PmSPS2. The backbones are further modified by decorating enzymes to produce individual kavalactones or flavokavains.

In the present disclosure, the elucidated native kavalactone biosynthetic pathway from *Piper methysticum* allows for the use of metabolic engineering to produce kavalactones and flavokavains through expression in heterologous hosts. Described herein are the methods, compounds, reagents, and systems constituting a bioengineering approach to sustainable production of kavalactones and flavokavains.

In one aspect, the present disclosure provides methods to produce kavalactones, flavokavains, and biosynthetic intermediates of kavalactones and flavokavains using enzymes at least 80% identical to naturally occurring enzymes of the kavalactone and flavokavain biosynthetic pathways.

In certain embodiments, methods are provided for the production of CoA esters of Formula (II) from carboxylic acids of Formula (I), or a salt thereof, and coenzyme A (CoA) using an enzyme that is at least 80% identical to Pm4CL1 (SEQ ID NO: 1). The structures of Formula (I) and Formula (III are as follows:

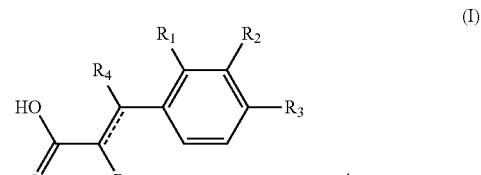

and

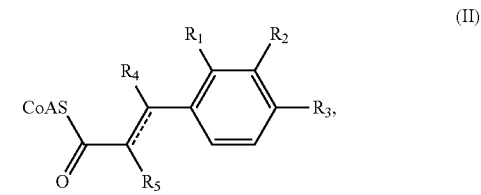

wherein: $=\!=\!=$ is a single bond or a double bond; each of $R_1$, $R_2$, and $R_3$ independently is hydrogen, optionally substituted, cyclic or acyclic aliphatic, or $OR_x$, wherein $R_x$ is hydrogen or optionally substituted, cyclic or acyclic aliphatic; and each of $R_4$ and $R_5$ independently is hydrogen or optionally substituted, cyclic or acyclic aliphatic.

In certain embodiments, methods are provided for the production of compounds containing the kavalactone backbone (6-styryl-4-hydroxyl-2-pyrone) of Formula (III) from CoA esters of Formula (II), or a salt thereof, and malonyl-CoA using an enzyme that is at least 80% identical to PmSPS1 (SEQ ID NO: 2) or an enzyme that is at least 80% identical to PmSPS2 (SEQ ID NO: 3). The structures of Formula (II) and Formula (III) is as follows:

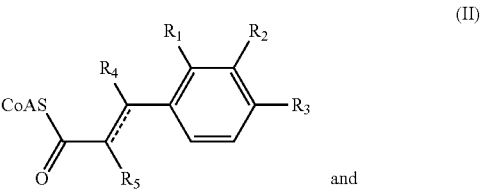

and

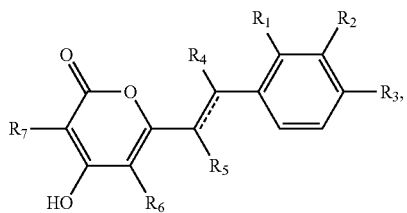

(III)

wherein: --- is a single bond or a double bond; each of $R_1$, $R_2$, $R_3$, $R_6$, and $R_7$ independently is hydrogen, optionally substituted, cyclic or acyclic aliphatic, or $OR_x$, or $R_1$ and $R_2$ are optionally combined to form a ring, or $R_2$ and $R_3$ are optionally combined to form a ring, wherein $R_x$ is hydrogen or optionally substituted, cyclic or acyclic aliphatic; and each of $R_4$ and $R_5$ independently is hydrogen or optionally substituted, cyclic or acyclic aliphatic.

In certain embodiments, methods are provided for the production of methylated 6-styryl-4-hydroxyl-2-pyrone compounds of Formula (IV) from compounds containing the kavalactone backbone (6-styryl-4-hydroxyl-2-pyrone) of Formula (III), or a salt thereof, and S-adenosylmethionine using an enzyme that is at least 80% identical to PmOMT4 (SEQ ID NO: 5) or an enzyme that is at least 80% identical to PmOMT1 (SEQ ID NO: 6). The structures of Formula (III) and Formula (IV) are as follows:

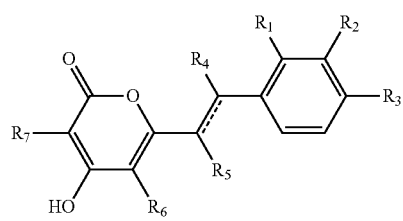

(III)

and

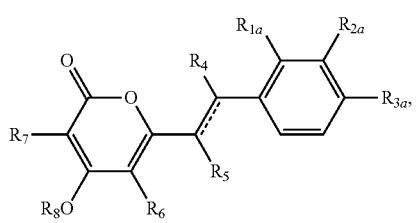

(IV)

wherein: --- is a single bond or a double bond; each of $R_1$, $R_2$, $R_3$, $R_{1a}$, $R_{2a}$, $R_{3a}$, $R_6$, and $R_7$ independently is hydrogen, optionally substituted, cyclic or acyclic aliphatic, or $OR_x$, or $R_1$ and $R_2$ are optionally combined to form a ring, or $R_2$ and $R_3$ are optionally combined to form a ring, or $R_{1a}$ and $R_{2a}$ are optionally combined to form a ring, or $R_{2a}$ and $R_{3a}$ are optionally combined to form a ring, wherein $R_x$ is hydrogen or optionally substituted, cyclic or acyclic aliphatic; each of $R_4$ and $R_5$ independently is hydrogen or optionally substituted, cyclic or acyclic aliphatic; and $R_8$ is optionally substituted, cyclic or acyclic aliphatic.

In certain embodiments, methods are provided for the production of 6-styryl-4-hydroxyl-5,6-dihydro-2-pyrone compounds of Formula (V) from 6-styryl-4-hydroxyl-2-pyrone compounds of Formula (IV), or a salt thereof, and a reducing agent (i.e., NADPH or NADH) using an enzyme that is at least 80% identical to PmRDCT10 (SEQ ID NO: 8). The structures of Formula (IV) and Formula (V) are as follows:

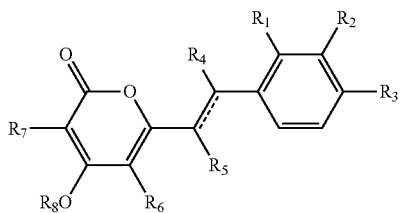

(IV)

and

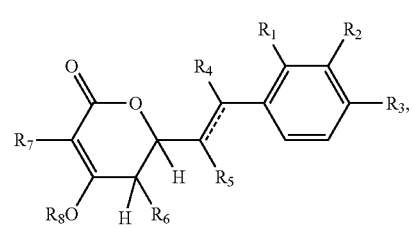

(V)

wherein: --- is a single bond or a double bond; each of $R_1$, $R_2$, $R_3$, $R_6$, and $R_7$ independently is hydrogen, optionally substituted, cyclic or acyclic aliphatic, or $OR_x$, or $R_1$ and $R_2$ are optionally combined to form a ring, or $R_2$ and $R_3$ are optionally combined to form a ring, wherein $R_x$ is hydrogen or optionally substituted, cyclic or acyclic aliphatic; each of $R_4$ and $R_5$ independently is hydrogen or optionally substituted, cyclic or acyclic aliphatic; and $R_8$ is optionally substituted, cyclic or acyclic aliphatic.

In certain embodiments, methods are provided for the production of 6-styryl-4-hydroxyl-2-pyrone compounds containing a methylenedioxy bridge of Formula (VI) from 6-styryl-4-hydroxyl-2-pyrone compounds of Formula (IV), or salt thereof, and a reducing agent (i.e., NADPH or NADH) using an enzyme that is at least 80% identical to PmMDB1 (SEQ ID NO: 7). The structures of Formula (IV) and Formula (VI) are as follows:

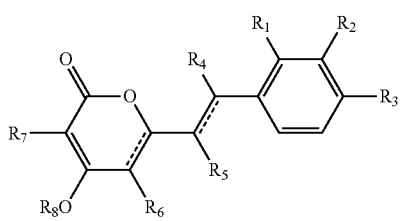

(IV)

and

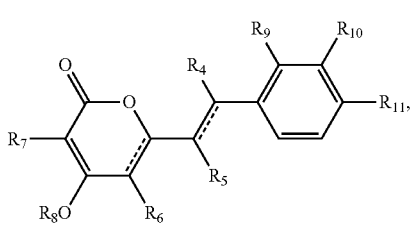

(VI)

wherein: --- a single bond or a double bond; each of $R_1$, $R_2$, $R_3$, $R_6$, $R_7$, $R_9$, $R_{10}$, and $R_{11}$ independently is hydrogen, optionally substituted, cyclic or acyclic aliphatic, or $OR_x$, or $R_1$ and $R_2$ are combined to form a ring, or $R_2$ and $R_3$ are combined to form a ring, $R_9$ and $R_{10}$ are combined to form a ring, or $R_{10}$ and $R_{11}$ are combined to form a ring, wherein $R_x$ is hydrogen or optionally substituted, cyclic or acyclic aliphatic; each of $R_4$ and $R_5$ independently is hydrogen or optionally substituted, cyclic or acyclic aliphatic; and $R_8$ is optionally substituted, cyclic or acyclic aliphatic; provided that at least one of $R_1$, $R_2$, or $R_3$ is —OH, at least one of $R_1$, $R_2$, or $R_3$ is —OMe, and $R_9$ and $R_{10}$ or $R_{10}$ and $R_{11}$ are combined to form a methylenedioxy cyclic moiety —OCH$_2$O—.

In certain embodiments, methods are provided for the production of compounds containing the chalcone backbone of Formula (VII) from CoA esters of Formula (II), or a salt thereof, and malonyl-CoA using an enzyme that is at least 80% identical to PmCHS (SEQ ED NO: 4). The structures of Formula (II) and Formula (VII) are as follows:

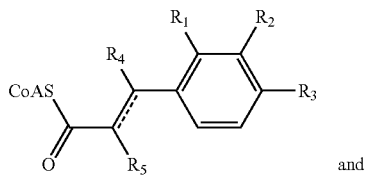
(II)

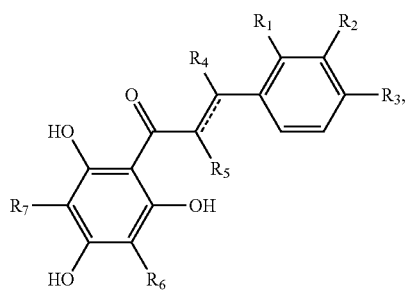
(VII)

wherein: === is a single bond or a double bond; and each of $R_1$, $R_2$, $R_3$ $R_6$, and $R_7$ independently is hydrogen, optionally substituted, cyclic or acyclic aliphatic, or $OR_x$, wherein $R_x$ is hydrogen or optionally substituted, cyclic or acyclic aliphatic; and each of $R_4$ and $R_5$ independently is hydrogen or optionally substituted, cyclic or acyclic aliphatic.

In certain embodiments, methods are provided for the production of methylated chalcone compounds of Formula (VIII) from compounds containing the chalcone backbone of Formula (VII), or a salt thereof, and S-adenosylmethionine using an enzyme that is at least 80% identical to PmOMT4 (SEQ ID NO: 5) or an enzyme that is at least 80% identical to PmOMT1 (SEQ ID NO: 6). The structures of Formula (VII) and Formula (VIII) are as follows:

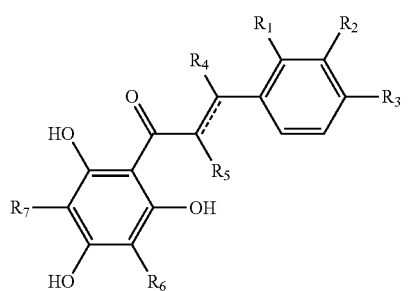
(VII)

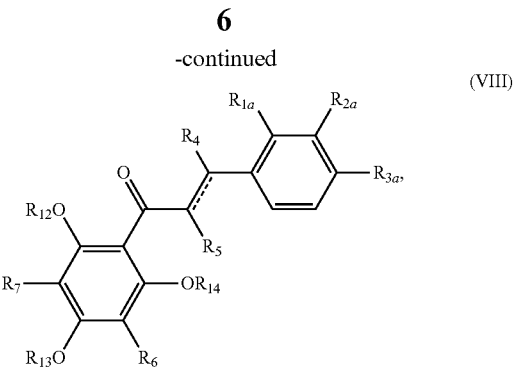
(VIII)

wherein: === is a single bond or a double bond; and each of $R_1$, $R_2$, $R_3$, $R_{1a}$, $R_{2a}$, $R_{3a}$, $R_6$, and $R_7$ independently is hydrogen, optionally substituted, cyclic or acyclic aliphatic, or $OR_x$, wherein $R_x$ is hydrogen or optionally substituted, cyclic or acyclic aliphatic; each of $R_4$ and $R_5$ independently is hydrogen or optionally substituted, cyclic or acyclic aliphatic; each of $R_{12}$ and $R_{13}$ independently is optionally substituted, cyclic or acyclic aliphatic; and $R_{14}$ is hydrogen.

In another aspect, the present disclosure provides recombinant nucleic acids encoding for the enzymes described herein (e.g., 4-coumarate-CoA ligase Pm4CL1 or an enzyme that is at least 80% identical to SEQ ID NO: 1, styrylpyrone synthase PmSPS1 or an enzyme that is at least 80% identical to SEQ ID NO: 2, styrylpyrone synthase PmSPS2 or an enzyme that is at least 80% identical to SEQ ID NO: 3, chalcone synthase PmCHS or an enzyme that is at least 80% identical to SEQ ID NO: 4, methyltransferase PmOMT4 or an enzyme that is at least 80% identical to SEQ ID NO: 5, methyltransferase PmOMT1 or an enzyme that is at least 80% identical to SEQ ID NO: 6, cytochrome P450 enzyme PmMDB1 or an enzyme that is at least 80% identical to SEQ ID NO: 7, and NADPH-dependent reductase PmRDCT10 or an enzyme that is at least 80% identical to SEQ ID NO: 8). In certain embodiments, the recombinant nucleic acids are complementary DNA (cDNA) molecules. The cDNA molecules may be contained in vectors. These vectors may be transferred into host cells or organisms including, but not limited to, bacteria, yeast, and plants. In certain embodiments, the host is a bacterium and is a wildtype, mutant, recombinant, or genetically engineered form of *Escherichia coli*. In certain embodiments, the host is a yeast and is a wildtype, mutant, recombinant, or genetically engineered form of *Saccharomyces cerevisiae*. In certain embodiments, the host is a plant is a wildtype, mutant, recombinant, or genetically engineered form of *Nicotiana benthamiana*.

The details of certain embodiments of the invention are set forth in the Detailed Description of Certain Embodiments, as described below. Other features, objects, and advantages of the invention will be apparent from the Definitions, Examples, Figures, and Claims.

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's*

*Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al, Tetrahedron 33:2725 (1977); Eliel, E. L. *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⁓ is a single bond where the stereochemistry of the moieties immediately attached thereto is not specified, --- is absent or a single bond, and ═ or ⁼⁼⁼ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of a carbon by a $^{13}$C- or $^{14}$C-enriched carbon are within the scope of the disclosure. Such compounds are useful, for example, as analytical tools or probes in biological assays.

When a range of values is listed, it is intended to encompass each value and subrange within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., —$CH_2F$, —$CHF_2$, —$CF_3$ or benzyl (Bn)).

The term "haloalkyl" is a substituted alkyl group, wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted C$_{2-10}$ alkenyl. In certain embodiments, the alkenyl group is a substituted C$_{2-10}$ alkenyl. In an alkenyl group, a C=C double bond for which the stereochemistry is not specified (e.g., —CH=CHCH$_3$,

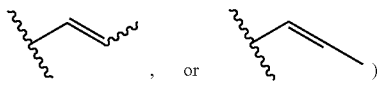

may be in the (E)- or (Z)-configuration.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("heteroC$_{2-10}$ alkenyl"). In some embodiments, a heteroalkenyl group has 2 to 9 carbon atoms at least one double bond, and 1 or more heteroatoms within the parent chain ("heteroC$_{2-9}$ alkenyl"). In some embodiments, a heteroalkenyl group has 2 to 8 carbon atoms, at least one double bond, and 1 or more heteroatoms within the parent chain ("heteroC$_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted C$_{3-14}$ carbocyclyl. In certain embodiments, the carbocyclyl group is a substituted C$_{3-14}$ carbocyclyl.

In some embodiments, "carbocyclyl" is a monocyclic, saturated carbocyclyl group having from 3 to 14 ring carbon atoms ("C$_{3-14}$ cycloalkyl"). In some embodiments, a cycloalkyl group has 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 4 to 6 ring carbon atoms ("C$_{4-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-4}$ cycloalkyl. In certain embodiments, the cycloalkyl group is a substituted C$_{3-14}$ cycloalkyl. In certain embodiments, the carbocyclyl includes 0, 1, or 2 C=C double bonds in the carbocyclic ring system, as valency permits.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14% electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 n electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

The term "unsaturated bond" refers to a double or triple bond.

The term "unsaturated" or "partially unsaturated" refers to a moiety that includes at least one double or triple bond.

The term "saturated" refers to a moiety that does not contain a double or triple bond, i.e., the moiety only contains single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)O$R^{aa}$, =NN$R^{bb}$S(=O)$_2$$R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2$$R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3$$^+$X$^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)$_2$$R^{ee}$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$alkenyl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, hetero$C_{1-6}$alkyl, hetero$C_{2-6}$alkenyl, hetero$C_{2-6}$alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

In certain embodiments, the carbon atom substituents are independently halogen, substituted or unsubstituted C$_{1-6}$ alkyl, —O$R^{aa}$, —S$R^{aa}$, —N($R^{bb}$)$_2$, —CN, —SCN, —NO$_2$, —C(=O)$R^{aa}$, —CO$_2$$R^{aa}$, —C(=O)N($R^{bb}$)$_2$, —OC(=O) $R^{aa}$, —OCO$_2$$R^{aa}$, —OC(=O)N($R^{bb}$)$_2$, —N$R^{bb}$C(=O)$R^{aa}$, —N$R^{bb}$CO$_2$$R^{aa}$, or —N$R^{bb}$C(=O)N($R^{bb}$)$_2$. In certain embodiments, the carbon atom substituents are independently halogen, substituted or unsubstituted C$_{1-6}$ alkyl, —O$R^{aa}$, —S$R^{aa}$, —N($R^{bb}$)$_2$, —CN, —SCN, or —NO$_2$.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —O$R^{aa}$, —ON($R^{bb}$)$_2$, —OC(=O) S$R^{aa}$, —OC(=O)$R^{aa}$, —OCO$_2$$R^{aa}$, —OC(=O)N($R^{bb}$)$_2$, —OC(=N$R^{bb}$)$R^{aa}$, —OC(=N$R^{bb}$)O$R^{aa}$, —OC(=N$R^{bb}$)N ($R^{bb}$)$_2$, —OS(=O)$R^{aa}$, —OSO$_2$$R^{aa}$, —OSi($R^{aa}$)$_3$, —OP ($R^{cc}$)$_2$, —OP($R^{cc}$)$_3$, —OP(=O)$_2$$R^{aa}$, —OP(=O)($R^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$, wherein R$^{bb}$ and X$^-$ are as defined herein.

The term "sulfonyl" refers to a group selected from —SO$_2$N(R$^{bb}$)$_2$, —SO$_2$R$^{aa}$ and —SO$_2$OR$^{aa}$ wherein R$^{aa}$ and R$^{bb}$ are as defined herein.

The term "sulfinyl" refers to the group —S(=O)R$^{aa}$, wherein R$^{aa}$ is as defined herein.

The term "carbonyl" refers a group wherein the carbon directly attached to the parent molecule is sp$^2$ hybridized, and is substituted with an oxygen, nitrogen or sulfur atom, e.g., a group selected from ketones (—C(=O)R$^{aa}$), carboxylic acids (—CO$_2$H), aldehydes (—CHO), esters (—CO$_2$R$^{aa}$, —C(=O)SR$^{aa}$, —C(=S)SR$^{aa}$), amides (—C(=O)N(R$^{bb}$)$_2$, —C(=O)NR$^{bb}$SO$_2$R$^{aa}$, —C(=S)N(R$^{bb}$)$_2$), and imines (—C(=NR$^{bb}$)R$^{aa}$, —C(=NR$^{bb}$)OR$^{aa}$, —C(=NR$^{bb}$)N(R$^{bb}$)$_2$), wherein R$^{aa}$ and R$^{bb}$ are as defined herein.

The term "silyl" refers to the group —Si(R$^{aa}$)$_3$, wherein R$^{aa}$ is as defined herein.

The term "phosphoramido" refers to the group —O(P=O)(NR$^{bb}$)$_2$, wherein each R$^{bb}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, 5-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(MN-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-f-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N',N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentaacylchromium- or tungsten) acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), r-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, r-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), f-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, 5-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxyaryl) benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

The term "heteroatom" refers to an atom that is not hydrogen or carbon. In certain embodiments, the heteroatom is nitrogen. In certain embodiments, the heteroatom is oxygen. In certain embodiments, the heteroatom is sulfur.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methanesulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4]^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "administer," "administering," or "administration" refers to implanting, absorbing, ingesting, injecting, inhaling, or otherwise introducing a compound or cell described herein or generated as described herein, or a composition thereof, in or on a subject.

The terms "treatment," "treat," and "treating" refer to reversing, alleviating, delaying the onset of, or inhibiting the progress of a disease. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen and/or in light of detecting that the subject has a genotype associated with the disease). Treatment may also be continued after symptoms have resolved, for example, to delay or prevent recurrence.

The terms "condition," "disease," and "disorder" are used interchangeably.

As used herein, the term "salt" refers to any and all salts, and encompasses pharmaceutically acceptable salts.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "inhibition," "inhibiting," "inhibit," or "inhibitor" refers to the ability of a compound to reduce, slow, halt or prevent activity of a particular biological process (e.g., kinase activity) in a cell.

The term "gene" refers to a nucleic acid fragment that provides a template that can be used for producing a gene product. In certain embodiments, the nucleic acid fragment includes regulatory sequences preceding and following the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

The term "gene product" (also referred to herein as "gene expression product" or "expression product") encompasses products resulting from expression of a gene, such as RNA transcribed from a gene and polypeptides arising from translation of such RNA. It will be appreciated that certain gene products may undergo processing or modification, e.g., in a cell. For example, RNA transcripts may be spliced, polyadenylated, etc., prior to mRNA translation, and/or polypeptides may undergo co-translational or post-translational processing such as removal of secretion signal sequences, removal of organelle targeting sequences, or modifications such as phosphorylation, fatty acylation, etc. The term "gene product" encompasses such processed or modified forms. Genomic, mRNA, polypeptide sequences from a variety of species, including human, are known in the art and are available in publicly accessible databases such as those available at the National Center for Biotechnology Information (www.ncbi.nih.gov) or Universal Protein Resource (www.uniprot.org). Databases include, e.g., GenBank, RefSeq, Gene, UniProtKB/SwissProt, UniProtKB/Trembl, and the like. In general, sequences, e.g., mRNA and polypeptide sequences, in the NCBI Reference Sequence database may be used as gene product sequences for a gene of interest. It will be appreciated that multiple alleles of a gene may exist among individuals of the same species. For example, differences in one or more nucleotides (e.g., up to about 1%, 2%, 3-5% of the nucleotides) of the nucleic acids encoding a particular protein may exist among individuals of a given species. Due to the degeneracy of the genetic code, such variations often do not alter the encoded amino acid sequence, although DNA polymorphisms that lead to changes in the sequence of the encoded proteins can exist. Examples of polymorphic variants can be found in, e.g., the Single Nucleotide Polymorphism Database (dbSNP), available at the NCBI website at www.ncbi.nlm.nih.gov/projects/SNP/. (Sherry S T, et al. (2001). "dbSNP: the NCBI database of genetic variation". Nucleic Acids Res. 29 (1): 308-311; Kitts A, and Sherry S, (2009). The single nucleotide polymorphism database (dbSNP) of nucleotide sequence variation in The NCBI Handbook [Internet]. McEntyre J, Ostell J, editors. Bethesda (Md.): National Center for Biotechnology Information (US); 2002 (www.ncbi.nlm.nih.gov/bookshelf/br.fcgi?book=handbook&part=ch5). Multiple isoforms of certain proteins may exist, e.g., as a result of alternative RNA splicing or editing. In general, where aspects of this disclosure pertain to a gene or gene product, embodiments pertaining to allelic variants or isoforms are encompassed, if applicable, unless indicated otherwise. Certain embodiments may be directed to particular sequence(s), e.g., particular allele(s) or isoform(s).

The term "purified protein" or "purified enzyme" refers to a protein or enzyme that is greater than or equal to 95% pure. In certain embodiments, a purified enzyme refers to a protein or enzyme that is greater than 96% pure. In certain embodiments, a purified enzyme refers to a protein or enzyme that is greater than 97% pure. In certain embodiments, a purified enzyme refers to a protein or enzyme that is greater than 98% pure. In certain embodiments, a purified enzyme refers to a protein or enzyme that is greater than 99% pure. In certain embodiments, a purified enzyme refers to a protein or enzyme that is 100% pure. Protein purification is a series of processes intended to isolate one or a few proteins from a complex mixture, usually cells, tissues or whole organisms. Protein purification is vital for the characterization of the function, structure and interactions of the protein of interest. The purification process may separate the protein and non-protein parts of the mixture, and finally separate the desired protein from all other proteins. Separation of one protein from all others is typically the most laborious aspect of protein purification. Separation steps usually exploit differences in protein size, physico-chemical properties, binding affinity and biological activity. The term "partially purified protein" or "partially purified enzyme" refers to a protein or enzyme that is less than 95% pure. The term "unpurified protein" or "unpurified enzyme" refers to a protein or enzyme that has not undergone protein purification.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmologic disorders, movement disorders, demyelinating diseases, spinal cord disorders, and disorders of peripheral nerves, muscle and neuromuscular junctions. Addiction and mental illness, include, but are not limited to, bipolar disorder, depression, and schizophrenia, and are also included in the definition of neurological diseases. Examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting;

familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "psychiatric disorder" refers to a disease of the mind and includes diseases and disorders listed in the Diagnostic and Statistical Manual of Mental Disorders—Fourth Edition (DSM-IV), published by the American Psychiatric Association, Washington D.C. (1994). Psychiatric disorders include, but are not limited to, anxiety disorders (e.g., acute stress disorder agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence, amphetamine dependence, *cannabis* dependence, cocaine dependence, hallucinogen dependence, inhalant dependence, nicotine dependence, opioid dependence, phencyclidine dependence, and sedative dependence), adjustment disorder, autism, delirium, dementia, multi-infarct dementia, learning and memory disorders (e.g., amnesia and age-related memory loss), and Tourette's disorder.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "enzyme" refers to macromolecular biological catalyst. Enzymes accelerate the rate of chemical reactions. The molecules upon which enzymes may act are called substrates, and the enzyme converts the substrates into different molecule known as products. Almost all metabolic processes in a cell need enzymatic catalysis in order to occur at rates fast enough to sustain life. Metabolic pathways depend upon enzymes to catalyze individual steps. Enzymes are known to catalyze more than 5000 biochemical reaction types. Most enzymes are protein. Like all catalysts, enzymes increase the reaction rate by lowering activation energy. Some enzymes can make their conversion of substrate to product occur many millions of times faster. Enzymes are like any catalyst and are not consumed in the chemical reaction nor do they alter the equilibrium of a reaction. Enzymes differ from most other catalysts by being much more specific. Enzyme activity can be affected by other molecules: inhibitors are molecules that decrease enzyme activity, and activators are molecules that increase activity. Recombinant enzymes are the result of the expression of recombinant DNA.

The terms "polynucleotide", "nucleotide sequence", "nucleic acid", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonucleotide may comprise a modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, a thio-guanine, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNAs) formed by conjugating bases to an amino acid backbone. This also includes nucleic acids containing carbohydrate or lipids.

Polynucleotides described herein may be synthesized by standard methods known in the art, e.g., by use of an automated DNA synthesizer (such as those that are commercially available from Biosearch, Applied Biosystems, etc.). As examples, phosphorothioate oligonucleotides may be synthesized by the method of Stein et al., *Nucl. Acids Res.*, 16, 3209, (1988), methylphosphonate oligonucleotides can be prepared by use of controlled pore glass polymer supports (Sarin et al., *Proc. Natl. Acad Sci. U.S.A.* 85, 7448-7451, (1988)). Polynucleotides, such as DNA (e.g., complementary DNA (cDNA), can be created naturally or artificially. Some methods for the synthesis of DNA, well known by one skilled in the art, include: DNA replication, polymerase chain reaction, and gene synthesis. DNA replication refers to DNA biosynthesis (in vivo DNA amplification). Polymerase chain reaction refers to enzymatic DNA synthesis (in vitro DNA amplification). Gene synthesis refers to physically creating artificial gene sequences, re. In certain embodiments, cDNA is synthesized from a single stranded RNA (e.g., messenger RNA (mRNA) or microRNA) template in a reaction catalyzed by the enzyme reverse transcriptase. cDNA is often used to clone eukaryotic genes in prokaryotes. When scientists want to express a specific protein in a cell that does not normally express that protein (i.e., heterologous expression), they will transfer the cDNA that codes for the protein to the recipient cell. cDNA is also produced naturally by retroviruses (such as HIV-1, HIV-2, simian immunodeficiency virus, etc.) and then integrated into the host's genome, where it creates a provirus. cDNA is derived from eukaryotic mRNA, so it contains only exons, with no introns. cDNA is most often synthesized from mature (fully spliced) mRNA using the enzyme reverse transcriptase. This enzyme, which naturally occurs in retroviruses, operates on a single strand of mRNA, generating its complementary DNA based on the pairing of RNA base pairs (A, U, G, and C) to their DNA complements (T, A, C, and G, respectively). To obtain eukaryotic cDNA whose introns have been removed:

1) A eukaryotic cell transcribes the DNA (from genes) into RNA (pre-mRNA).
2) The same cell processes the pre-mRNA strands by removing introns, and adding a poly-A tail and 5' methyl-guanine cap (this is known as post-transcriptional modification).
3) This mixture of mature mRNA strands is extracted from the cell. The poly-A tail of the post-transcriptional mRNA can be taken advantage of with oligo(dT) beads in an affinity chromatography assay.
4) A poly-T oligonucleotide primer is hybridized onto the poly-A tail of the mature mRNA template, or random hexamer primers can be added which contain every possible 6 base single strand of DNA and can therefore hybridize anywhere on the RNA (Reverse transcriptase requires this double-stranded segment as a primer to start its operation.)
5) Reverse transcriptase is added, along with deoxynucleotide triphosphates (A, T, G, C). This synthesizes one complementary strand of DNA hybridized to the original mRNA strand.
6) To synthesize an additional DNA strand, traditionally one would digest the RNA of the hybrid strand, using an enzyme like RNase H, or through alkali digestion method.
7) After digestion of the RNA, a single stranded DNA (ssDNA) is left and because single stranded nucleic acids are hydrophobic, it tends to loop around itself. It is likely that the ssDNA forms a hairpin loop at the 3' end.
8) From the hairpin loop, a DNA polymerase can then use it as a primer to transcribe a complementary sequence for the ss cDNA to provide a double stranded cDNA with identical sequence as the mRNA of interest. cDNA sequences may be incorporated into a wide variety of vectors. Such vectors can be constructed by recombinant DNA technology methods standard in the art. Vectors can be plasmid, viral, or others known in the art, used for replication and expression in non-human cells or organisms, such as bacteria, yeast, or plants. Any type of plasmid, cosmid, yeast artificial chromosome, or viral vector can be used to prepare the recombinant DNA construct that can be introduced directly into the cell.

The polynucleotides may be flanked by natural regulatory (expression control) sequences or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications, such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, isotopes (e.g., radioactive isotopes), biotin, and the like.

A "recombinant nucleic acid molecule" is a nucleic acid that has been modified, i.e., a non-naturally occurring nucleic acid or a genetically engineered nucleic acid. Furthermore, the term "recombinant DNA" refers to a nucleic acid sequence which is not naturally occurring or has been made by the artificial combination of two otherwise separated segments of nucleic acid sequence, i.e., by ligating together pieces of DNA that are not normally contiguous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al., *Molecular Cloning*, second edition, Cold Spring Harbor Laboratory, Plainview, N.Y.; (1989), or Ausubel et al, *Current Protocols in Molecular Biology*, Current Protocols (1989), and *DNA Cloning: A Practical Approach*, Volumes I and II (ed. D. N. Glover) IREL Press, Oxford, (1985); each of which is incorporated herein by reference.

The term "RNA transcript" refers to the product resulting from RNA polymerase-catalyzed transcription of a DNA sequence. When the RNA transcript is a complementary copy of the DNA sequence, it is referred to as the primary transcript, or it may be an RNA sequence derived from post-transcriptional processing of the primary transcript and is referred to as the mature RNA. "Messenger RNA (mRNA)" refers to the RNA that is without introns and can be translated into polypeptides by the cell. "cRNA" refers to complementary RNA, transcribed from a recombinant cDNA template. "cDNA" refers to DNA that is complementary to and derived from an mRNA template. The cDNA can be single-stranded or converted to double-stranded form using, for example, the Klenow fragment of DNA polymerase I.

The term "fusion protein" refers to protein created through the joining of two or more genes that originally encoded separate proteins. Translation of this fusion gene results in a single or multiple polypeptides with functional properties derived from each of the original proteins. Recombinant fusion proteins are created artificially by recombinant DNA technology for use in research, bioengineering, or as therapeutics.

The term "cell" refers to a basic structural, functional, and biological unit of all known living organisms. A cell is the smallest unit of life that can replicate independently, and cells are called the "building blocks of life". Cells consist of cytoplasm enclosed within a membrane, which contains many biomolecules such as proteins and nucleic acids. Organisms can be classified as unicellular (consisting of a single cell; including bacteria) or multicellular (including plants and animals). While the number of cells in plants and animals varies from species to species. Most plant and animal cells are visible only under a microscope, with dimension between 1 and 100 micrometers.

The term "cell line" refers a population of cells descended from a single cell and containing the same genetic makeup. Some cell lines are designated immortalized cell lines, which are a population of cells from a multicellular organism which would normally not proliferate indefinitely but, due to mutation, have evaded normal cellular senescence (the phenomenon by which normal ploid cells cease to divide) and instead can keep undergoing division.

A "vector" may be any of a number of nucleic acid molecules or viruses, or portions thereof, that are capable of mediating entry of, e.g., transferring, transporting, etc., a nucleic acid of interest between different genetic environments or into a cell. The nucleic acid of interest may be linked to, e.g., inserted into, the vector using, e.g., restriction and ligation. Vectors include, for example, DNA or RNA plasmids, cosmids, naturally occurring or modified viral genomes or portions thereof, nucleic acids that can be packaged into viral capsids, mini-chromosomes, artificial chromosomes, etc. Plasmid vectors typically include an origin of replication (e.g., for replication in prokaryotic cells). A plasmid may include part or all of a viral genome (e.g., a viral promoter, enhancer, processing or packaging signals, and/or sequences sufficient to give rise to a nucleic acid that can be integrated into the host cell genome and/or to give rise to infectious virus). Viruses or portions thereof that can be used to introduce nucleic acids into cells may be referred to as viral vectors. Viral vectors include, e.g., adenoviruses, adeno-associated viruses, retroviruses (e.g., lentiviruses), vaccinia virus and other poxviruses, herpesviruses (e.g., herpes simplex virus), and others. Viral vectors may or may not contain sufficient viral genetic information for production of infectious virus when introduced into host cells, i.e., viral vectors may be replication-competent or replication-defective. In some embodiments, e.g., where sufficient information for production of infectious virus is lacking, it may be supplied by a host cell or by another vector introduced into the cell, e.g., if production of virus is desired. In some embodiments such information is not supplied, e.g., if production of virus is not desired. A nucleic acid to be transferred may be incorporated into a naturally occurring or modified viral genome or a portion thereof or may be present within a viral capsid as a separate nucleic acid molecule. A vector may contain one or more nucleic acids encoding a marker suitable for identifying and/or selecting cells that have taken up the vector. Markers include, for example, various proteins that increase or decrease either resistance or sensitivity to antibiotics or other agents (e.g., a protein that confers resistance to an antibiotic such as puromycin, hygromycin or blasticidin), enzymes whose activities are detectable by assays known in the art (e.g., β-galactosidase or alkaline phosphatase), and proteins or RNAs that detectably affect the phenotype of cells that express them (e.g., fluorescent proteins). Vectors often include one or more appropriately positioned sites for restriction enzymes, which may be used to facilitate insertion into the vector of a nucleic acid, e.g., a nucleic acid to be expressed. An expression vector is a vector into which a desired nucleic acid has been inserted or may be inserted such that it is operably linked to regulatory elements (also termed "regulatory sequences", "expression control elements", or "expression control sequences") and may be expressed as an RNA transcript (e.g., an mRNA that can be translated into protein). Expression vectors include regulatory sequence(s), e.g., expression control sequences, sufficient to direct transcription of an operably linked nucleic acid under at least some conditions; other elements required or helpful for expression may be supplied by, e.g., the host cell or by an in vitro expression system. Such regulatory sequences typically include a promoter and may include enhancer sequences or upstream activator sequences. In some embodiments a vector may include sequences that encode a 5' untranslated region and/or a 3' untranslated region, which may comprise a cleavage and/or polyadenylation signal. In general, regulatory elements may be contained in a vector prior to insertion of a nucleic acid whose expression is desired or may be contained in an inserted nucleic acid or may be inserted into a vector following insertion of a nucleic acid whose expression is desired. As used herein, a nucleic acid and regulatory element(s) are said to be "operably linked" when they are covalently linked so as to place the expression or transcription of the nucleic acid under the influence or control of the regulatory element(s). For example, a promoter region would be operably linked to a nucleic acid if the promoter region were capable of effecting transcription of that nucleic acid. One of ordinary skill in the art will be aware that the precise nature of the regulatory sequences useful for gene expression may vary between species or cell types, but may in general include, as appropriate, sequences involved with the initiation of transcription, RNA processing, or initiation of translation. The choice and design of an appropriate vector and regulatory element(s) is within the ability and discretion of one of ordinary skill in the art. For example, one of skill in the art will select an appropriate promoter (or other expression control sequences) for expression in a desired species (e.g., a mammalian species) or cell type. A vector may contain a promoter capable of directing expression in mammalian cells, such as a suitable viral promoter, e.g., from a cytomegalovirus (CMV), retrovirus, simian virus (e.g., SV40), papilloma virus, herpes virus or other virus that infects mammalian cells, or a mammalian promoter from, e.g., a gene such as EF1alpha, ubiquitin (e.g., ubiquitin B or C), globin, actin, phosphoglycerate kinase (PGK), etc., or a composite promoter such as a CAG promoter (combination of the CMV early enhancer element and chicken beta-actin promoter). In some embodiments a human promoter may be used. In some embodiments, a promoter that ordinarily directs transcription by a eukaryotic RNA polymerase II (a "pol II promoter") or a functional variant thereof is used. In some embodiments, a promoter that ordinarily directs transcription by a eukaryotic RNA polymerase I promoter, e.g., a promoter for transcription of ribosomal RNA (other than 5S rRNA) or a functional variant thereof is used. In some embodiments, a promoter that ordinarily directs transcription by a eukaryotic RNA polymerase III (a "pol III promoter"), e.g., (a U6, H1, 7SK or tRNA promoter or a functional variant thereof) may be used. One of ordinary skill in the art will select an appropriate promoter for directing transcription of a sequence of interest. Examples of expression vectors that may be used in mammalian cells include, e.g., the pcDNA vector series, pSV2 vector series, pCMV vector series, pRSV vector series, pEF1 vector series, Gateway® vectors, etc. Examples of virus vectors that may be used in mammalian cells include, e.g., adenoviruses, adeno-associated viruses, poxviruses such as vaccinia viruses and attenuated poxviruses, retroviruses (e.g., lentiviruses), Semliki Forest virus, Sindbis virus, etc. In some embodiments, regulatable (e.g., inducible or repressible) expression control element(s), e.g., a regulatable promoter, is/are used so that expression can be regulated, e.g., turned on or increased or turned off or decreased. For example, the tetracycline-regulatable gene expression system (Gossen & Bujard, Proc. Natl. Acad. Sci. 89:5547-5551, 1992) or variants thereof (see, e.g., Allen, N, et al. (2000) Mouse Genetics and Transgenics: 259-263; Urlinger, S, et al. (2000). Proc. Natl. Acad. Sci. U.S.A. 97 (14): 7963-8; Zhou, X., et al. (2006). Gene Ther. 13 (19): 1382-1390 for examples) can be employed to provide inducible or repressible expression. Other inducible/repressible systems may be used in various embodiments. For example, expression control elements that can be regulated by small molecules such as artificial or naturally occurring hormone receptor ligands (e.g., steroid receptor ligands such as naturally occurring or synthetic estrogen receptor or glucocorticoid receptor ligands), tetracycline or analogs thereof, metal-regulated systems (e.g., metallothionein promoter) may be used in certain embodiments. In some embodiments, tissue-specific or cell type specific regulatory element(s) may be used, e.g., in order to direct expression in one or more selected tissues or cell types. In some embodiments a vector capable of being stably maintained and inherited as an episome in mammalian cells (e.g., an Epstein-Barr virus-based episomal vector) may be used. In some embodiments a vector may comprise a polynucleotide sequence that encodes a polypeptide, wherein the polynucleotide sequence is positioned in frame with a nucleic acid inserted into the vector so that an N- or C-terminal fusion is created. In some embodiments the polypeptide encoded by the polynucleotide sequence may be a targeting peptide. A targeting peptide may comprise a signal sequence (which directs secretion of a protein) or a sequence that directs the expressed protein to a specific organelle or location in the cell such as the nucleus or mitochondria. In some embodiments the polypeptide comprises a tag. A tag may be useful to facilitate detection and/or purification of a protein that contains it. Examples of tags include polyhistidine-tag (e.g., 6×-His tag), glutathione-S-transferase, maltose binding protein, NUS tag, SNUT tag, Strep tag, epitope tags such as V5, HA, Myc, or FLAG. In some embodiments a protease cleavage site is located in the region between the protein encoded by the inserted nucleic acid and the polypeptide, allowing the polypeptide to be removed by exposure to the protease.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The terms "agroinfiltration," "*Agrobacterium*-infiltration," or "*Agrobacterium*-mediated infiltration" refer to a method used in plant biology and plant biotechnology to induce transient expression of genes in a plant, or isolated leaves from a plant, or even in cultures of plant cells, in order to produce a desired protein. In the method a suspension of *Agrobacterium tumefaciens* is introduced into a plant leaf by direct injection or by vacuum infiltration, or brought into association with plant cells immobilized on a porous support (plant cell packs), whereafter the bacteria transfer the desired gene into the plant cells via transfer of T-DNA. The main benefit of agroinfiltration when compared to more traditional plant transformation is speed and convenience, although yields of the recombinant protein are generally also higher and more consistent. The first step is to introduce a gene of interest to a strain of *Agrobacterium tumefaciens*. Subsequently, the strain is grown in a liquid culture and the resulting bacteria are washed and suspended into a suitable buffer solution. For injection, this solution is then placed in a syringe (without a needle). The tip of the syringe is pressed against the underside of a leaf while simultaneously applying gentle counter pressure to the other side of the leaf. The *Agrobacterium* suspension is then injected into the airspaces inside the leaf through stomata, or sometimes through a tiny incision made to the underside of the leaf. Vacuum infiltration is another way to introduce *Agrobacterium* deep into plant tissue. In this procedure, leaf disks, leaves, or whole plants are submerged in a beaker containing the solution, and the beaker is placed in a vacuum chamber. The vacuum is then applied, forcing air out of the intercellular spaces within the leaves via the stomata. When the vacuum is released, the pressure difference forces the *Agrobacterium* suspension into the leaves through the stomata into the mesophyll tissue. This can result in nearly all of the cells in any given leaf being in contact with the bacteria. Once inside the leaf that *Agrobacterium* remains in the intercellular space and transfers the gene of interest as part of the Ti plasmid-derived T-DNA in high copy numbers into the plants cells. The gene is then transiently expressed through RNA synthesis from appropriate species can be processed using this method, but the most common ones are *Nicotiana benthamiana* and less often, *Nicotiana tabacum*. Transient expression in cultured plant cell packs is a more recent procedure. For this technique, suspension cultured cells of tobacco (e.g., NT1 or BY2 cell lines of *Nicotiana tabacum*) are immobilized by filtration onto a porous support to form a well-aerated cell pack, then incubated with recombinant *Agrobacterium* for a time to allow T-DNA transfer, before refiltration to remove excess bacteria and liquid. Incubation of the cell pack in a humid environment for time periods up to several days allows transient expression of protein. Secreted proteins can be washed out of the cell pack by application of buffer and further filtration.

The terms "assessing", "determining", "evaluating", and "assaying" are used interchangeably herein to refer to any form of detection or measurement, and include determining whether a substance, signal, enzymatic activity, disease, condition, etc., is present or not. The result of an assessment may be expressed in qualitative and/or quantitative terms. Assessing may be relative or absolute. "Assessing the presence of" includes determining the amount of something that is present or determining whether it is present or absent.

A "biological process" may be any set of operations or molecular events, with a defined beginning and end, pertinent to the functioning of integrated living units, e.g., cells, tissues, organs, and organisms. Typically it is a series of events accomplished by one or more ordered assemblies of molecular functions. A "biological pathway" may be any series of actions and/or interactions by and among molecules in a cell that leads to a certain product or a change in a cell. Typically a biological process encompasses or is carried out via one or more biological pathways. Biological pathways include, for example, pathways pertaining to metabolism, genetic information processing (e.g., transcription, translation, RNA transport, RNA degradation; protein folding, sorting, degradation, post-translational modification; DNA replication and repair), environmental information processing (e.g., membrane transport, signal transduction), and cellular processes (e.g., cell cycle, endocytosis, vesicle trafficking), etc. It will be appreciated that the various aforementioned biological processes encompass multiple specific pathways. In some embodiments a biological pathway or process is conserved in that the pathway or process is recognizably present in both yeast and mammalian cells.

BRIEF DESCRIPTION OF THE DRAWINGS

The accompanying drawings, which constitute a part of this specification, illustrate several exemplary embodiments of the invention and together with the description, serve to explain certain principles of the invention. The embodiments disclosed in the drawings are exemplary and do not limit the scope of this disclosure.

FIG. 1 shows the chemical structures of twenty known kavalactones.

FIG. 2 shows the chemical structures of three known flavokavains.

DETAILED DESCRIPTION OF CERTAIN EMBODIMENTS

Figure 3:
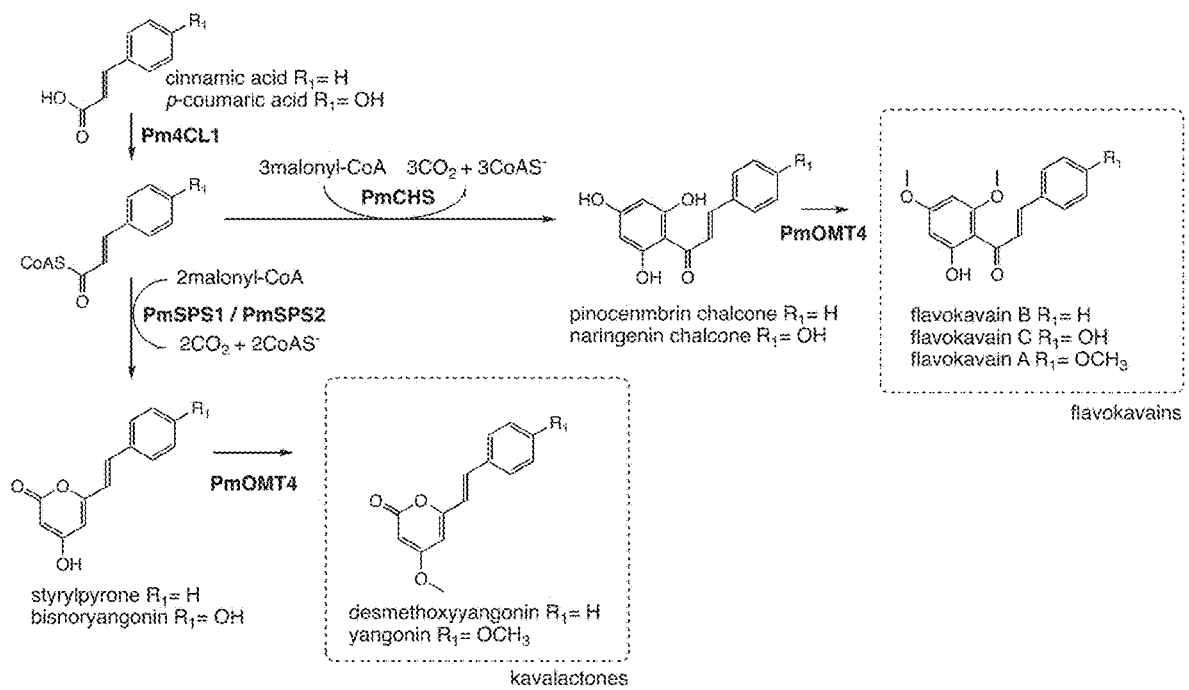
FIG. 3 shows the biosynthetic pathway of kavalactones and flavokavains.

The present disclosure provides methods, compositions, proteins, nucleic acids, cells, vectors, compounds, reagents, and systems for the production of kavalactones, flavokavains, and intermediates thereto. Described herein are the biosynthetic pathways and enzymes useful for the conversion of cinnamic acid derivatives and phenylpropanoic acid derivatives to kavalactones and flavokavains in a series of in vivo and/or in vitro enzymatic reactions. The enzymatic synthesis of kavalactones utilizes 4-coumarate-CoA ligase Pm4CL1 (or an enzyme that is at least 80% identical to SEQ ID NO: 1), styrylpyrone synthase PmSPS1 (or an enzyme that is at least 80% identical to SEQ ID NO: 2) or styrylpyrone synthase PmSPS2 (or an enzyme that is at least 80% identical to SEQ ID NO: 3), methyltransferase PmOMT4 (or an enzyme that is at least 80% identical to SEQ ID NO: 5), and any number of methyltranferases (e.g., PmOMT1 (or an enzyme at least 80% identical to SEQ ID NO: 6)), cytochrome P450 enzymes (e.g., PmMDB1 (or an enzyme at least 80% identical to SEQ ID NO: 7)), and/or NADPH-dependent reductases (e.g., PmRDCT10 (or an enzyme at least 80% identical to SEQ ED NO: 8)). The enzymatic synthesis of flavokavains utilizes at least one 4-coumarate-CoA ligase Pm4CL1 (or an enzyme that is at least 80% identical to SEQ ID NO: 1), chalcone synthase PmCHS (or an enzyme that is at least 80% identical to SEQ ID NO: 4), methyltranferase PmOMT4 (or an enzyme that is at least 80% identical to SEQ ID NO: 5, and any number of methyltranferases (e.g., PmOMT1 (or an enzyme at least 80% identical to SEQ ID NO: 6)) and cytochrome P450 enzyme PmMDB1 (or an enzyme at least 80% identical to SEQ ID NO: 7). Any of the methods to produce compounds described herein can optionally utilize chemical means or a combination of reactions utilizing enzymes described herein and chemical means.

Any of the methods described herein may include culturing cells or cultivating plants expressing enzymes described herein and isolating one or more compounds described herein from such cells or plants. Methods described herein can include harvesting tissue (e.g., leaves, roots) of a plant expressing enzymes described herein and processing the harvested tissue to isolate one or more compounds described herein therefrom. Compounds may be isolated using solvent extraction, chromatography, and/or other separation methods known in the art.

Any of the enzymatic individual steps may be combined, omitted, or done through other means and still be within the scope of the invention.

Enzymes and cDNA

Sequence identity is the amount of characters which match exactly between two different sequences. Hereby, gaps are not counted and the measurement is relational to the shorter of the two sequences. This has the effect that sequence identity is not transitive, i.e. if sequence A=B and B=C then A is not necessarily equal C (in terms of the identity distance measure): A: AAGGCTT; B: AAGGC; C: AAGGCAT. Here identity(A,B)=100% (5 identical nucleotides/min(length(A),length(B))). Identity(B,C)=100%, but identity(A,C)=85% ((6 identical nucleotides/7)). So 100% identity does not mean two sequences are the same. Sequence identity can be applied to polypeptides and polynucleotide. For example, the phrase an enzyme "that is at least Y % identical to SEQ ID NO: X", can be understood to apply the description above for comparing amino acid sequences to determine that an enzyme is at least 80% identical to a enzyme with a SEQ ID NO described herein.

In certain embodiments, the enzyme (polypeptide) or DNA (polynucleotide) is a variant of a natural or artificial enzyme or DNA. A "variant" of a particular polypeptide or polynucleotide has one or more additions, substitutions, and/or deletions with respect to the polypeptide or polynucleotide, which may be referred to as the "original polypeptide" or "original polynucleotide", respectively. An addition may be an insertion or may be at either terminus. A variant may be shorter or longer than the original polypeptide or polynucleotide. The term "variant" encompasses "fragments". A "fragment" is a continuous portion of a polypeptide or polynucleotide that is shorter than the original polypeptide or polynucleotide. In some embodiments a variant comprises or consists of a fragment. In some embodiments a fragment or variant is at least 20%, 30%, 40%, 50%, 60%, 70%, 80%, 90%, 95%, 96%, 97%, 98%, 99%, or more as long as the original polypeptide or polynucleotide. A fragment may be an N-terminal, C-terminal, or internal fragment. In some embodiments a variant polypeptide comprises or consists of at least one domain of an original polypeptide. In some embodiments a variant polypeptide or polynucleotide comprises or consists of a polypeptide or polynucleotide that is at least 70%, 80%, 90%, 95%, 96%, 97%, 98%, 99%, or more identical in sequence to the original polypeptide or polynucleotide over at least 50%, 60%, 70%, 80%, 90%, 95%, 96%, 97%, 98%, 99%, or 100% of the original polypeptide or polynucleotide. In some embodiments the sequence of a variant polypeptide comprises or consists of a sequence that has N amino acid differences with respect to an original sequence, wherein N is any integer up to 1%, 2%, 5%, or 10% of the number of amino acids in the original polypeptide, where an "amino acid difference" refers to a substitution, insertion, or deletion of an amino acid. In some embodiments a substitution is a conservative substitution. Conservative substitutions may be made, e.g., on the basis of similarity in side chain size, polarity, charge, solubility, hydrophobicity, hydrophilicity and/or the amphipathic nature of the residues involved. In some embodiments, conservative substitutions may be made according to Table A, wherein amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

TABLE A

| Aliphatic | Non-polar | G A P |
| | | I L V |
| | Polar - uncharged | C S T M |
| | | N Q |
| | Polar - charged | D E |
| | | K R |
| Aromatic | | H F W Y |

In some embodiments, proline (P), cysteine (C), or both are each considered to be in an individual group. Within a particular group, certain substitutions may be of particular interest in certain embodiments, e.g., replacements of leucine by isoleucine (or vice versa), serine by threonine (or vice versa), or alanine by glycine (or vice versa).

In some embodiments a variant is a biologically active variant, i.e., the variant at least in part retains at least one activity of the original polypeptide or polynucleotide. In some embodiments a variant at least in part retains more than one or substantially all known biologically significant activities of the original polypeptide or polynucleotide. An activity may be, e.g., a catalytic activity, binding activity, ability to perform or participate in a biological structure or process, etc. In some embodiments an activity of a variant may be at least 10%, 20%, 30%, 40%, 50%, 60%, 70%, 80%, 90%, 95%, or more, of the activity of the original polypeptide or polynucleotide, up to approximately 100%, approximately 125%, or approximately 150% of the activity of the original polypeptide or polynucleotide, in various embodiments. In some embodiments a variant, e.g., a biologically active variant, comprises or consists of a polypeptide at least 95%, 96%, 97%, 98%, 99%, 99.5% or 100% identical to an original polypeptide over at least 70%, 75%, 80%, 85%, 90%, 95%, 96%, 97%, 98%, or 99% or 100% of the original polypeptide. In some embodiments an alteration, e.g., a substitution or deletion, e.g., in a functional variant, does not alter or delete an amino acid or nucleotide that is known or predicted to be important for an activity, e.g., a known or predicted catalytic residue or residue involved in binding a substrate or cofactor. Variants may be tested in one or more suitable assays to assess activity.

Each amino acid in the enzyme sequence can be encoded by multiple DNA codons. Therefore, there are many possible cDNA sequences that will translated to the same amino acid sequences described herein and produce the same enzyme. Examples of cDNA sequences that encode the enzymes described herein are shown in Example 6.

In certain embodiments, an enzyme of the present disclosure is at least 80%, 85%, 90%, 95%, or 100% identical to an enzyme with a SEQ ID NO described herein. In certain embodiments, an enzyme of the present disclosure is greater than 95%, 96%, 97%, 98%, or 99% identical to an enzyme with a SEQ ID NO described herein.

The enzymes described herein (e.g., 4-coumarate-CoA ligase Pm4CL1 or an enzyme that is at least 80% identical to SEQ ID NO: 1, styrylpyrone synthase PmSPS1 or an enzyme that is at least 80% identical to SEQ ID NO: 2, styrylpyrone synthase PmSPS2 or an enzyme that is at least 80% identical to SEQ ID NO: 3, chalcone synthase PmCHS or an enzyme that is at least 80% identical to SEQ ID NO: 4, methyltransferase PmOMT4 or an enzyme that is at least 80% identical to SEQ ID NO: 5, methyltransferase PmOMT1 or an enzyme that is at least 80% identical to SEQ ID NO: 6, cytochrome P450 enzyme PmMDB1 or an enzyme that is at least 80% identical to SEQ ID NO: 7, and NADPH-dependent reductase PmRDCT10 or an enzyme that is at least 80% identical to SEQ ID NO: 8) are isolated or derived from wildtype, mutant or recombinant *Piper methysticum*. In certain embodiments, the enzymes are produced using recombinant technology. In certain embodiments, an acid-thiol ligase (EC 6.2.1.A) is used to form carbon-sulfur bonds, wherein A is an integer between 1 and 100, inclusive. The acid-thiol ligase is isolated or derived from wildtype, mutant, or recombinant *Piper methysticum*. The acid-thiol ligase can be used as an unpurified enzyme, partially purified enzyme, or purified enzyme. In certain embodiments, the amino acid sequence of the enzyme is at least 80% identical to SEQ ID NO: 1, designated 4-coumarate-CoA ligase PmCL1, wherein SEQ ID NO: 1 is MKMVVDTIATDRCVYRSKLPDIEIKNDMSLHNYC-FQNIGAYRDNPCLINGSTGEVYTYG EVETTARR-VAAGLHRMGVQQREVIMILLPNSPEFVFAFLGASFR-GAMSTTANPFYTPQEI AKQVKASGAKLIVTMSAY-VDKVRDLAEERGVKVVCVDAPPPGCSHFSELSGADE-SELP EVDIDPDDVVALPYSSGTTGLPKGVML-THRSQVTSVAQQVDGENPNLYFRPDDVLLCV LPLFHIYSLNSVLFCGLRVGAAILIMQKFEITALMEL-VQKYKVTIAPIVPPIVLAIAKSPLV DKYDLSSIRTV-MSGAAPMGKELEDAVRAKLPNAKLGQGYGMT-EAGPVLSMCLAFAKE PFEIKSGSCGTVVRNAQL-KIVDPETGAYLPRNQPGEICIRGSQIMKGYLN-DAAATQRTID KEGWLHTGDIGYVDDDEELFIVDRL-KEIIKYKGFQVAPAELEAILITHPNIADAAVVPMK DEAAGEVPVAFVVTSNGSVISEDEIKQFISKQV-VFYKRINRVFFVDSIPKAPSGKILRKDL RGRLAA-GIPK. In certain embodiments, the acid-thiol ligase is 4-coumarate-CoA ligase (EC 6.2.1.12).

In certain embodiments, a transferase or synthase (EC 2.3.1.B) is used to form styrylpyrones from coenzyme A esters of cinnamic acids, wherein B is an integer between 1 and 300, inclusive. In certain embodiments, a transferase or synthase (EC 2.3.1.B) is used to form styrylpyrones from coenzyme A esters of cinnamic acids, wherein B is an integer between 1 and 300, inclusive. The transferase or synthase is isolated or derived from wildtype, mutant, or recombinant *Piper methysticum*. The transferase or synthase can be used as an unpurified enzyme, partially purified enzyme, or purified enzyme. In certain embodiments, the synthase belongs to an enzyme family of type III polyketide synthases. In certain embodiments, the amino acid sequence of the enzyme is at least 80% identical to SEQ ID NO: 2, designated styrylpyrone synthase PmSPS1, wherein SEQ ID NO: 2 is MSKTVEDRAAQRAKGPATVLAIGTATPANV VYQTDYPDYYFRVTKSEHMTKLKNKFQRMC-DRSTIKKRYMVLTEELLEKNLSLCTYME PSLDAR-QDILVPEVPKLGKEAADEAIAEWGRPKSEITHLI-FCTTCGVDMPGADYQLTKLL GLRSSVRRTMLYQQ-GCFGGGTVLRLAKDLAENNAGARVLVVCSEITTAVN-FRGPSDTH LDLLVGLALFGDGAAAVIVGADPDP-TLERPLFQIVSGAQTILPDSEGAINGHLREVGLTIR LLKDVPGLVSMNIEKCLMEAFAPMGIHDWNSIFWI-AHPGGPTILDQVEAKLGLKEEKLK STRAVLREYG-NMSSACVLFILDEVRKRSMEEGKTTTGEGFDWGV-LFGFGPGFTVETVVL HSMPIPKADEGR. In certain embodiments, the amino acid sequence of the enzyme is at least 80% identical to SEQ ID NO: 3, designated styrylpyrone synthase PmSPS2, wherein SEQ ID NO: 3 is MSKMVEEHWAAQRARGPATVLAIGTANPPNVLYQ-ADYPDFYFRVTKSEHMT QLKEKFKRICDKSAIRKR-HLHLTEELLEKNPNICAHMAPSLDARQDIAVVEVP-KLAKEA ATKAIKEWGRPKSDITHLIFCTTCGVDMP-GADYQLTTLLGLRPTVRRTMLYQQGCFAGG TVLRHAKDFAENNRGARVLAVCSEFTVMNFSGPSE-AHLDSMVGMALFGDGASAVIVG ADPDFAIER-PLFQLVSTTQTIVPDSDGAIKCHLKEVGLTLHLVKN-VPDLISNNMDKILEEA FAPLGIRDWNSIFWTAHPG-GAAILDQLEAKLGLNKEKLKTTRTVLREYGNMS-SACVCFV LDEMRRSSLEEGKTTSGEGLEWGILL-GFGPGLTVETVVLRSVPISTAN. In certain embodiments, the amino acid sequence of the enzyme is at least 80% identical to SEQ ID NO: 4, designated chalcone synthase PmCHS, wherein SEQ ID NO: 4 is MSKTVEEI-WAAQRARGPA TVLAIGTAAPANVVYQADYPDYY-FRITKSEHMTELKEKFRRMCDKSMITKRHMHLSEE LLKNNPDICAYMAPSLDARQDMVVVEVPKLGK-EAAAKAIKEWGRPKSAITHLIFCTTSG VDMPGADF-QLTKLLGLCPSVRRTMLYQQGCFAGGTVLRLAKD-LAENNAGARVLVVCS EITAVTFRGPSETHLDSMVG-QALFGDGASAIIVGADPDPVIERPLFQIVSAAQTIL-PDSDG AIDGHLREVGLTFHLLKDVPGLISKNIEKS-LKEAFAPLGIDDWNSIFWIVHPGGPAILDQV EAK-LRLKVEKLKTTRTVLSEYGNMSSACVLFILDEMRRN-SMEEGKATTGEGLHWGVLF GFGPGLTVETVVLHSL-PIAEAN. In certain embodiments, the synthase is chalcone synthase (EC 2.3.1.74).

The amino acid sequences of the polyketide synthases described herein contain conserved catalytic triads. In certain embodiments, the conserved catalytic triad of PmSPS1 is Cys164, His304, and Asn337. In certain embodiments, the conserved catalytic triad of PmSPS2 is Cys164, His303, and Asn336. In certain embodiments, the conserved catalytic triad of PmCHS is Cys164, His303, and Asn336.

In certain embodiments, an O-methyltransferase (EC 2.1.1.C) is used to methylate hydroxyl groups substituting styrylpyrones, wherein C is an integer between 1 and 200, inclusive. In certain embodiments, an O-methyltransferase (EC 2.1.1.C) is used to methylate hydroxyl groups substituting chalcones, wherein C is an integer between 1 and 200, inclusive. The O-methyltransferase is isolated or derived from wildtype, mutant, or recombinant *Piper methysticum*. The O-methyltransferase can be used as an unpurified enzyme, partially purified enzyme, or purified enzyme. In certain embodiments, the amino acid sequence of the enzyme is at least 80% identical to SEQ ID NO: 5, designated O-methyltransferase PmOMT4, wherein SEQ ID NO: 5 is MEQAVFKDQSPSRDDIDEELFQSALYLSTAVVTVPAAIMAANDLDVLQ IIAKAGPGAHLSPTEIVSHLPTRNPNAAAALHRILRVLASHSILECSSRCEGEAKYGLRPV CKFFLNDKDGVSLNAMPSFVQSRVFIDSWQYMKDAVLEGVVPFEKAYGMPFYQFQAV NTKFKETFAKAMAAHSTLVVKKMLDTYNGFEGLTELMDVAGGTGSTLNLIVSKYPQIK GTNFDLKHVIEAAPNYPGVKHLSGDMFDSIPSAKNIIMKWILHNWSDEHCVKLLKNCYT SLPEFGKLIVVDSIVGEDVDAGLTTTNVFGCDFTMLTFPPNAKERTREEFQDLAKASGFS TFKPICCAYGVWVMEFHK. In certain embodiments, the amino acid sequence of the enzyme is at least 80% identical to SEQ ID NO: 6, designated O-methyltransferase PmOMT1, wherein SEQ ID NO: 6 is MNDQELHGYSQNAQPQLWNLLLSFINSMSLKCAVELGIPDIIHSHAQ TPINITDLAASIPIPPNKTSQFRRLMRLLVHSNVFSVHKREDGDEGFLLTPMSRILVTSND NNGGNLSPFVSMMVDPSLVSPWHFLGQWLKGNDTQGTPFRMCHGEEMWDWANKYP DFNKKFNMAMVCDSQYLMKIIVKKCATAFEGKRSLIDVGGGTGGAARSIAEAFPDIQEV SVLDLPHVVAGLPNDSRVKFVGGDMFHTIPPADVVLLKAIFHGWNDEECIKILKNCKKA IPSKEEGGKVMILDMVVNSAPGDHMITEDQYFMDLMMITYARGLERDENEWKKLFKD AGFTSYKITHGLGTSSLIELYP. In certain embodiments, the synthase is chalcone synthase (EC 2.3.1.74).

In certain embodiments, a methylenedioxy bridge-forming enzyme is used to form a methylenedioxy moiety from a hydroxyl group and a methoxy group each separately bonded to adjacent carbons of an aromatic ring belonging to a styrylpyrone or chalcone compound. The methylenedioxy bridge-forming enzyme is isolated or derived from wildtype, mutant, or recombinant *Piper methysticum*. The methylenedioxy bridge-forming enzyme can be used as an unpurified enzyme, partially purified enzyme, or purified enzyme. In certain embodiments, methylenedioxy bridge-forming enzyme belongs to the P450 enzyme family. In certain embodiments, methylenedioxy bridge-forming enzyme belongs to the CYP719 enzyme family. In certain embodiments, the amino acid sequence of the enzyme is at least 80% identical to SEQ ID NO: 7, designated methylenedioxy bridge-forming enzyme PmMDB1, wherein SEQ ID NO: 7 is MEQAQWVDPTLLPAFVGIIFFFLGMFFGRSSLGAGKGAAPRSTSSTEWPDGPPKLPII GNLHQLNKGGELVHHNLAKLAQSYDRAMTIWVGSWGPMIVVSDADLAWEVLVTKSP DFAGRVLSKLSHLFNANYNTVVAYDAGPQWQSLRRGLQHGPLGPAHVSAQARFHEED MKLLVSDMMRAAQKGGSNGVVEPLAYVRRATIRFLSRLCFGEAFNDEAFVEGMDEAV EETIGATGHARILDAFYFTRHLPIIRRSFIDTVNAKKKIESLVRPLLSRPAPPGSYLHFLLST DAPENMIIFRIFEVYLLGVDSTASTTTWALAFLVSNQQAQEKLHNELAQYCASQNNQIIK ADDVGKLSYLLGVVKETMRMKPIAPLAVPHKTLKETMLDGKRVAAGTTVVVN-LYAVH YNPKLWPEPEQFRPERFVVGASGGNGGGSSEYMLQSYLPFGGGMRSCAGMEVGKLQV AMVVANLVMAFKWLPEEEGKMPDLAEDMTFVLMMKKPLAAKIVPRA.

In certain embodiments, a dehydrogenase or reductase (EC 1.1.1.D) is used to reduce the $C_5$-$C_6$ double bond of kavalactones into a single bond (FIG. 1), wherein D is an integer between 1 and 450, inclusive. The dehydrogenase or reductase is isolated or derived from wildtype, mutant, or recombinant *Piper methysticum*. The dehydrogenase or reductase can be used as an unpurified enzyme, partially purified enzyme, or purified enzyme. In certain embodiments, the reductase is a NADPH-dependent reductase. In certain embodiments, the amino acid sequence of the enzyme is at least 80% identical to SEQ ID NO: 8, designated NADPH-dependent reductase PmRDCT10, wherein SEQ ID NO: 8 is METERKSRICVTGAGG FVASWVVKLFLSKGYLVHGTVRDLGEEKTAHLRKLEGAYHNLQLFKADLLDYESLLGA ITGCDGVLHVATPVPSSKTAYSGTELVKTAVNGTLNVLRACTEAKVKKVIYVSSTAAVL VNPNLPKDKIPDEDCWTDEEYCRTTPFFLNWYCLAKTAAEKNALEYGDKEGINVISICPS YIFGPMLQPTINSSNLELLRLMKGDDESIENKFLLMVDVRDVAEAILLLYEKQETSGRYIS SPHGMRQSNLVEKLESLQPGYNYHKNFVDIKPSWTMISSEKLKKLGWKPRPLEDTISET VLCFEEHGLLENE.

Protein sequencing encompasses the process of determining the amino acid sequence of all or part of a protein or peptide. The two major methods of protein sequencing are Edman degradation using a protein sequenator and mass spectrometry. Typically, only part of the protein's sequence needs to be determined experimentally in order to identify the protein with reference to databases of protein sequences deduced from the DNA sequences of their genes.

Prior to attempting to find the ordered sequence of a protein, it is often desirable to know the unordered amino acid composition of a protein as this knowledge can be used to facilitate the discovery of errors in the sequencing process or to distinguish between ambiguous results. Knowledge of the frequency of certain amino acids may also be used to choose which protease to use for digestion of the protein. The misincorporation of low levels of non-standard amino acids (e.g. norleucine) into proteins may also be determined. A generalized method often referred to as amino acid analysis for determining amino acid frequency is as follows: 1) hydrolyze a known quantity of protein into its constituent amino acids; and 2) separate and quantify the amino acids.

Hydrolysis is done by heating a sample of the protein in 6 M hydrochloric acid to approximately 100 to 110° C. for 24 hours or longer. Proteins with many bulky hydrophobic groups may require longer heating periods. However, these conditions are so vigorous that some amino acids (e.g., serine, threonine, tyrosine, tryptophan, glutamine, and cysteine) are degraded. To circumvent this problem the following strategy is employed: 1) heat separate samples for different times; 2) analyze the composition of each resulting solution; and 3) extrapolating back to zero hydrolysis time. A variety of reagents are known to prevent or reduce degradation, such as thiol reagents or phenol to protect tryptophan and tyrosine from attack by chlorine, and pre-oxidizing cysteine. In addition, measuring the quantity of ammonia evolved allows for the determination of the extent of amide hydrolysis.

After the hydrolysis step, the amino acids can be separated by ion-exchange chromatography and then derivatized to facilitate their detection. More commonly, the amino acids are derivatized then resolved by reversed phase HPLC.

The first major method for protein sequencing is the Edman degradation, which consists of the following steps: 1) break any disulfide bridges in the protein with a reducing agent like 2-mercaptoethanol. A protecting group such as iodoacetic acid may be necessary to prevent the bonds from re-forming; 2) separate and purify the individual chains of the protein complex, if there are more than one; 3) determine the amino acid composition of each chain; 4) determine the terminal amino acids of each chain; 5) break each chain into fragments under 50 amino acids long; 6) separate and purify the fragments; 7) determine the sequence of each fragment; 8) repeat with a different pattern of cleavage; and 9) construct the sequence of the overall protein.

Peptides longer than about 50-70 amino acids long cannot be sequenced reliably by the Edman degradation. Therefore, long protein chains need to be broken up into small fragments that can then be sequenced individually. Digestion is done either by endopeptidases such as trypsin or pepsin or by chemical reagents such as cyanogen bromide. Different enzymes give different cleavage patterns, and the overlap between fragments can be used to construct an overall sequence.

The seventh step of the Edman degradation begins with adsorbing the peptide to be sequenced onto a solid surface. One common substrate is glass fiber coated with polybrene, a cationic polymer. The Edman reagent, phenylisothiocyanate (PITC), is added to the adsorbed peptide, together with a mildly basic buffer solution of trimethylamine. This reacts with the amine group of the N-terminal amino acid. The terminal amino acid can then be selectively detached by the addition of anhydrous acid. The derivative then isomerizes to give a substituted phenylthiohydantoin, which can be washed off and identified by chromatography, and the cycle can be repeated. The efficiency of each step is about 98%, which allows about 50 amino acids to be reliably determined.

Automated Edman sequencers called protein sequenators are now in widespread use, and are able to sequence peptides up to approximately 50 amino acids long. A sample of the protein or peptide is immobilized in the reaction vessel of the protein sequenator and the Edman degradation is performed. Each cycle releases and derivatizes one amino acid from the protein or peptide's N-terminus and the released amino acid derivative is then identified by HPLC. The sequencing process is done repetitively for the whole polypeptide until the entire measurable sequence is established or for a pre-determined number of cycles.

The second major method for protein sequencing is mass spectrometry, which consists of the following steps:
1) The protein is isolated, typically by SDS-PAGE or chromatography.
2) The isolated protein may be chemically modified to stabilize cysteine residues (e.g., S-amidomethylation or S-carboxymethylation).
3) The protein is digested with a specific protease to generate peptides. Trypsin, which cleaves selectively on the C-terminal side of lysine or arginine residues, is the most commonly used protease. Its advantages include i) the frequency of Lys and Arg residues in proteins, ii) the high specificity of the enzyme, iii) the stability of the enzyme and iv) the suitability of tryptic peptides for mass spectrometry.
4) The peptides may be desalted to remove ionizable contaminants and subjected to MALDI-TOF mass spectrometry. Direct measurement of the masses of the peptides may provide sufficient information to identify the protein, but further fragmentation of the peptides inside the mass spectrometer is often used to gain information about the peptides' sequences. Alternatively, peptides may be desalted and separated by reversed phase HPLC and introduced into a mass spectrometer via an ESI source. LC-ESI-MS may provide more information than MALDI-MS for protein identification but typically requires more instrument time.

5) Depending on the type of mass spectrometer, fragmentation of peptide ions may occur via a variety of mechanisms such as collision-induced dissociation (CID) or post-source decay (PSD). In each case, the pattern of fragment ions of a peptide provides information about its sequence.

6) Information including the measured mass of the putative peptide ions and those of their fragment ions is then matched against calculated mass values from the conceptual (in silico) proteolysis and fragmentation of databases of protein sequences. A successful match will be found if its score exceeds a threshold based on the analysis parameters. Even if the actual protein is not represented in the database, error-tolerant matching allows for the putative identification of a protein based on similarity to homologous proteins. A variety of software packages are available to perform this analysis.

7) Software packages usually generate a report showing the identity (accession code) of each identified protein, its matching score, and provide a measure of the relative strength of the matching where multiple proteins are identified.

8) A diagram of the matched peptides on the sequence of the identified protein is often used to show the sequence coverage (% of the protein detected as peptides). When the protein is thought to be significantly smaller than the matched protein, the diagram may suggest whether the protein is an N- or C-terminal fragment of the matched protein.

Production of CoA Esters of Formula (II)

In one aspect, the present disclosure provides methods for producing a compound of Formula (II) from a compound of Formula (I), or a salt thereof, and coenzyme A (CoA) using an enzyme that is at least 80% identical to Pm4CL1 (SEQ ID NO: 1), wherein:

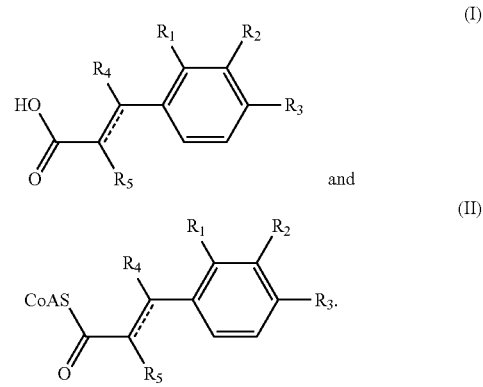

In certain embodiments, the condensation reaction of a compound of Formula (I) with coenzyme A to produce a compound of Formula (II) utilizes adenosine triphosphate. In certain embodiments, the condensation reaction of a compound of Formula (I) with coenzyme A to produce a compound of Formula (II) is performed in vitro. In certain embodiments, the in vitro condensation reaction is performed with an unpurified enzyme that is at least 80% identical to Pm4CL1 (SEQ ID NO: 1). In certain embodiments, the in vitro condensation reaction is performed with a partially purified enzyme that is at least 80% identical to Pm4CL1 (SEQ ID NO: 1). In certain embodiments, the in vitro condensation reaction is performed with an purified enzyme that is at least 80% identical to Pm4CL1 (SEQ ID NO: 1). In certain embodiments, the condensation reaction of a compound of Formula (I) with coenzyme A to produce a compound of Formula (II) is performed in vivo.

In certain embodiments, ═ a single bond. In certain embodiments, ═ is a double bond.

In certain embodiments, each of $R_1$, $R_2$, and $R_3$ independently is hydrogen, optionally substituted, cyclic or acyclic aliphatic, or —$OR_x$, wherein $R_x$ is hydrogen or optionally substituted, cyclic or acyclic aliphatic. In certain embodiments, $R_1$ is hydrogen. In certain embodiments, $R_2$ is hydrogen. In certain embodiments, $R_3$ is hydrogen. In certain embodiments, $R_1$ is —OH. In certain embodiments, $R_2$ is —OH. In certain embodiments, $R_3$ is —OH. In certain embodiments, $R_1$ is —$OCH_3$. In certain embodiments, $R_2$ is —$OCH_3$. In certain embodiments, $R_3$ is —$OCH_3$. In certain embodiments, $R_1$, $R_2$, and $R_3$ are hydrogen. In certain embodiments, $R_1$, $R_2$, and $R_3$ are —OH. In certain embodiments, $R_1$ and $R_3$ are —OH. In certain embodiments, $R_2$ and $R_3$ are —OH. In certain embodiments, $R_2$ is —$OCH_3$.

In certain embodiments, each of $R_4$ and $R_5$ independently is hydrogen or optionally substituted, cyclic or acyclic aliphatic. In certain embodiments, both $R_4$ and $R_5$ are hydrogen.

The methods to produce a compound of Formula (II) include condensing coenzyme A (CoA) with a compound of Formula (I) selected from the group consisting of:

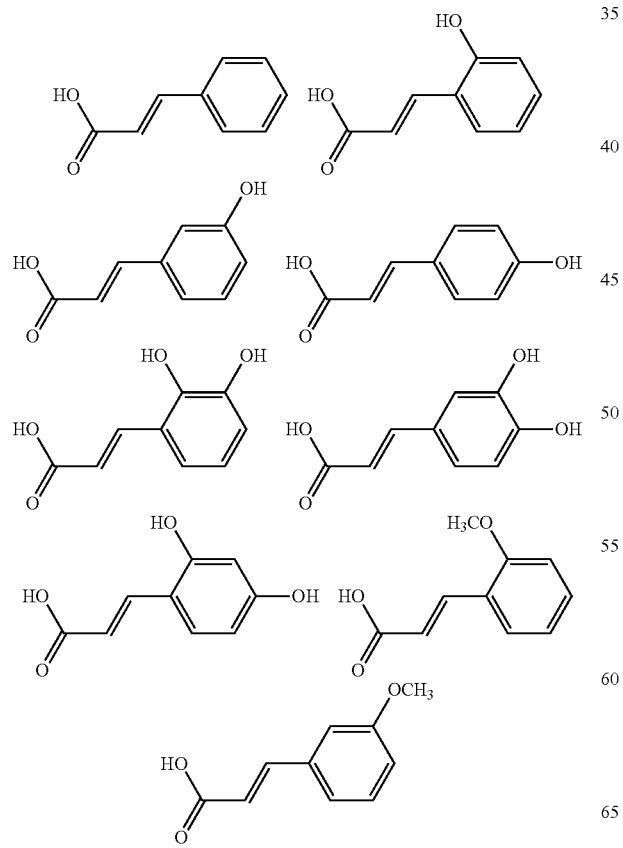

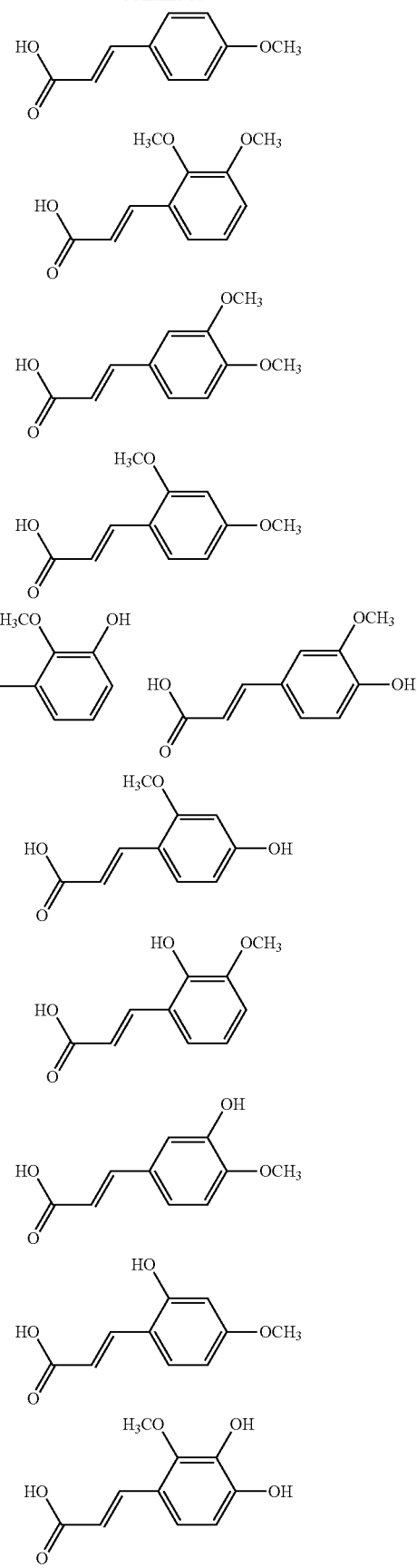

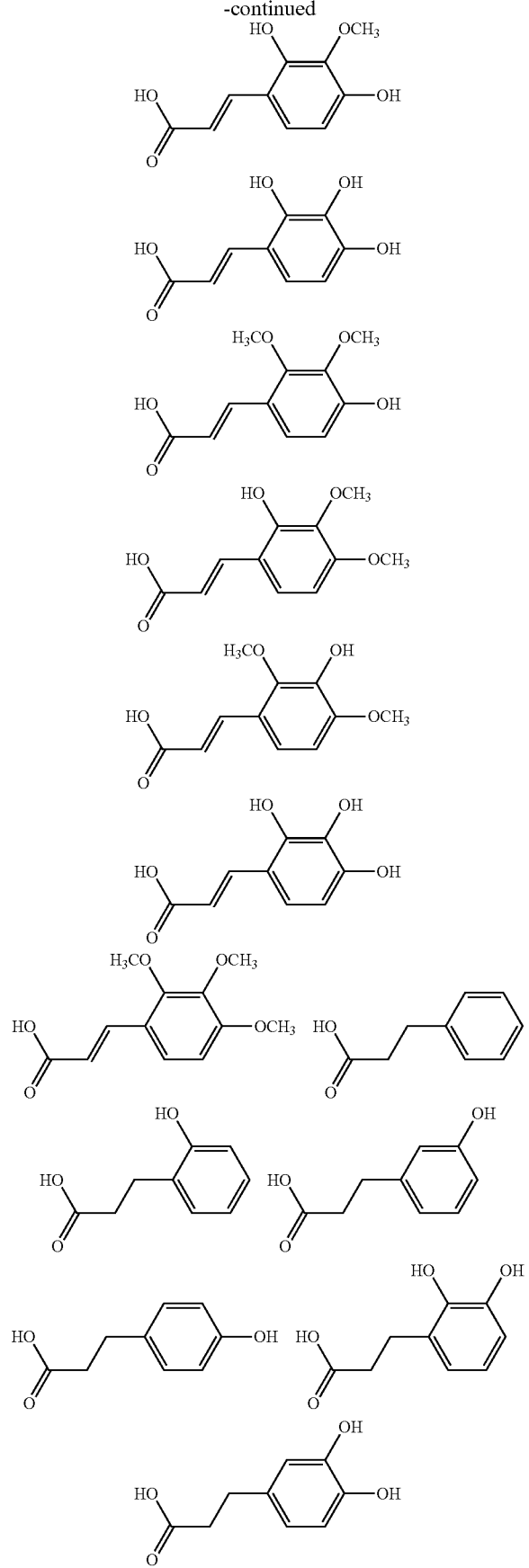
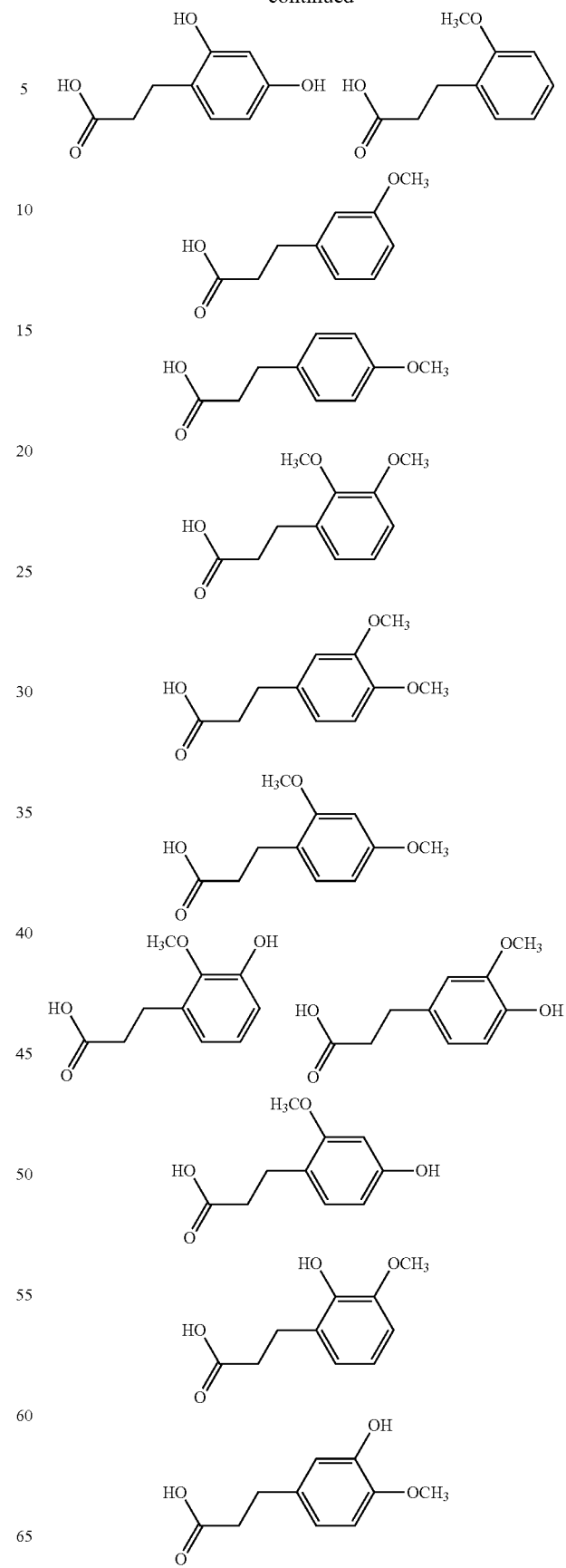

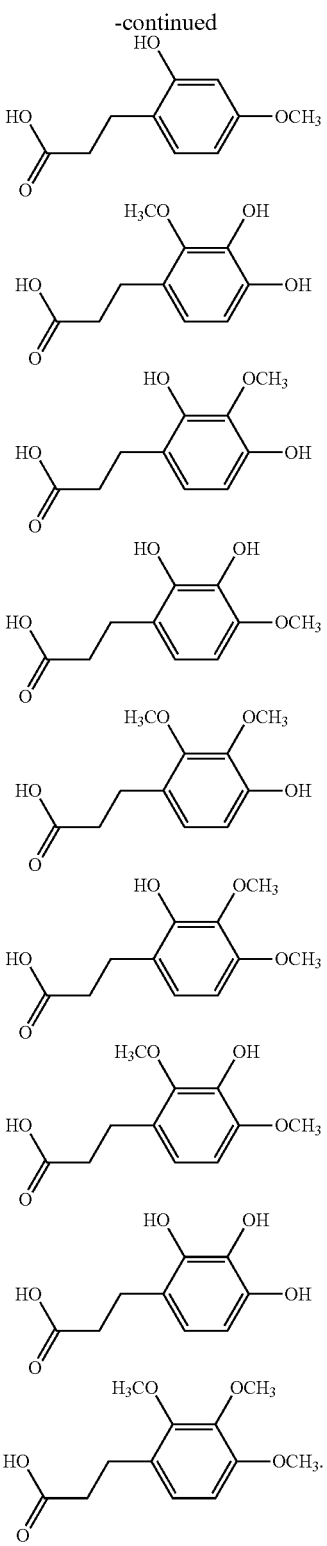

The methods to produce a compound of Formula (II) include culturing cells engineered to express an enzyme that is at least 80% identical to Pm4CL1 (SEQ ID NO: 1). In certain embodiments, the enzyme is at least 80%, 85%, 90%, 95%, or 100% identical to Pm4CL1 (SEQ ID NO: 1). In certain embodiments, the enzyme is purified before being used in a reaction with a compound of Formula (I). In certain embodiments, the enzyme is partially purified before being used in a reaction with a compound of Formula (I).

In certain embodiments, the enzyme that is at least 80% identical to Pm4CL1 (SEQ ID NO: 1) is a component of a fusion protein. A fusion protein may be created by joining two or more gene or gene segments that code for separate proteins. Translation of this fusion gene results in a single or multiple polypeptides with functional properties derived from each of the original proteins. A polyfunctional protein is a single protein that has at least two different activities, wherein that functionality is a native biological function or the result of an engineered enzyme fusion. Thus, a fusion protein may include multiple activities such as those described herein for the kavalactone or flavokavain pathway enzymes described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)).

The enzyme that is at least 80% identical to Pm4CL1 (SEQ ID NO: 1) is heterologous to the host cell. In certain embodiments, the enzyme that is at least 80% identical to Pm4CL1 (SEQ ID NO: 1) is recombinantly produced. In certain embodiments, the enzyme that is at least 80% identical to Pm4CL1 (SEQ ID NO: 1) is obtained from a wildtype organism. In certain embodiments, the enzyme that is at least 80% identical to Pm4CL1 (SEQ ID NO: 1) is obtained from a mutant organism. In certain embodiments, the enzyme that is at least 80% identical to Pm4CL1 (SEQ ID NO: 1) is obtained from a genetically-modified organism. In certain embodiments, the organism is a non-human organism. In certain embodiments, the non-human organism is selected from group consisting of bacteria, yeast, and plant. In certain embodiments, the organism is a plant. In certain embodiments, the plant is *Piper methysticum*.

A nucleic acid encoding the enzyme may be introduced into the cell via a vector (e.g., plasmids, viral vectors, cosmids, and artificial chromosomes). In certain embodiments, the nucleic acid encoding the enzyme is cDNA derived from the gene encoding the enzyme that is at least 80% identical to Pm4CL1 (SEQ ID NO: 1). In some embodiments, multiple cDNAs comprising sequences from different genes (e.g., 2, 3, 4, 5, or more genes) described herein (e.g., 4-coumarate-CoA ligase Pm4CL1 (at least 80% identity to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)), are introduced into the same cell individually, or together, or as part of a single nucleic acid.

The host cells expressing the enzyme that is at least 80% identical to Pm4CL1 (SEQ ID NO: 1) may be prokaryotic cells, such as bacterial cells (e.g., *Escherichia coli* cells), or eukaryotic cells, such as yeast cells or plant cells. In certain embodiments, the host cell is capable of expressing two or more kavalactone or flavokavain pathway enzymes described herein. In certain embodiments, the host cell is a bacteria cell and is a wildtype, mutant, recombinant, or genetically engineered form of *Escherichia coli*. In certain embodiments, the host cell is a yeast cell and is a wildtype, mutant, recombinant, or genetically engineered form of *Saccharomyces cerevisiae*. In certain embodiments, the host cell is a plant cell and is a wildtype, mutant, recombinant, or genetically engineered form of *Nicotiana benthamiana*.

Production of 6-styryl-4-hydroxyl-2-pyrone Compounds of Formula (III)

Some aspects of the present disclosure provides methods for producing a compound of Formula (III) from a compound of Formula (II), or a salt thereof, and malonyl-CoA using an enzyme that is at least 80% identical to PmSPS1 (SEQ ID NO: 2). Some aspects of the present disclosure provides methods for producing a compound of Formula (III) from a compound of Formula (II), or a salt thereof, and malonyl-CoA using an enzyme that is at least 80% identical to PmSPS2 (SEQ ID NO: 3). The structure of a compound of Formula (II) and a structure of a compound of Formula (III) are as follows:

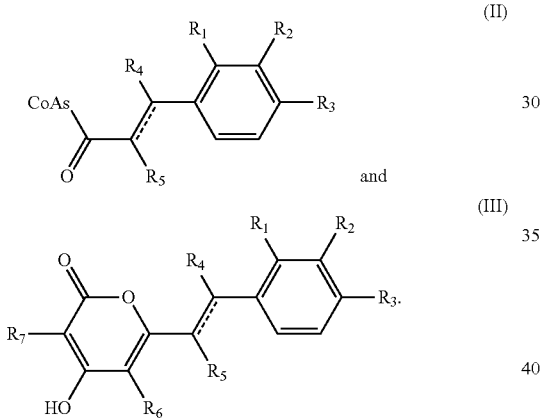

In certain embodiments, the reaction of a compound of Formula (II) with malonyl-CoA to produce a compound of Formula (III) utilizes two or more molar equivalents of malonyl-CoA relative to the compound of Formula (II). In certain embodiments, the reaction of a compound of Formula (II) with malonyl-CoA to produce a compound of Formula (III) is performed in vitro. In certain embodiments, the reaction of a compound of Formula (II) with malonyl-CoA to produce a compound of Formula (III) is performed in vivo.

In certain embodiments, ═══ is a single bond. In certain embodiments, ═══ is a double bond.

In certain embodiments, each of $R_1$, $R_2$, $R_3$, $R_6$, and $R_7$ independently is hydrogen, optionally substituted, cyclic or acyclic aliphatic, or $OR_x$, wherein $R_x$ is hydrogen or optionally substituted, cyclic or acyclic aliphatic. In certain embodiments, $R_1$ is hydrogen. In certain embodiments, $R_2$ is hydrogen. In certain embodiments, $R_3$ is hydrogen. In certain embodiments, $R_1$ is —OH. In certain embodiments, $R_2$ is —OH. In certain embodiments, $R_3$ is —OH. In certain embodiments, $R_1$ is —OCH$_3$. In certain embodiments, $R_2$ is —OCH$_3$. In certain embodiments, $R_3$ is —OCH$_3$. In certain embodiments, $R_1$, $R_2$, and $R_3$ are hydrogen. In certain embodiments, $R_1$, $R_2$, and $R_3$ are —OH. In certain embodiments, $R_1$ and $R_3$ are —OH. In certain embodiments, $R_2$ and $R_3$ are —OH. In certain embodiments, $R_2$ is —OCH$_3$. In certain embodiments, Re is hydrogen. In certain embodiments, $R_6$ is —OH. In certain embodiments, $R_7$ is hydrogen. In certain embodiments, Re is —OH and $R_7$ is hydrogen. In certain embodiments, both Re and $R_7$ are hydrogen.

In certain embodiments, each of $R_4$ and $R_5$ independently is hydrogen or optionally substituted, cyclic or acyclic aliphatic. In certain embodiments, both $R_4$ and $R_5$ are hydrogen.

The methods to produce a compound of Formula (III) include reacting malonyl-CoA with a compound of Formula (II) selected from the group consisting of:

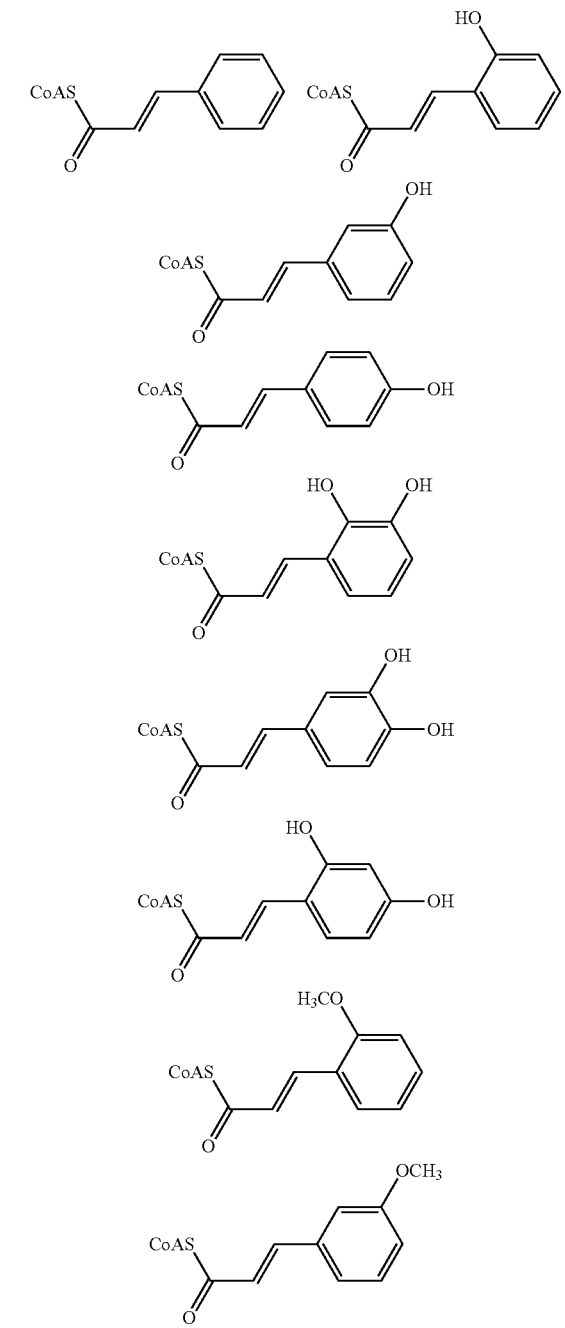

-continued
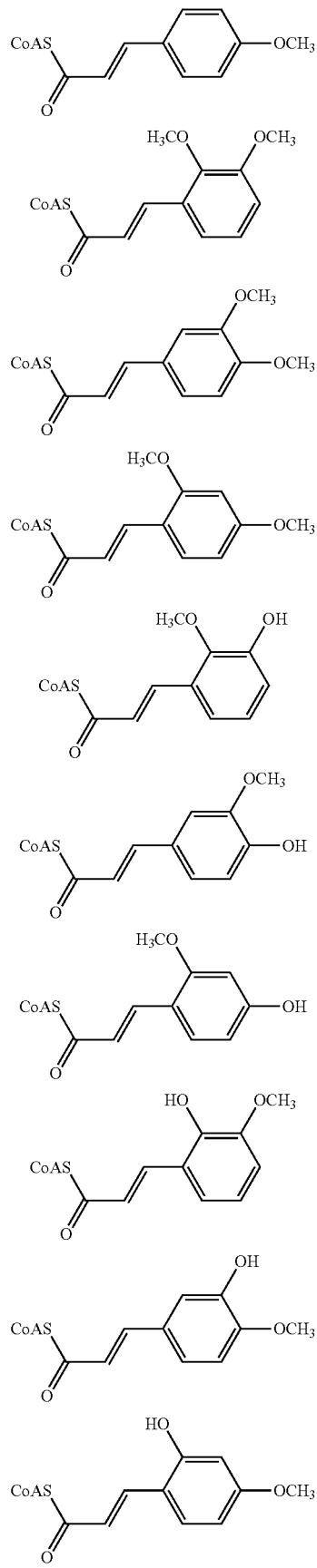
-continued
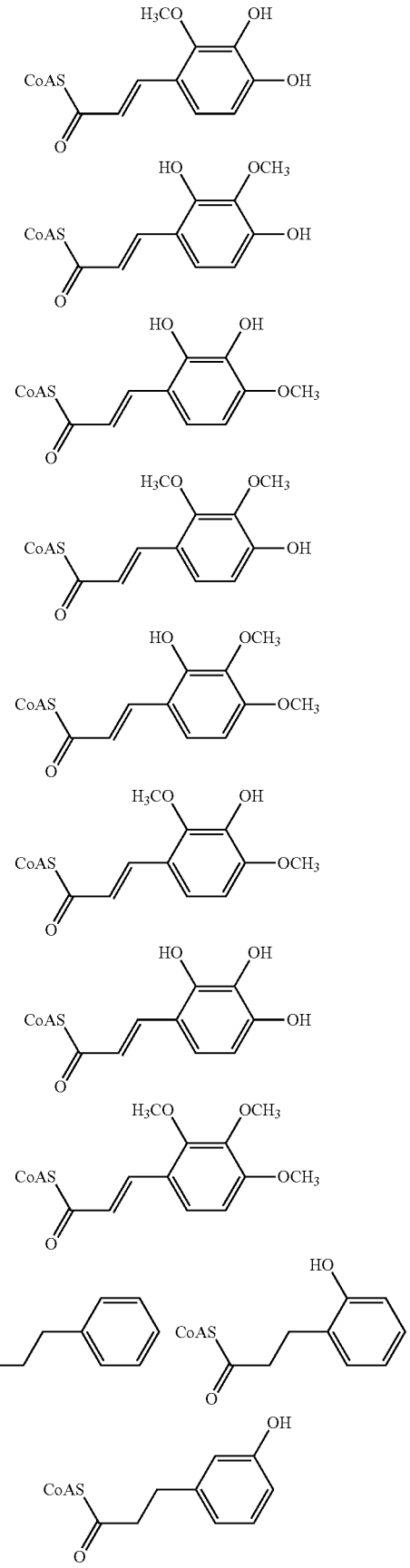

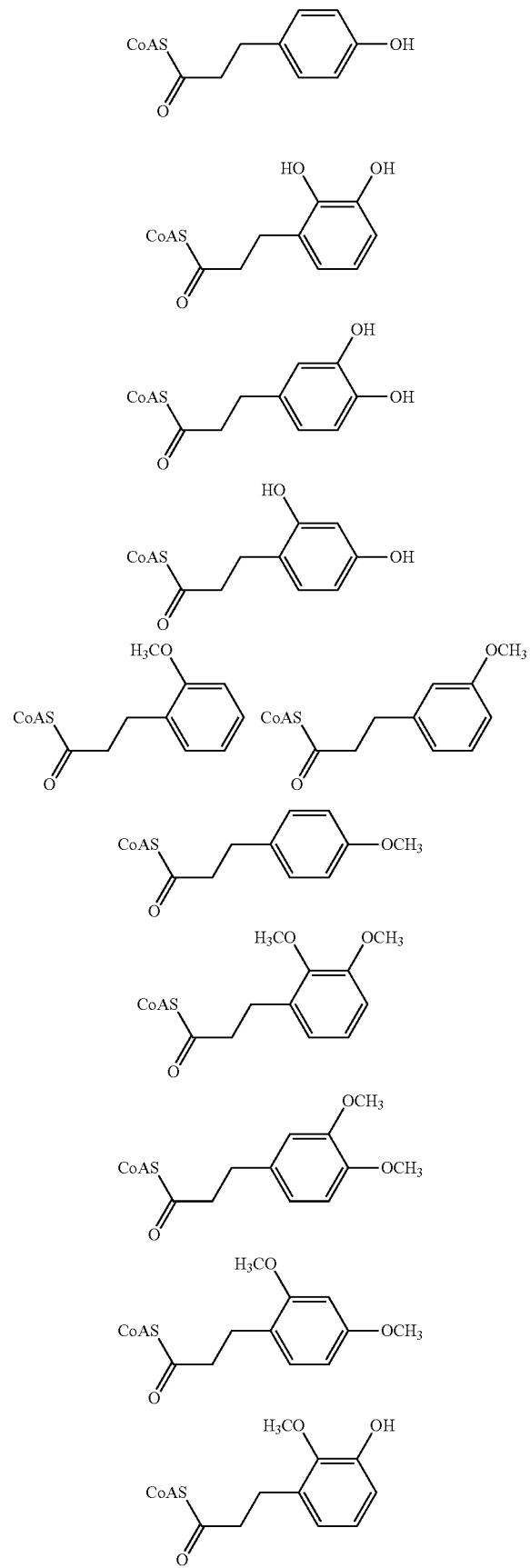
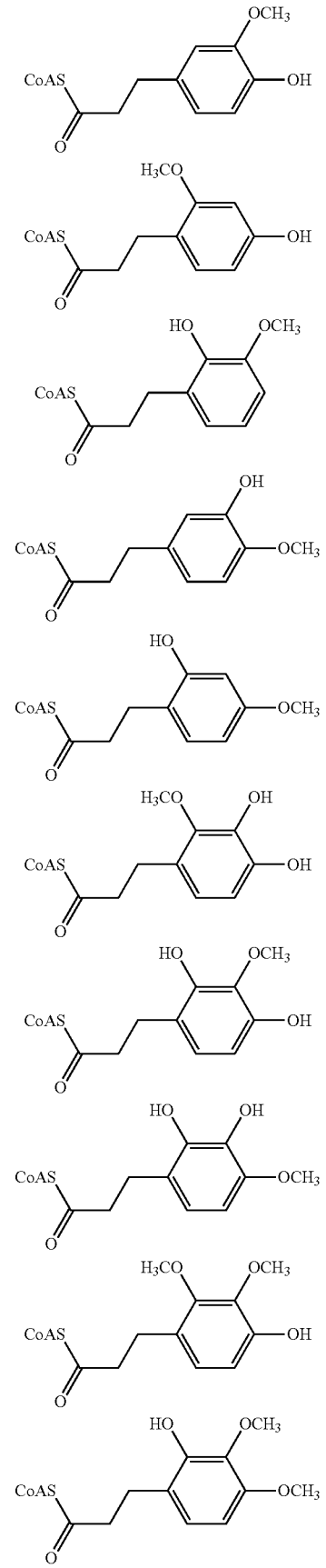

-continued

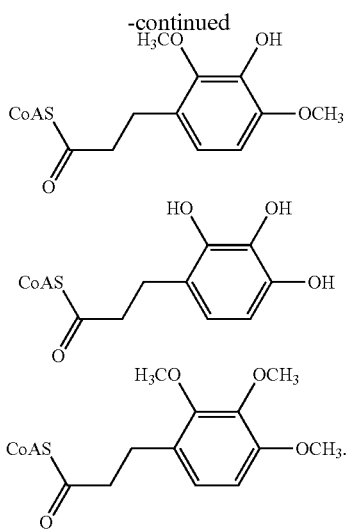

The methods to produce a compound of Formula (III) include culturing cells engineered to express an enzyme that is at least 80% identical to PmSPS1 (SEQ ID NO: 2). The methods to produce a compound of Formula (III) include culturing cells engineered to express an enzyme that is at least 80% identical to PmSPS2 (SEQ ID NO: 3). In certain embodiments, the enzyme is at least 80%, 85%, 90%, 95%, or 100% identical to PmSPS1 (SEQ ID NO: 2). In certain embodiments, the enzyme is at least 80%, 85%, 90%, 95%, or 100% identical to PmSPS2 (SEQ ID NO: 3). In certain embodiments, the enzyme is purified before reacting with a compound of Formula (II). In certain embodiments, the enzyme is partially purified before reacting with a compound of Formula (II).

In certain embodiments, the enzyme that is at least 80% identical to PmSPS1 (SEQ ID NO: 2) is a component in a fusion protein. In certain embodiments, the enzyme that is at least 80% identical to PmSPS2 (SEQ ID NO: 3) is a component in a fusion protein. A fusion protein may be created by joining two or more gene or gene segments that code for separate proteins. Translation of this fusion gene results in a single or multiple polypeptides with functional properties derived from each of the original proteins. A polyfunctional protein is a single protein that has at least two different activities, wherein that functionality is a native biological function or the result of an engineered enzyme fusion. Thus, a fusion protein may include multiple activities such as those described herein for the kavalactone or flavokavain pathway enzymes described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)).

The enzyme that is at least 80% identical to PmSPS1 (SEQ ID NO: 2) is heterologous to the host cell. The enzyme that is at least 80% identical to PmSPS2 (SEQ ID NO: 3) is heterologous to the host cell. In certain embodiments, the enzyme that is at least 80% identical to PmSPS1 (SEQ ID NO: 2) is recombinantly produced. In certain embodiments, the enzyme that is at least 80% identical to PmSPS2 (SEQ ID NO: 3) is recombinantly produced. In certain embodiments, the enzyme that is at least 80% identical to PmSPS1 (SEQ ID NO: 2) is obtained from a wildtype organism. In certain embodiments, the enzyme that is at least 80% identical to PmSPS1 (SEQ ID NO: 2) is obtained from a mutant organism. In certain embodiments, the enzyme that is at least 80% identical to PmSPS1 (SEQ ID NO: 2) is obtained from a genetically-modified organism. In certain embodiments, the enzyme that is at least 80% identical to PmSPS2 (SEQ ID NO: 3) is obtained from a wildtype organism. In certain embodiments, the enzyme that is at least 80% identical to PmSPS2 (SEQ ID NO: 3) is obtained from a mutant organism. In certain embodiments, the enzyme that is at least 80% identical to PmSPS2 (SEQ ID NO: 3) is obtained from a genetically-modified organism. In certain embodiments, the organism is a non-human organism. In certain embodiments, the non-human organism is selected from group consisting of bacteria, yeast, and plant. In certain embodiments, the organism is a plant. In certain embodiments, the plant is *Piper methysticum*.

A nucleic acid encoding the enzyme may be introduced into the cell in a vector (e.g., plasmids, viral vectors, cosmids, and artificial chromosomes). In certain embodiments, the nucleic acid is cDNA derived from the amino acid sequence of the enzyme that is at least 80% identical to PmSPS1 (SEQ ED NO: 2). In certain embodiments, the nucleic acid is cDNA derived from the amino acid sequence of the enzyme that is at least 80% identical to PmSPS2 (SEQ ID NO: 3). In some embodiments multiple cDNAs comprising sequences complementary to different genes (e.g., 2, 3, 4, 5, or more genes) described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)), are introduced into the same cell individually, or together, or as part of a single nucleic acid.

The host cells expressing the enzyme that is at least 80% identical to PmSPS1 (SEQ ID NO: 2) may be prokaryotic cells, such as bacterial cells (e.g., *Escherichia coli* cells), or eukaryotic cells, such as yeast cells or plant cells. The host cells expressing the enzyme that is at least 80% identical to PmSPS2 (SEQ ID NO: 3) may be prokaryotic cells, such as bacterial cells (e.g., *Escherichia coli* cells), or eukaryotic cells, such as yeast cells or plant cells. In certain embodiments, the host cell is capable of expressing two or more kavalactone or flavokavain pathway enzymes described herein. In certain embodiments, the host cell is a bacteria cell and is a wildtype, mutant, recombinant, or genetically engineered form of *Escherichia coli*. In certain embodiments, the host cell is a yeast cell and is a wildtype, mutant, recombinant, or genetically engineered form of *Saccharomyces cerevisiae*. In certain embodiments, the host cell is a plant cell and is a wildtype, mutant, recombinant, or genetically engineered form of *Nicotiana benthamiana*.

In certain embodiments, the method for producing a compound of Formula (III) utilizes a compound of Formula (I), or a salt thereof, as the starting material and comprises the steps: condensing a compound of Formula (I), or a salt thereof, with coenzyme A (CoA) using a recombinant enzyme that is at least 80% identical to Pm4CL1 (SEQ ID NO: 1) to produce a compound of Formula (II); and reacting a compound of Formula (II), or a salt thereof, with malonyl-CoA using an enzyme that is at least 80% identical to PmSPS1 (SEQ ID NO: 2) to produce a compound of Formula (III).

In certain embodiments, the method for producing a compound of Formula (III) utilizes a compound of Formula (I), or a salt thereof, as the starting material and comprises the steps: condensing a compound of Formula (I), or a salt thereof, with coenzyme A (CoA) using a recombinant enzyme that is at least 80% identical to Pm4CL1 (SEQ ID NO: 1) to produce a compound of Formula (II); and reacting a compound of Formula (II), or a salt thereof, with malonyl-CoA using an enzyme that is at least 80% identical to PmSPS2 (SEQ ID NO: 3) to produce a compound of Formula (III).

Production of Methylated
6-styryl-4-hydroxyl-2-pyrone Compounds of
Formula (IV)

Some aspects of the present disclosure provides methods for producing a compound of Formula (IV) from a compound of Formula (III), or a salt thereof, and S-adenosyl-methionine using an enzyme that is at least 80% identical to PmOMT4 (SEQ ID NO: 5). Some aspects of the present disclosure provides methods for producing a compound of Formula (IV) from a compound of Formula (III), or a salt thereof, and S-adenosylmethionine using an enzyme that is at least 80% identical to PmOMT1 (SEQ ID NO: 6). The structure of a compound of Formula (III) and a structure of a compound of Formula (IV) are as follows:

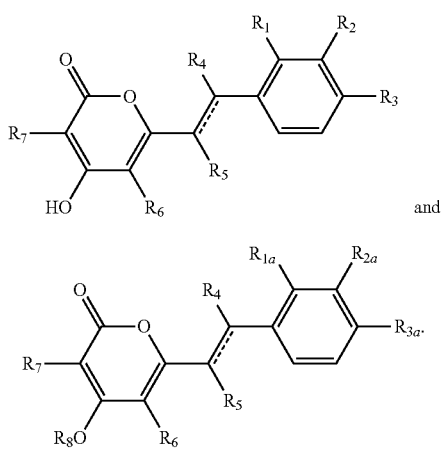

In certain embodiments, the reaction of a compound of Formula (III) with S-adenosylmethionine to produce a compound of Formula (IV) is performed in vitro. In certain, embodiments, the reaction of a compound of Formula (III) with S-adenosylmethionine to produce a compound of Formula (IV) is performed in vivo.

In certain embodiments, ═══ is a single bond. In certain embodiments, ═══ is a double bond.

In certain embodiments, each of $R_1$, $R_2$, $R_3$, $R_{1a}$, $R_{2a}$, $R_{3a}$, $R_6$, and $R_7$ independently is hydrogen, optionally substituted, cyclic or acyclic aliphatic, or —$OR_x$, wherein $R_x$ is hydrogen or optionally substituted, cyclic or acyclic aliphatic. In certain embodiments, $R_1$ is hydrogen. In certain embodiments, $R_2$ is hydrogen. In certain embodiments, $R_3$ is hydrogen. In certain embodiments, $R_1$ is —OH. In certain embodiments, $R_2$ is OH. In certain embodiments, $R_3$ is —OH. In certain embodiments, $R^1$ is —$OCH_3$. In certain embodiments, $R_2$ is —$OCH_3$. In certain embodiments, $R_3$ is —$OCH_3$. In certain embodiments, $R_1$, $R_2$, and $R_3$ are hydrogen. In certain embodiments, $R_1$, $R_2$, and $R_3$ are —OH. In certain embodiments, $R_1$ and $R_3$ are —OH. In certain embodiments, $R_2$ and $R_3$ are —OH. In certain embodiments, $R_2$ is —$OCH_3$. In certain embodiments, $R_6$ is hydrogen. In certain embodiments, $R_6$ is —OH. In certain embodiments, $R_7$ is hydrogen. In certain embodiments, $R_6$ is —OH and $R_7$ is hydrogen. In certain embodiments, both $R_6$ and $R_7$ are hydrogen. In certain embodiments, wherein $R_8$ is —$CH_3$. In certain embodiments, $R_{1a}$ is hydrogen. In certain embodiments, $R_{2a}$ is hydrogen. In certain embodiments, $R_{3a}$ is hydrogen. In certain embodiments, $R_{1a}$ is —OH. In certain embodiments, $R_{2a}$ is OH. In certain embodiments, $R_{3a}$ is —OH. In certain embodiments, $R_{1a}$ is —$OCH_3$. In certain embodiments, $R_{2a}$ is —$OCH_3$. In certain embodiments, $R_{3a}$ is —$OCH_3$. In certain embodiments, $R_{1a}$, $R_{2a}$, and $R_{3a}$ are hydrogen. In certain embodiments, $R_{1a}$, $R_{2a}$, and $R_{3a}$ are —$OCH_3$. In certain embodiments, $R_{1a}$ and $R_{3a}$ are —$OCH_3$. In certain embodiments, $R_{2a}$ and $R_{3a}$ are —$OCH_3$. In certain embodiments, $R_{2a}$ and $R_{3a}$ are —$OCH_3$ and $R_8$ is —$CH_3$. In certain embodiments, $R_{2a}$ and $R_{3a}$ are —OH and $R_8$ is —H.

In certain embodiments, each of $R_4$ and $R_5$ independently is hydrogen or optionally substituted, cyclic or acyclic aliphatic. In certain embodiments, $R_4$ and $R_5$ are hydrogen.

Figure 7:
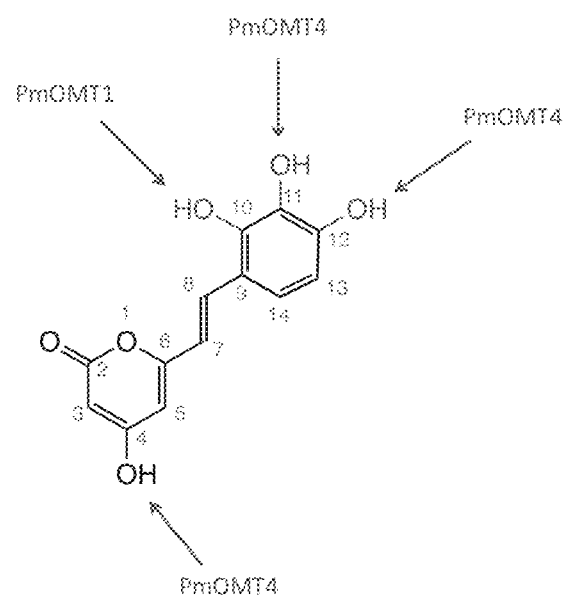
FIG. 7 shows the positions of hydroxyl groups on the 6-styryl-4-hydroxy-2-pyrone backbone that can be methylated by PmOMT4 and PmOMT1.

A compound of Formula (III) can provide different compounds of Formula (IV) depending on the choice to utilize only an enzyme that is at least 80% identical to PmOMT4 (SEQ ID NO: 5), or only an enzyme that is at least 80% identical to PmOMT1 (SEQ ID NO: 6), or both enzymes (FIG. 7). In certain embodiments, $R_8$ is —$CH_3$ when a compound of Formula (III) is reacted with an enzyme that is at least 80% identical to PmOMT4 (SEQ ID NO: 5). In certain embodiments, $R_8$ is hydrogen when a compound of Formula (III) is reacted with an enzyme that is at least 80% identical to PmOMT1 (SEQ ID NO: 6). In certain embodiments, $R_8$ is —$CH_3$ when a compound of Formula (III) is reacted with both an enzyme that is at least 80% identical to PmOMT4 (SEQ ID NO: 5) and an enzyme that is at least 80% identical to PmOMT1 (SEQ ID NO: 6). In certain embodiments, if $R_1$ is —OH, then $R_{1a}$ is —OH when a compound of Formula (III) is reacted with an enzyme that is at least 80% identical to PmOMT4 (SEQ ID NO: 5). In certain embodiments, if $R^1$ is —OH, then $R_{1a}$ is —$OCH_3$ when a compound of Formula (III) is reacted with an enzyme that is at least 80% identical to PmOMT1 (SEQ ID NO: 6). In certain embodiments, if $R_1$ is —OH, then $R_{1a}$ is —$OCH_3$ when a compound of Formula (III) is reacted with both an enzyme that is at least 80% identical to PmOMT4 (SEQ ID NO: 5) and an enzyme that is at least 80% identical to PmOMT1 (SEQ ID NO: 6). In certain embodiments, if $R_2$ is —OH, then $R_{2a}$ is —$OCH_3$ when a compound of Formula (III) is reacted with an enzyme that is at least 80% identical to PmOMT4 (SEQ ID NO: 5). In certain embodiments, if $R_2$ is —OH, then $R_{2a}$ is —OH when a compound of Formula (III) is reacted with an enzyme that is at least 80% identical to PmOMT1 (SEQ ID NO: 6). In certain embodiments, if $R_2$ is —OH, then $R_{2a}$ is —$OCH_3$ when a compound of Formula (III) is reacted with both an enzyme that is at least 80% identical to PmOMT4 (SEQ ID NO: 5) and an enzyme that is at least 80% identical to PmOMT1 (SEQ ID NO: 6). In certain embodiments, if $R_3$ is —OH, then $R_{3a}$ is —$OCH_3$ when a compound of Formula (III) is reacted with an enzyme that is at least 80% identical to PmOMT4 (SEQ ID NO: 5). In certain embodiments, if $R_3$ is —OH, then $R_{3a}$ is —OH when a compound of Formula (III) is reacted with an enzyme that is at least 80% identical to PmOMT1 (SEQ ID NO: 6). In certain embodiments, if $R_3$ is —OH then $R_{3a}$ is —OCH$_3$ when a compound of Formula (III) is reacted with both an enzyme that is at least 80% identical to PmOMT4 (SEQ ID NO: 5) and an enzyme that is at least 80% identical to PmOMT1 (SEQ ID NO: 6).

The methods to produce a compound of Formula (IV) include reacting malonyl-CoA with a compound of Formula (III) selected from the group consisting of:

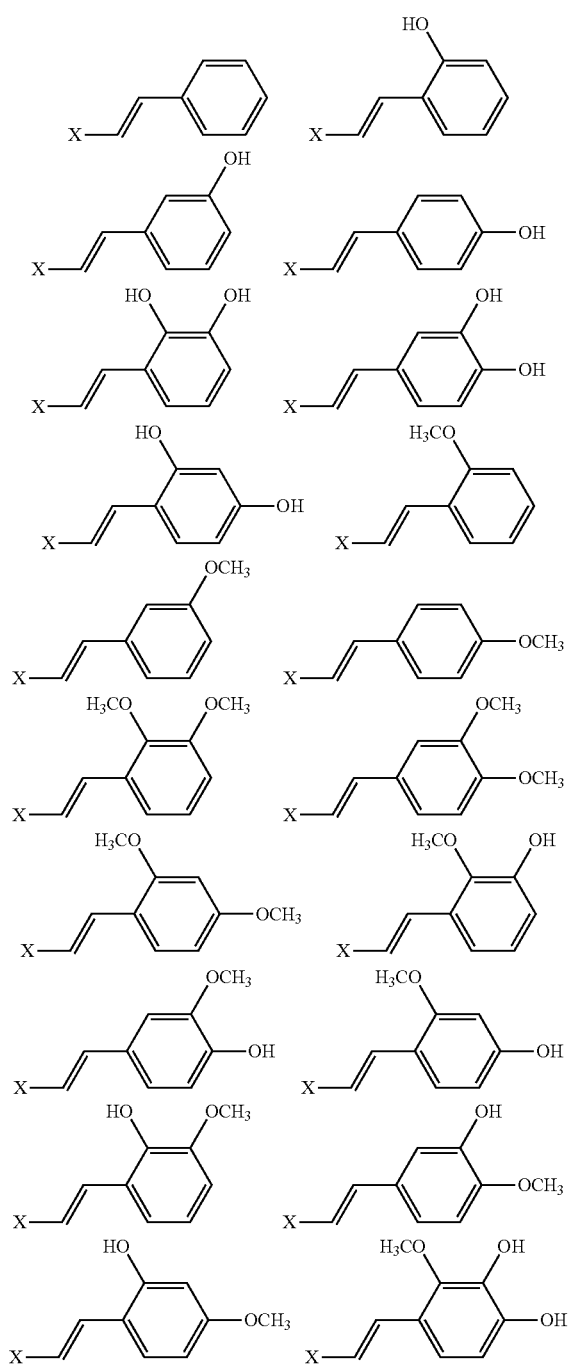

-continued

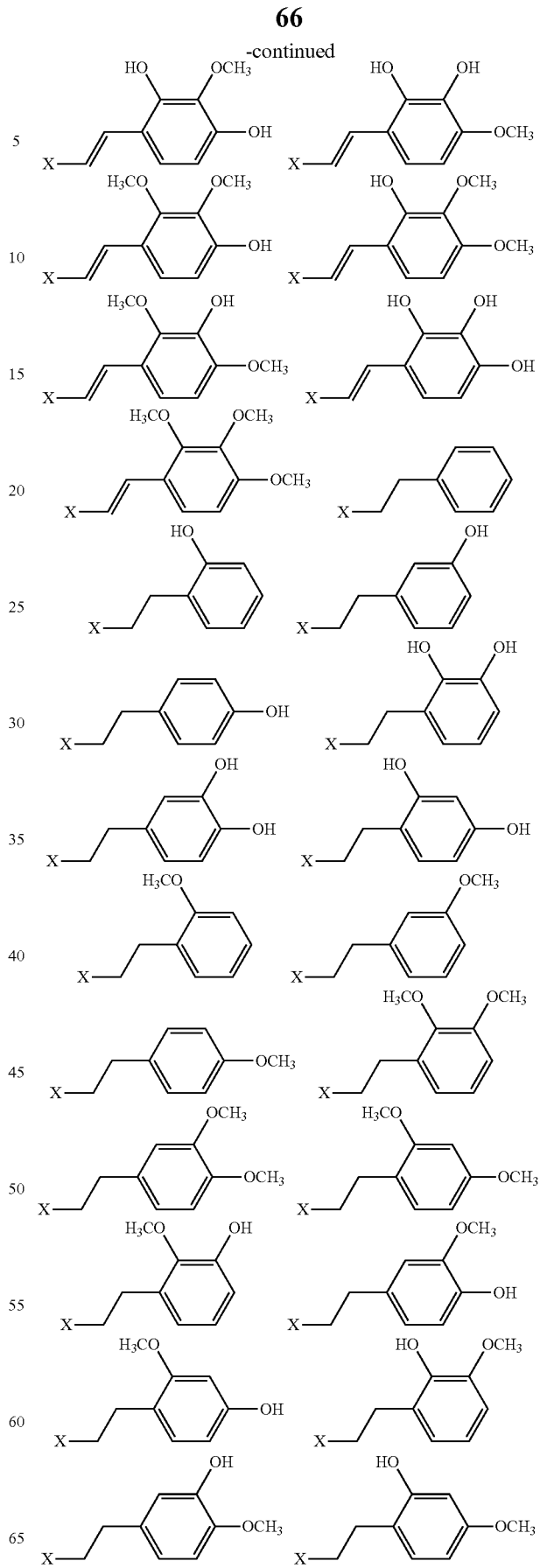

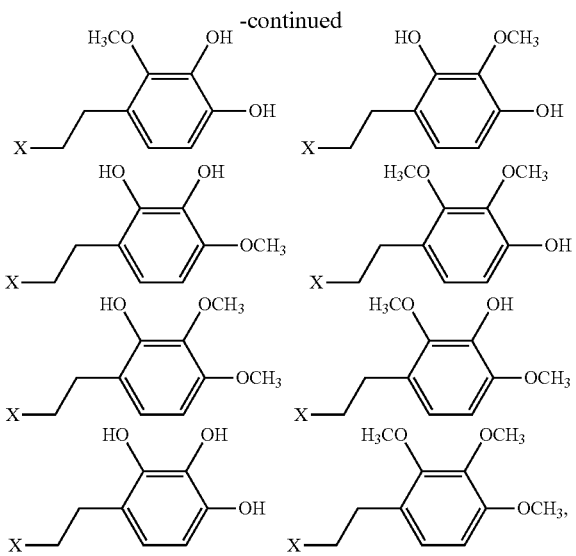

wherein X is

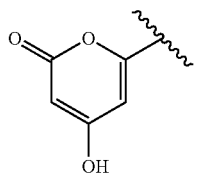

The methods to produce a compound of Formula (IV) include culturing cells engineered to express an enzyme that is at least 80% identical to PmOMT4 (SEQ ID NO: 5). The methods to produce a compound of Formula (IV) include culturing cells engineered to express an enzyme that is at least 80% identical to PmOMT1 (SEQ ID NO: 6). In certain embodiments, the enzyme is at least 80%, 70%, 75%, 80%, 85%, 90%, 95%, or 100% identical to PmOMT4 (SEQ ID NO: 5). In certain embodiments, the enzyme is at least 80%, 85%, 90%, 95%, or 100% identical to PmOMT1 (SEQ ID NO: 6). In certain embodiments, the enzyme is purified before reacting with a compound of Formula (III). In certain embodiments, the enzyme is partially purified before reacting with a compound of Formula (III).

In certain embodiments, the enzyme that is at least 80% identical to PmOMT4 (SEQ ID NO: 5) is a component in a fusion protein. In certain embodiments, the enzyme that is at least 80% identical to PmOMT1 (SEQ ID NO: 6) is a component in a fusion protein. A fusion protein may be created by joining two or more gene or gene segments that code for separate proteins. Translation of this fusion gene results in a single or multiple polypeptides with functional properties derived from each of the original proteins. A polyfunctional protein is a single protein that has at least two different activities, wherein that functionality is a native biological function or the result of an engineered enzyme fusion. Thus, a fusion protein may include multiple activities such as those described herein for the kavalactone or flavokavain pathway enzymes described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)).

The enzyme that is at least 80% identical to PmOMT4 (SEQ ID NO: 5) is heterologous to the host cell. The enzyme that is at least 80% identical to PmOMT1 (SEQ ID NO: 6) is heterologous to the host cell. In certain embodiments, the enzyme that is at least 80% identical to PmOMT4 (SEQ ID NO: 5) is recombinantly produced. In certain embodiments, the enzyme that is at least 80% identical to PmOMT1 (SEQ ID NO: 6) is recombinantly produced. In certain embodiments, the enzyme that is at least 80% identical to PmOMT4 (SEQ ID NO: 5) is obtained from a wildtype organism. In certain embodiments, the enzyme that is at least 80% identical to PmOMT4 (SEQ ID NO: 5) is obtained from a mutant organism. In certain embodiments, the enzyme that is at least 80% identical to PmOMT4 (SEQ ID NO: 5) is obtained from a genetically-modified organism. In certain embodiments, the enzyme that is at least 80% identical to PmOMT1 (SEQ ID NO: 6) is obtained from a wildtype organism. In certain embodiments, the enzyme that is at least 80% identical to PmOMT1 (SEQ ID NO: 6) is obtained from a mutant organism. In certain embodiments, the enzyme that is at least 80% identical to PmOMT1 (SEQ ID NO: 6) is obtained from a genetically-modified organism. In certain embodiments, the organism is a non-human organism. In certain embodiments, the non-human organism is selected from group consisting of bacteria, yeast, and plant. In certain embodiments, the organism is a plant. In certain embodiments, the plant is *Piper methysticum*.

A nucleic acid encoding the enzyme may be introduced into the cell in a vector (e.g., plasmids, viral vectors, cosmids, and artificial chromosomes). In certain embodiments, the nucleic acid is cDNA derived from the amino acid sequence of the enzyme that is at least 80% identical to PmOMT4 (SEQ ID NO: 5). In certain embodiments, the nucleic acid is cDNA derived from the amino acid sequence of the enzyme that is at least 80% identical to PmOMT1 (SEQ ID NO: 6). In some embodiments multiple cDNAs comprising sequences complementary to different genes (e.g., 2, 3, 4, 5, or more genes) described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)), are introduced into the same cell individually, or together, or as part of a single nucleic acid.

The host cells expressing the enzyme that is at least 80% identical to PmOMT4 (SEQ ID NO: 5) may be prokaryotic cells, such as bacterial cells (e.g., *Escherichia coli* cells), or eukaryotic cells, such as yeast cells or plant cells. The host cells expressing the enzyme that is at least 80% identical to PmOMT1 (SEQ ID NO: 6) may be prokaryotic cells, such as bacterial cells (e.g., *Escherichia coli* cells), or eukaryotic cells, such as yeast cells or plant cells. In certain embodiments, the host cell is capable of expressing two or more kavalactone or flavokavain pathway enzymes described herein. In certain embodiments, the host cell is a bacteria cell and is a wildtype, mutant, recombinant, or genetically engineered form of *Escherichia coli*. In certain embodiments, the host cell is a yeast cell and is a wildtype, mutant, recombinant, or genetically engineered form of *Saccharomyces cerevisiae*. In certain embodiments, the host cell is a plant cell and is a wildtype, mutant, recombinant, or genetically engineered form of *Nicotiana benthamiana*.

In certain embodiments, the method for producing a compound of Formula (IV) utilizes a compound of Formula (I), or a salt thereof, as the starting material and comprises the steps: condensing a compound of Formula (I), or a salt thereof, with coenzyme A (CoA) using an enzyme that is at least 80% identical to Pm4CL1 (SEQ ID NO: 1) to produce a compound of Formula (II); reacting a compound of Formula (II), or a salt thereof, with malonyl-CoA using an enzyme that is at least 80% identical to PmSPS1 (SEQ ID NO: 2) to produce a compound of Formula (III); and alkylating a compound of Formula (III), or a salt thereof, with S-adenosylmethionine using an enzyme that at least 80% identical to PmOMT4 (SEQ ID NO: 5) to produce a compound of Formula (IV).

In certain embodiments, the method for producing a compound of Formula (IV) utilizes a compound of Formula (I), or a salt thereof, as the starting material and comprises the steps: condensing a compound of Formula (I), or a salt thereof, with coenzyme A (CoA) using an enzyme that is at least 80% identical to Pm4CL1 (SEQ ID NO: 1) to produce a compound of Formula (II); reacting a compound of Formula (II), or a salt thereof, with malonyl-CoA using an enzyme that is at least 80% identical to PmSPS1 (SEQ ID NO: 2) to produce a compound of Formula (III); and alkylating a compound of Formula (III), or a salt thereof, with S-adenosylmethionine using an enzyme that at least 80% identical to PmOMT1 (SEQ ID NO: 6) to produce a compound of Formula (IV).

In certain embodiments, the method for producing a compound of Formula (IV) utilizes a compound of Formula (I), or a salt thereof, as the starting material and comprises the steps: condensing a compound of Formula (I), or a salt thereof, with coenzyme A (CoA) using an enzyme that is at least 80% identical to Pm4CL1 (SEQ ID NO: 1) to produce a compound of Formula (II); reacting a compound of Formula (II), or a salt thereof, with malonyl-CoA using an enzyme that is at least 80% identical to PmSPS2 (SEQ ID NO: 3) to produce a compound of Formula (III); and alkylating a compound of Formula (III), or a salt thereof, with S-adenosylmethionine using an enzyme that at least 80% identical to PmOMT4 (SEQ ID NO: 5) to produce a compound of Formula (IV).

In certain embodiments, the method for producing a compound of Formula (IV) utilizes a compound of Formula (I), or a salt thereof, as the starting material and comprises the steps: condensing a compound of Formula (I), or a salt thereof, with coenzyme A (CoA) using an enzyme that is at least 80% identical to Pm4CL1 (SEQ ID NO: 1) to produce a compound of Formula (II); reacting a compound of Formula (II), or a salt thereof, with malonyl-CoA using an enzyme that is at least 80% identical to PmSPS2 (SEQ ID NO: 3) to produce a compound of Formula (III); and alkylating a compound of Formula (III), or a salt thereof, with S-adenosylmethionine using an enzyme that at least 80% identical to PmOMT1 (SEQ ID NO: 6) to produce a compound of Formula (IV).

Production of
6-styryl-4-hydroxyl-5,6-dihydro-2-pyrone
Compounds of Formula (V)

Some aspects of the present disclosure provides methods for producing a compound of Formula (V) from a compound of Formula (IV), or a salt thereof, and a reducing agent (i.e., NADPH or NADH) using an enzyme that is at least 80% identical to PmRDCT10 (SEQ ID NO: 8), wherein:

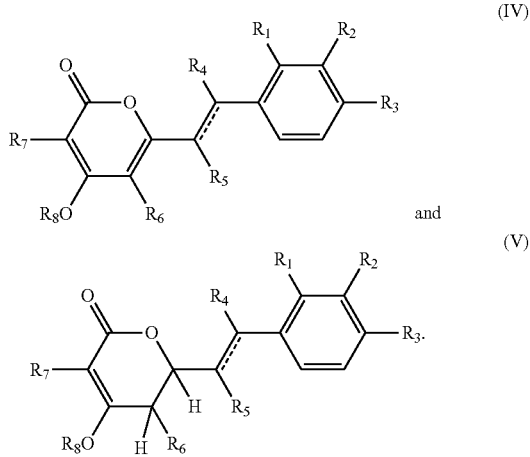

In certain, embodiments, the reduction reaction of a compound of Formula (IV) with NADPH to produce a compound of Formula (V) occurs in vitro. In certain embodiments, the reduction reaction of a compound of Formula (IV) with NADPH to produce a compound of Formula (V) occurs in vivo. In certain, embodiments, the reduction reaction of a compound of Formula (IV) with NADH to produce a compound of Formula (V) occurs in vitro. In certain embodiments, the reduction reaction of a compound of Formula (IV) with NADH to produce a compound of Formula (V) occurs in vivo.

In certain embodiments, $=\!=\!=$ is a single bond. In certain embodiments, $=\!=\!=$ is a double bond.

In certain embodiments, each of Ra, $R_2$, $R_3$, $R_6$, and $R_7$ independently is hydrogen, optionally substituted, cyclic or acyclic aliphatic, or $OR_x$, wherein $R_x$ is hydrogen or optionally substituted, cyclic or acyclic aliphatic. In certain embodiments, $R_1$ is hydrogen. In certain embodiments, $R_2$ is hydrogen. In certain embodiments, $R_3$ is hydrogen. In certain embodiments, $R_1$ is —OH. In certain embodiments, $R_2$ is OH. In certain embodiments, $R_3$ is —OH. In certain embodiments, $R_1$ is —OCH$_3$. In certain embodiments, $R_2$ is —OCH$_3$. In certain embodiments, $R_3$ is —OCH$_3$. In certain embodiments, $R_1$, $R_2$, and $R_3$ are hydrogen. In certain embodiments, $R_1$, $R_2$, and $R_3$ are —OH. In certain embodiments, $R_1$ and $R_3$ are —OH. In certain embodiments, $R_2$ and $R_3$ are —OH. In certain embodiments, $R_2$ is —OCH$_3$. In certain embodiments, $R_6$ is hydrogen. In certain embodiments, $R_6$ is —OH. In certain embodiments, $R_7$ is hydrogen. In certain embodiments, $R_6$ is —OH and $R_7$ is hydrogen. In certain embodiments, both $R_6$ and $R_7$ are hydrogen. In certain embodiments, $R_8$ is hydrogen. In certain embodiments, wherein $R_8$ is —CH$_3$. $R_1$, $R_2$, and $R_3$ are —OCH$_3$. In certain embodiments, $R_1$ and $R_3$ are —OCH$_3$. In certain embodiments, $R_2$ and $R_3$ are —OCH$_3$. In certain embodiments, $R_2$ and $R_3$ are —OCH$_3$ and $R_8$ is —CH$_3$. In certain embodiments, $R_2$ and $R_3$ are —OH and $R_8$ is —H.

In certain embodiments, each of $R_4$ and $R_5$ independently is hydrogen or optionally substituted, cyclic or acyclic aliphatic. In certain embodiments, $R_4$ and $R_5$ are hydrogen.

The methods to produce a compound of Formula (V) include reacting NADPH or NADH with a compound of Formula (IV) selected from the group consisting of:

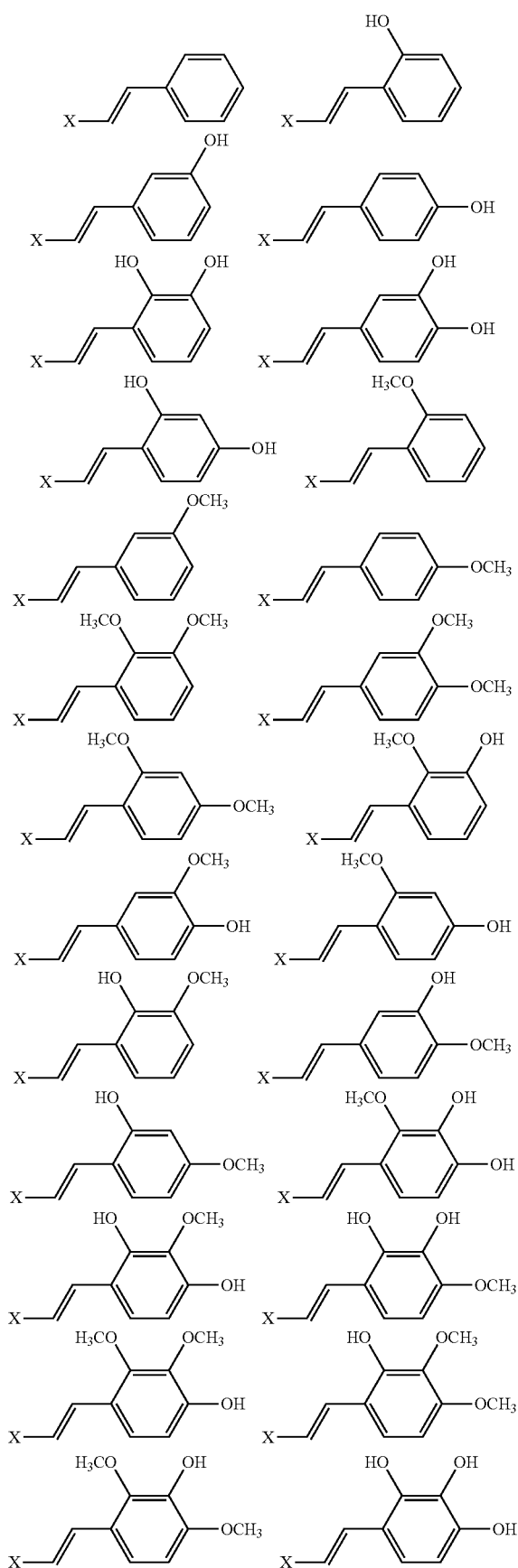
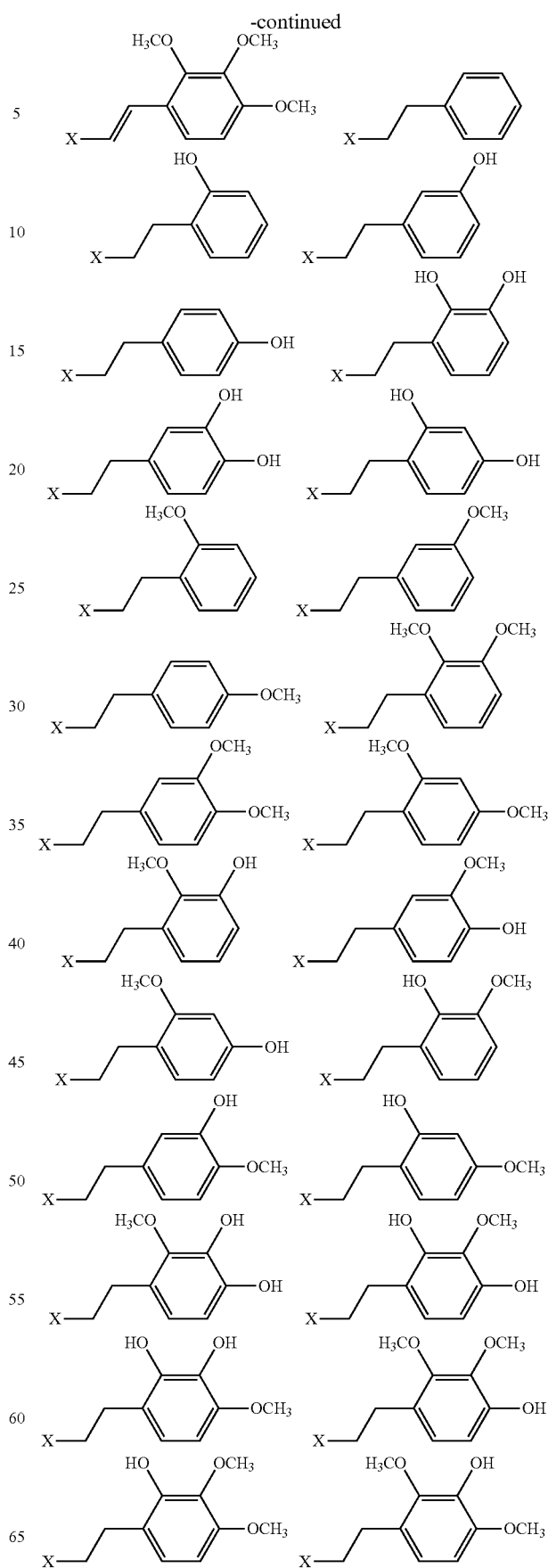

-continued

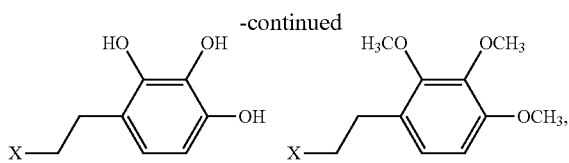

wherein X is

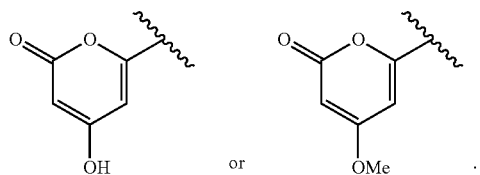 [SMILES: *c1cc(O)cc(=O)o1 ; *c1cc(OC)cc(=O)o1]

The methods to produce a compound of Formula (V) include culturing cells engineered to express an enzyme that is at least 80% identical to PmRDCT10 (SEQ ID NO: 8). In certain embodiments, the enzyme is at least 80%, 85%, 90%, 95%, or 100% identical to PmRDCT10 (SEQ ID NO: 8). In certain embodiments, the enzyme is purified before reacting with a compound of Formula (IV). In certain embodiments, the enzyme is partially purified before reacting with a compound of Formula (IV).

In certain embodiments, the enzyme that is at least 80% identical to PmRDCT10 (SEQ ID NO: 8) is a component in a fusion protein. A fusion protein may be created by joining two or more gene or gene segments that code for separate proteins. Translation of this fusion gene results in a single or multiple polypeptides with functional properties derived from each of the original proteins. A polyfunctional protein is a single protein that has at least two different activities, wherein that functionality is a native biological function or the result of an engineered enzyme fusion. Thus, a fusion protein may include multiple activities such as those described herein for the kavalactone or flavokavain pathway enzymes described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)).

The enzyme that is at least 80% identical to PmRDCT10 (SEQ ID NO: 8) is heterologous to the host cell. In certain embodiments, the enzyme that is at least 80% identical to PmRDCT10 (SEQ ID NO: 8) is recombinantly produced. In certain embodiments, the enzyme that is at least 80% identical to PmRDCT10 (SEQ ID NO: 8) is obtained from a wildtype organism. In certain embodiments, the enzyme that is at least 80% identical to PmRDCT10 (SEQ ID NO: 8) is obtained from a mutant organism. In certain embodiments, the enzyme that is at least 80% identical to PmRDCT10 (SEQ ID NO: 8) is obtained from a genetically-modified organism. In certain embodiments, the organism is a non-human organism. In certain embodiments, the non-human organism is selected from group consisting of bacteria, yeast, and plant. In certain embodiments, the organism is a plant. In certain embodiments, the plant is *Piper methysticum*.

A nucleic acid encoding the enzyme may be introduced into the cell in a vector (e.g., plasmids, viral vectors, cosmids, and artificial chromosomes). In certain embodiments, the nucleic acid is cDNA derived from the amino acid sequence of the enzyme that is at least 80% identical to PmRDCT10 (SEQ ID NO: 8). In some embodiments multiple cDNAs comprising sequences complementary to different genes (e.g., 2, 3, 4, 5, or more genes) described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)), are introduced into the same cell individually, or together, or as part of a single nucleic acid.

The host cells expressing the enzyme that is at least 80% identical to PmRDCT10 (SEQ ID NO: 8) may be prokaryotic cells, such as bacterial cells (e.g., *Escherichia coli* cells), or eukaryotic cells, such as yeast cells or plant cells. In certain embodiments, the host cell is capable of expressing two or more kavalactone or flavokavain pathway enzymes described herein. In certain embodiments, the host cell is a bacteria cell and is a wildtype, mutant, recombinant, or genetically engineered form of *Escherichia coli*. In certain embodiments, the host cell is a yeast cell and is a wildtype, mutant, recombinant, or genetically engineered form of *Saccharomyces cerevisiae*. In certain embodiments, the host cell is a plant cell and is a wildtype, mutant, recombinant, or genetically engineered form of *Nicotiana benthamiana*.

Production of 6-styryl-4-hydroxyl-2-pyrone Compounds with a Methylenedioxy Bridge of Formula (VI)

Some aspects of the present disclosure provides methods for producing a compound of Formula (VI) from a compound of Formula (IV), or a salt thereof, and a reducing agent (i.e., NADPH or NADH) using an enzyme that is at least 80% identical to PmMDB1 (SEQ ID NO: 7), wherein:

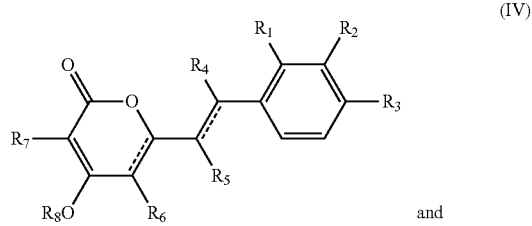

(IV)

and

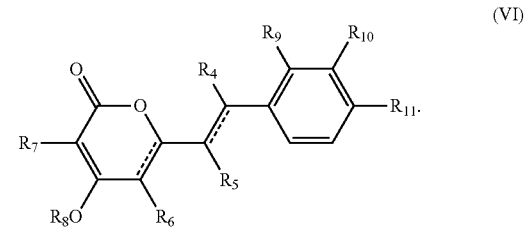

(VI)

In certain, embodiments, the reduction reaction of a compound of Formula (IV) with NADPH to produce a compound of Formula (VI) occurs in vitro. In certain embodiments, the reduction reaction of a compound of Formula (IV) with NADPH to produce a compound of Formula (VI) occurs in vivo. In certain, embodiments, the reduction reaction of a compound of Formula (IV) with NADH to produce a compound of Formula (VI) occurs in vitro. In certain embodiments, the reduction reaction of a compound of Formula (IV) with NADH to produce a compound of Formula (VI) occurs in vivo.

In certain embodiments, ═══ is a single bond. In certain embodiments, ═══ is a double bond.

In certain embodiments, each of $R_1$, $R_2$, $R_3$, $R_6$, $R_7$, $R_9$, $R_{10}$, and $R_{11}$ independently is hydrogen, optionally substituted, cyclic or acyclic aliphatic, or $OR_x$, or $R_9$ and $R_{10}$ are combined to form a ring, or $R_{10}$ and $R_{11}$ are combined to form a ring, wherein $R_x$ is hydrogen or optionally substituted, cyclic or acyclic aliphatic. In certain embodiments, $R_1$ is hydrogen. In certain embodiments, $R_2$ is hydrogen. In certain embodiments, $R_3$ is hydrogen. In certain embodiments, $R_1$ is —OH. In certain embodiments, $R_2$ is —OH. In certain embodiments, $R_3$ is —OH. In certain embodiments, $R_1$ is —OCH$_3$. In certain embodiments, $R_2$ is —OCH$_3$. In certain embodiments, $R_3$ is —OCH$_3$. In certain embodiments, $R_1$, $R_2$, and $R_3$ are hydrogen. In certain embodiments, $R_1$, $R_2$, and $R_3$ are —OH. In certain embodiments, $R_1$ and $R_3$ are —OH. In certain embodiments, $R_2$ and $R_3$ are —OH. In certain embodiments, $R_2$ is —OCH$_3$. In certain embodiments, $R_6$ is hydrogen. In certain embodiments, $R_6$ is —OH. In certain embodiments, $R_7$ is hydrogen. In certain embodiments, $R_6$ is —OH and $R_7$ is hydrogen. In certain embodiments, both $R_6$ and $R_7$ are hydrogen. In certain embodiments, $R_8$ is hydrogen. In certain embodiments, wherein $R_8$ is —CH$_3$. In certain embodiments, $R_9$ and $R_{10}$ are combined to form a methylenedioxy cyclic moiety —OCH$_2$O— and $R_{11}$ is hydrogen. In certain embodiments, $R_9$ and $R_{10}$ are combined to form a methylenedioxy cyclic moiety —OCH$_2$O— and $R_{11}$ is optionally substituted, cyclic or acyclic aliphatic. In certain embodiments, $R_9$ and $R_{10}$ are combined to form a methylenedioxy cyclic moiety —OCH$_2$O— and $R_{11}$ is —OH. In certain embodiments, $R_9$ and $R_{10}$ are combined to form a methylenedioxy cyclic moiety —OCH$_2$O— and $R_{11}$ is —OCH$_3$. In certain embodiments, $R_{10}$ and $R_{11}$ are combined to form a methylenedioxy cyclic moiety —OCH$_2$O— and $R_9$ is hydrogen. In certain embodiments, $R_{10}$ and $R_{11}$ are combined to form a methylenedioxy cyclic moiety —OCH$_2$O— and $R_9$ is optionally substituted, cyclic or acyclic aliphatic. In certain embodiments, $R_{10}$ and $R_{11}$ are combined to form a methylenedioxy cyclic moiety —OCH$_2$O— and $R_9$ is —OH. In certain embodiments, $R_{10}$ and $R_{11}$ are combined to form a methylenedioxy cyclic moiety —OCH$_2$O— and $R_9$ is —OCH$_3$. In certain embodiments, $R_1$ is —OH, $R_2$ is —OCH$_3$, and $R_9$ and $R_{10}$ are combined to form a methylenedioxy cyclic moiety —OCH$_2$O—. In certain embodiments, $R_1$ is —OCH$_3$, $R_2$ is —OH, and $R_9$ and $R_{10}$ are combined to form a methylenedioxy cyclic moiety —OCH$_2$O—. In certain, embodiments, $R_2$ is —OH, $R_3$ is —OCH$_3$, and $R_{10}$ and $R_{11}$ are combined to form a methylenedioxy cyclic moiety —OCH$_2$O—. In certain embodiments, $R_2$ is —OCH$_3$, $R_3$ is —OH, and $R_{10}$ and $R_{11}$ are combined to form a methylenedioxy cyclic moiety —OCH$_2$O—.

In certain embodiments, each of $R_4$ and $R_5$ independently is hydrogen or optionally substituted, cyclic or acyclic aliphatic. In certain embodiments, $R_4$ and $R_5$ are hydrogen.

The methods to produce a compound of Formula (VI) include reacting NADPH or NADH with a compound of Formula (IV) selected from the group consisting of:

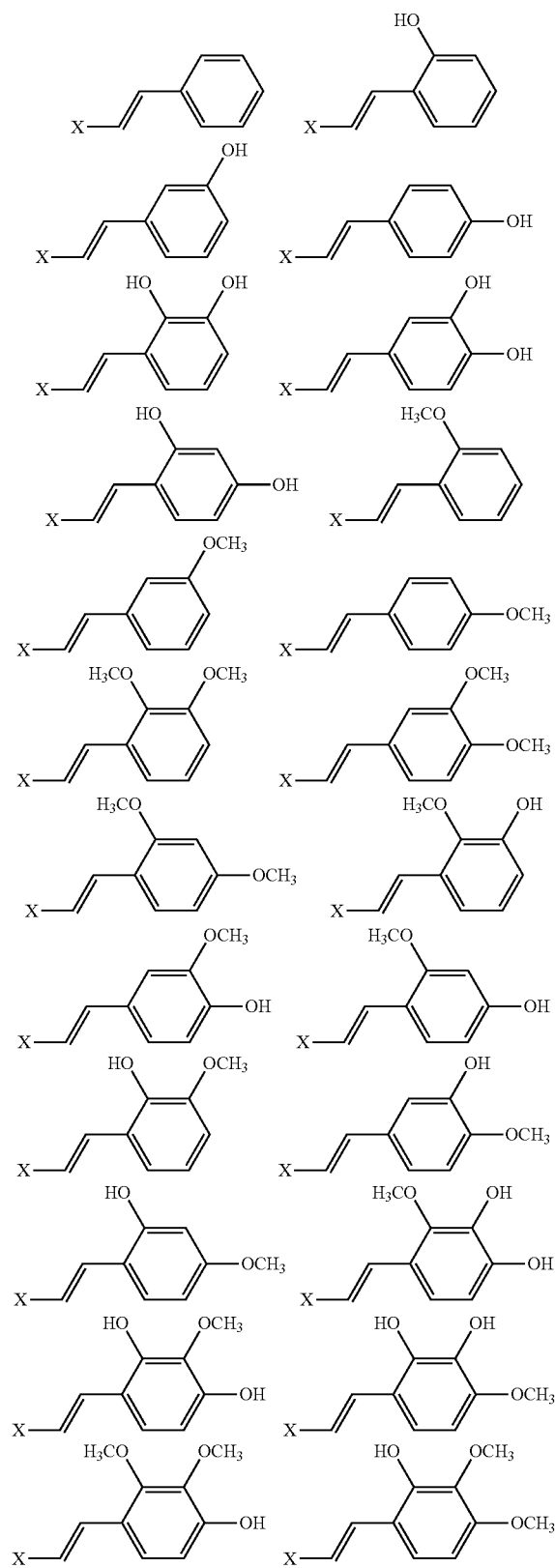

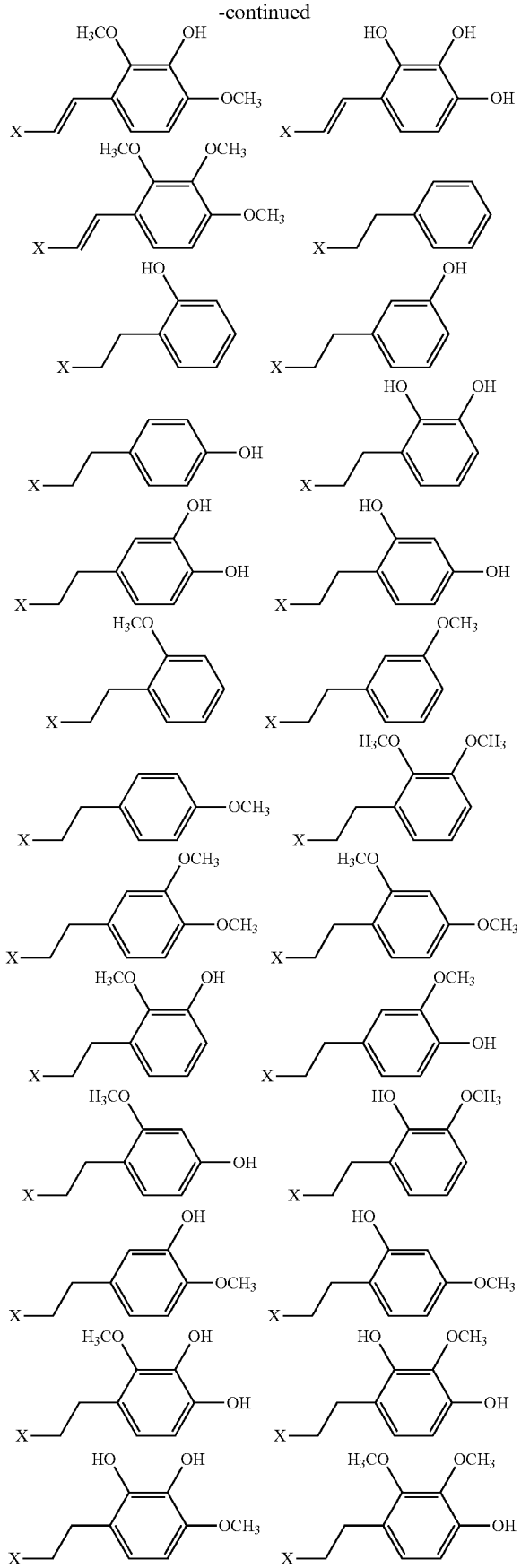

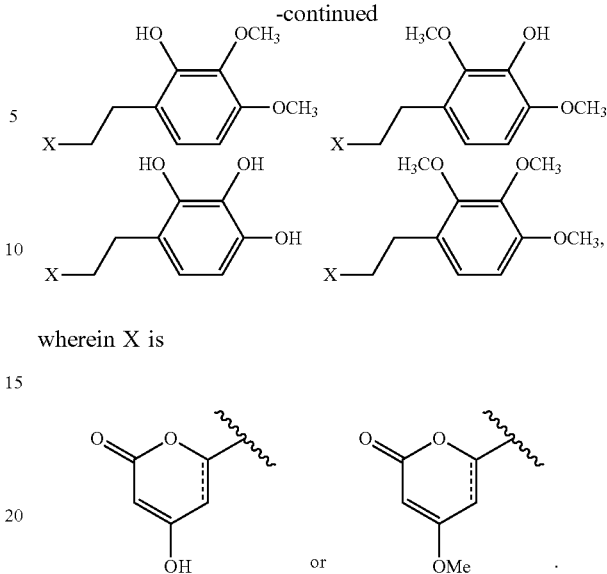

wherein X is

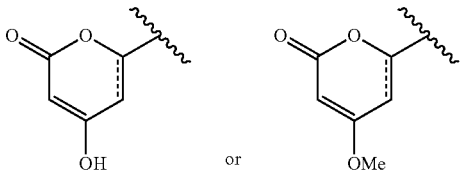

The methods to produce a compound of Formula (VI) include culturing cells engineered to express an enzyme that is at least 80% identical to PmMDB1 (SEQ ID NO: 7). In certain embodiments, the enzyme is at least 80%, 85%, 90%, 95%, or 100% identical to PmMDB1 (SEQ ID NO: 7). In certain embodiments, the enzyme is purified before reacting with a compound of Formula (IV). In certain embodiments, the enzyme is partially purified before reacting with a compound of Formula (IV).

In certain embodiments, the enzyme that is at least 80% identical to PmMDB1 (SEQ ID NO: 7) is a component in a fusion protein. A fusion protein may be created by joining two or more gene or gene segments that code for separate proteins. Translation of this fusion gene results in a single or multiple polypeptides with functional properties derived from each of the original proteins. A polyfunctional protein is a single protein that has at least two different activities, wherein that functionality is a native biological function or the result of an engineered enzyme fusion. Thus, a fusion protein may include multiple activities such as those described herein for the kavalactone or flavokavain pathway enzymes described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)).

The enzyme that is at least 80% identical to PmMDB1 (SEQ ID NO: 7) is heterologous to the host cell. In certain embodiments, the enzyme that is at least 80% identical to PmMDB1 (SEQ ID NO: 7) is recombinantly produced. In certain embodiments, the enzyme that is at least 80% identical to PmMDB1 (SEQ ID NO: 7) is obtained from a wildtype organism. In certain embodiments, the enzyme that is at least 80% identical to PmMDB1 (SEQ ID NO: 7) is obtained from a mutant organism. In certain embodiments, the enzyme that is at least 80% identical to PmMDB1 (SEQ ID NO: 7) is obtained from a genetically-modified organism.

In certain embodiments, the organism is a non-human organism. In certain embodiments, the non-human organism is selected from group consisting of bacteria, yeast, and plant. In certain embodiments, the organism is a plant. In certain embodiments, the plant is *Piper methysticum*.

A nucleic acid encoding the enzyme may be introduced into the cell in a vector (e.g., plasmids, viral vectors, cosmids, and artificial chromosomes). In certain embodiments, the nucleic acid is cDNA derived from the amino acid sequence of the enzyme that is at least 80% identical to PmMDB1 (SEQ ID NO: 7). In some embodiments multiple cDNAs comprising sequences complementary to different genes (e.g., 2, 3, 4, 5, or more genes) described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)), are introduced into the same cell individually, or together, or as part of a single nucleic acid.

The host cells expressing the enzyme that is at least 80% identical to PmMDB1 (SEQ ID NO: 7) may be prokaryotic cells, such as bacterial cells (e.g., *Escherichia coli* cells), or eukaryotic cells, such as yeast cells or plant cells. In certain embodiments, the host cell is capable of expressing two or more kavalactone or flavokavain pathway enzymes described herein. In certain embodiments, the host cell is a bacteria cell and is a wildtype, mutant, recombinant, or genetically engineered form of *Escherichia coli*. In certain embodiments, the host cell is a yeast cell and is a wildtype, mutant, recombinant, or genetically engineered form of *Saccharomyces cerevisiae*. In certain embodiments, the host cell is a plant cell and is a wildtype, mutant, recombinant, or genetically engineered form of *Nicotiana benthamiana*.

Production of Chalcone Compounds of Formula (VII)

Some aspects of the present disclosure provides methods for producing a compound of Formula (VII) from a compound of Formula (II), or a salt thereof, and malonyl-CoA using an enzyme that is at least 80% identical to PmCHS (SEQ ID NO: 4), wherein:

In certain embodiments, the reaction of a compound of Formula (II) with malonyl-CoA to produce a compound of Formula (VII) utilizes three or more molar equivalents of malonyl-CoA relative to the compound of Formula (II). In certain embodiments, the reaction of a compound of Formula (II) with malonyl-CoA to produce a compound of Formula (VII) occurs in vitro. In certain embodiments, the reaction of a compound of Formula (II) with malonyl-CoA to produce a compound of Formula (VII) occurs in vivo.

In certain embodiments, ═══ is a single bond. In certain embodiments, ═══ is a double bond.

In certain embodiments, each of $R_1$, $R_2$, $R_3$, $R_6$, and $R_7$ independently is hydrogen, optionally substituted, cyclic or acyclic aliphatic, or $OR_x$, wherein $R_x$ is hydrogen or optionally substituted, cyclic or acyclic aliphatic. In certain embodiments, $R_1$ is hydrogen. In certain embodiments, $R_2$ is hydrogen. In certain embodiments, $R_3$ is hydrogen. In certain embodiments, $R_1$ is —OH. In certain embodiments, $R_2$ is —OH. In certain embodiments, $R_3$ is —OH. In certain embodiments, $R_1$ is —OCH$_3$. In certain embodiments, $R_2$ is —OCH$_3$. In certain embodiments, $R_3$ is —OCH$_3$. In certain embodiments, $R_1$, $R_2$, and $R_3$ are hydrogen. In certain embodiments, $R_1$ and $R_2$ are hydrogen and $R_3$ is —OH. In certain embodiments, $R_1$ and $R_2$ are hydrogen and $R_3$ is —OCH$_3$. In certain embodiments, $R_6$ is hydrogen. In certain embodiments, $R_7$ is hydrogen.

In certain embodiments, each of $R_4$ and $R_5$ independently is hydrogen or optionally substituted, cyclic or acyclic aliphatic. In certain embodiments, $R_4$ and $R_5$ are hydrogen.

The methods to produce a compound of Formula (VII) include reacting malonyl-CoA with a compound of Formula (II) selected from the group consisting of:

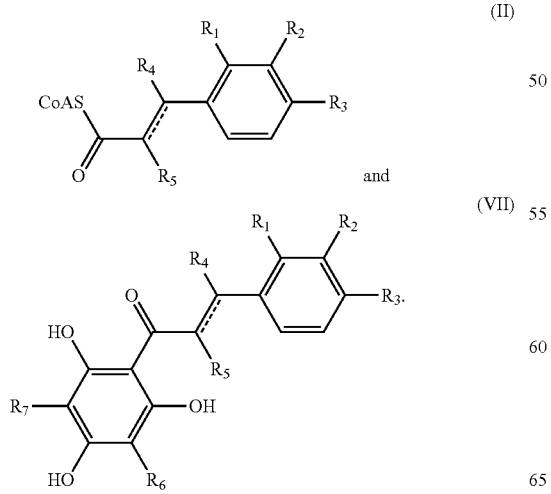

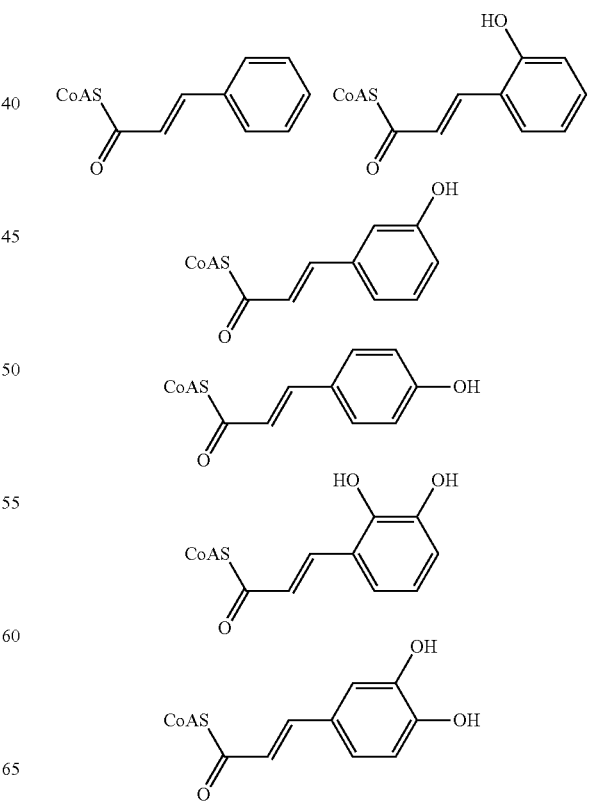

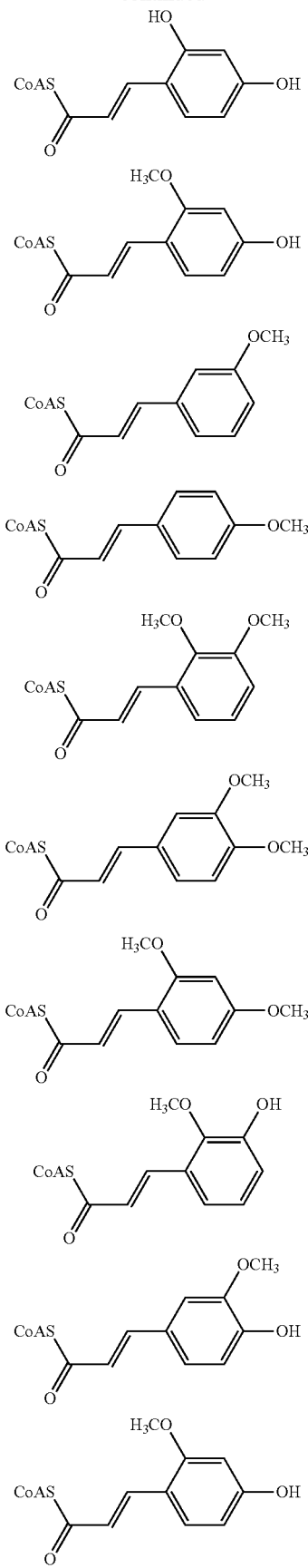
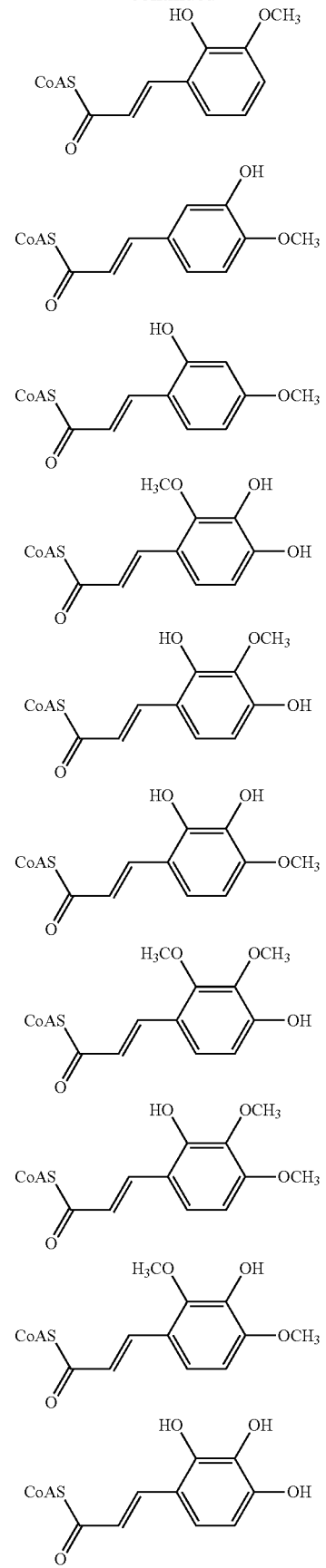

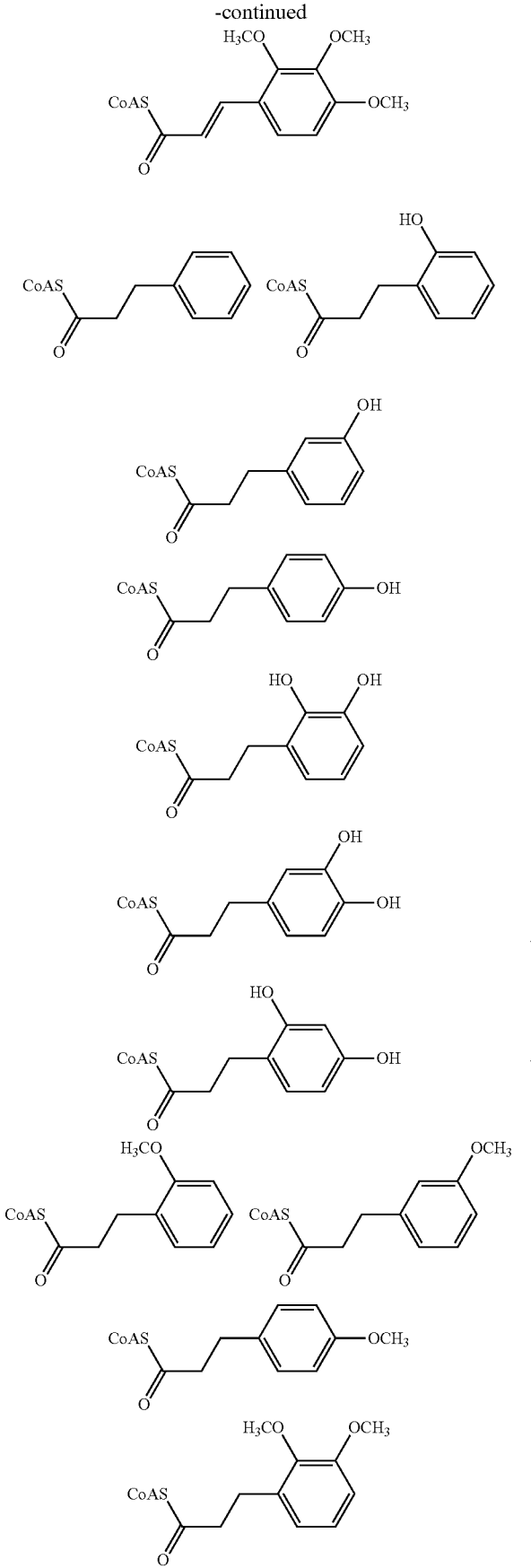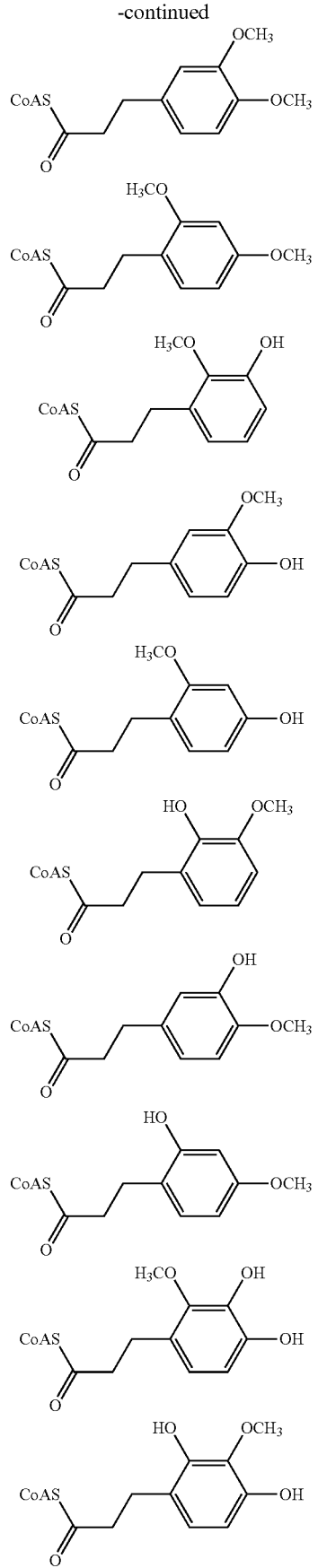

-continued

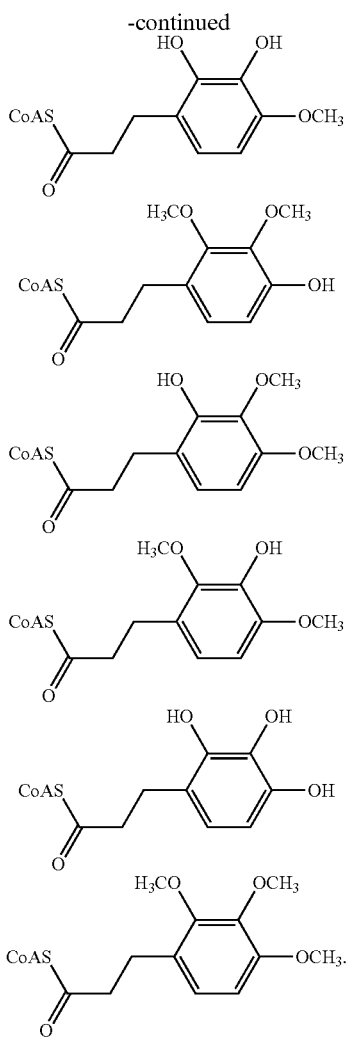

The methods to produce a compound of Formula (VII) include culturing cells engineered to express an enzyme that is at least 80% identical to PmCHS (SEQ ID NO: 4). In certain embodiments, the enzyme is at least 80%, 85%, 90%, 95%, or 100% identical to PmCHS (SEQ ID NO: 4). In certain embodiments, the enzyme is purified before reacting with a compound of Formula (II). In certain embodiments, the enzyme is partially purified before reacting with a compound of Formula (II).

In certain embodiments, the enzyme that is at least 80% identical to PmCHS (SEQ ID NO: 4) is a component in a fusion protein. A fusion protein may be created by joining two or more gene or gene segments that code for separate proteins. Translation of this fusion gene results in a single or multiple polypeptides with functional properties derived from each of the original proteins. A polyfunctional protein is a single protein that has at least two different activities, wherein that functionality is a native biological function or the result of an engineered enzyme fusion. Thus, a fusion protein may include multiple activities such as those described herein for the kavalactone or flavokavain pathway enzymes described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), meth-yltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)).

The enzyme that is at least 80% identical to PmCHS (SEQ ID NO: 4) is heterologous to the host cell. In certain embodiments, the enzyme that is at least 80% identical to PmCHS (SEQ ID NO: 4) is recombinantly produced. In certain embodiments, the enzyme that is at least 80% identical to PmCHS (SEQ ID NO: 4) is obtained from a wildtype organism. In certain embodiments, the enzyme that is at least 80% identical to PmCHS (SEQ ID NO: 4) is obtained from a mutant organism. In certain embodiments, the enzyme that is at least 80% identical to PmCHS (SEQ ID NO: 4) is obtained from a genetically-modified organism. In certain embodiments, the organism is a non-human organism. In certain embodiments, the non-human organism is selected from group consisting of bacteria, yeast, and plant. In certain embodiments, the organism is a plant. In certain embodiments, the plant is *Piper methysticum*.

A nucleic acid encoding the enzyme may be introduced into the cell in a vector (e.g., plasmids, viral vectors, cosmids, and artificial chromosomes). In certain embodiments, the nucleic acid is cDNA derived from the amino acid sequence of the enzyme that is at least 80% identical to PmCHS (SEQ ID NO: 4). In some embodiments multiple cDNAs comprising sequences complementary to different genes (e.g., 2, 3, 4, 5, or more genes) described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)), are introduced into the same cell individually, or together, or as part of a single nucleic acid.

The host cells expressing the enzyme that is at least 80% identical to PmCHS (SEQ ID NO: 4) may be prokaryotic cells, such as bacterial cells (e.g., *Escherichia coli* cells), or eukaryotic cells, such as yeast cells or plant cells. In certain embodiments, the host cell is capable of expressing two or more kavalactone or flavokavain pathway enzymes described herein. In certain embodiments, the host cell is a bacteria cell and is a wildtype, mutant, recombinant, or genetically engineered form of *Escherichia coli*. In certain embodiments, the host cell is a yeast cell and is a wildtype, mutant, recombinant, or genetically engineered form of *Saccharomyces cerevisiae*. In certain embodiments, the host cell is a plant cell and is a wildtype, mutant, recombinant, or genetically engineered form of *Nicotiana benthamiana*.

In certain embodiments, the method for producing a compound of Formula (VII) utilizes a compound of Formula (I), or a salt thereof, as the starting material and comprises the steps: condensing a compound of Formula (I), or a salt thereof, with coenzyme A (CoA) using an enzyme that is at least 80% identical to Pm4CL1 (SEQ ID NO: 1) to produce a compound of Formula (II); and reacting a compound of Formula (II), or a salt thereof, with malonyl-CoA using an enzyme that is at least 80% identical to PmCHS (SEQ ID NO: 4) to produce a compound of Formula (VII).

Production of Methylated Chalcone Compounds of Formula (VIII)

Some aspects of the present disclosure provides methods for producing a compound of Formula (VIII) from a compound of Formula (VII), or a salt thereof, and S-adenosylmethionine using an enzyme that is at least 80% identical to PmOMT4 (SEQ ID NO: 5). Some aspects of the present disclosure provides methods for producing a compound of Formula (VIII) from a compound of Formula (VII), or a salt thereof, and S-adenosylmethionine using an enzyme that is at least 80% identical to PmOMT1 (SEQ ID NO: 6). The structure of a compound of Formula (VII) and a structure of a compound of Formula (VIII) are as follows:

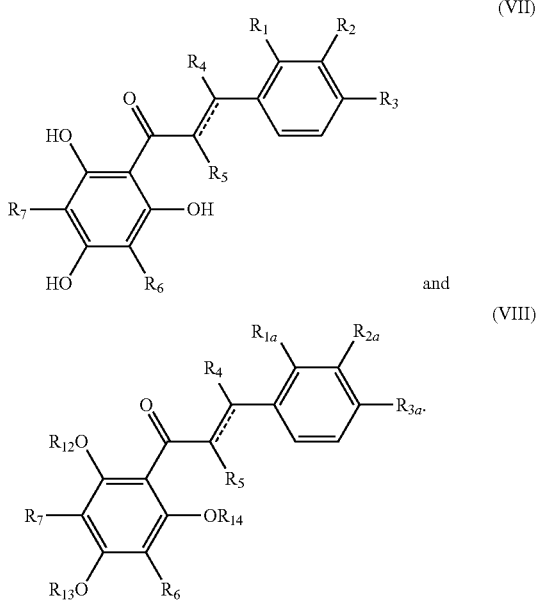

In certain embodiments, the reaction of a compound of Formula (VII) with S-adenosylmethionine to produce a compound of Formula (VIII) occurs in vitro. In certain, embodiments, the reaction of a compound of Formula (VII) with S-adenosylmethionine to produce a compound of Formula (VIII) occurs in vivo.

In certain embodiments, ⁼⁼⁼ is a single bond. In certain embodiments, ⁼⁼⁼ is a double bond.

In certain embodiments, each of $R_1$, $R_2$, $R_3$, $R_{1a}$, $R_{2a}$, $R_{3a}$, $R_6$, and $R_7$ independently is hydrogen, optionally substituted, cyclic or acyclic aliphatic, or $OR_x$, wherein $R_x$ is hydrogen or optionally substituted, cyclic or acyclic aliphatic. In certain embodiments, $R_1$ is hydrogen. In certain embodiments, $R_2$ is hydrogen. In certain embodiments, $R_3$ is hydrogen. In certain embodiments, $R_1$ is —OH. In certain embodiments, $R_2$ is OH. In certain embodiments, $R_3$ is —OH. In certain embodiments, $R_1$ is —OCH$_3$. In certain embodiments, $R_2$ is —OCH$_3$. In certain embodiments, $R_3$ is —OCH$_3$. In certain embodiments, $R_1$, $R_2$, and $R_3$ are hydrogen. In certain embodiments, $R_1$, $R_2$, and $R_3$ are —OH. In certain embodiments, $R_1$ and $R_3$ are —OH. In certain embodiments, $R_2$ and $R_3$ are —OH. In certain embodiments, $R_2$ is —OCH$_3$. In certain embodiments, $R_6$ is hydrogen. In certain embodiments, $R_7$ is hydrogen. In certain embodiments, both $R_6$ and $R_7$ are hydrogen.

In certain embodiments, each of $R_4$ and $R_5$ independently is hydrogen or optionally substituted, cyclic or acyclic aliphatic. In certain embodiments, $R_4$ and $R_5$ are hydrogen.

In certain embodiments, each of $R_{12}$ and $R_{13}$ independently is optionally substituted, cyclic or acyclic aliphatic. In certain embodiments, $R_{12}$ and $R_{13}$ are —CH$_3$. In certain embodiments, $R_{14}$ is hydrogen. In certain embodiments, $R_{14}$ and $R_{13}$ are —CH$_3$. In certain embodiments, $R_{12}$ is hydrogen. In certain embodiments, $R_{12}$ is —CH$_3$, $R_{13}$ is —CH$_3$, and $R_{14}$ is hydrogen.

In certain embodiments, $R_{1a}$, $R_{2a}$, and $R_{3a}$ are hydrogen. In certain embodiments, $R_1$, $R_2$, $R_{1a}$ and $R_{2a}$ are hydrogen and $R_3$ is —OH. In these instances, a compound of Formula (VII) can provide different compounds of Formula (VIII) depending on the choice to utilize only an enzyme that is at least 80% identical to PmOMT4 (SEQ ID NO: 5), or only an enzyme that is at least 80% identical to PmOMT1 (SEQ ID NO: 6), or both enzymes. In certain embodiments, $R_{13}$ is —CH$_3$ when a compound of Formula (VII) is reacted with an enzyme that is at least 80% identical to PmOMT4 (SEQ ID NO: 5). In certain embodiments, $R_{13}$ is hydrogen when a compound of Formula (VII) is reacted with an enzyme that is at least 80% identical to PmOMT1 (SEQ ID NO: 6). In certain embodiments, $R_{13}$ is —CH$_3$ when a compound of Formula (VII) is reacted with both an enzyme that is at least 80% identical to PmOMT4 (SEQ ID NO: 5) and an enzyme that is at least 80% identical to PmOMT1 (SEQ ID NO: 6). In certain embodiments, $R_{3a}$ is —OCH$_3$ when a compound of Formula (VII) is reacted with an enzyme that is at least 80% identical to PmOMT4 (SEQ ID NO: 5). In certain embodiments, $R_{3a}$ is —OH when a compound of Formula (VII) is reacted with an enzyme that is at least 80% identical to PmOMT1 (SEQ ID NO: 6). In certain embodiments, $R_{3a}$ is —OCH$_3$ when a compound of Formula (VII) is reacted with both an enzyme that is at least 80% identical to PmOMT4 (SEQ ID NO: 5) and an enzyme that is at least 80% identical to PmOMT1 (SEQ ID NO: 6). In certain embodiments, $R_{12}$ is —CH$_3$ and $R_{14}$ is hydrogen or $R_{12}$ is hydrogen and $R_{14}$ is —CH$_3$ when a compound of Formula (VII) is reacted with an enzyme that is at least 80% identical to PmOMT1 (SEQ ID NO: 6). In certain embodiments, $R_{12}$ and $R_{14}$ are hydrogen when a compound of Formula (VII) is reacted with an enzyme that is at least 80% identical to PmOMT4 (SEQ ID NO: 5). In certain embodiments, $R_{12}$ is —CH$_3$ and $R_{14}$ is hydrogen or $R_{12}$ is hydrogen and $R_{14}$ is —CH$_3$ when a compound of Formula (VII) is reacted with an enzyme that is at least 80% identical to PmOMT4 (SEQ ID NO: 5) and an enzyme that is at least 80% identical to PmOMT1 (SEQ ID NO: 6).

The methods to produce a compound of Formula (VIII) include reacting malonyl-CoA with a compound of Formula (VII) selected from the group consisting of:

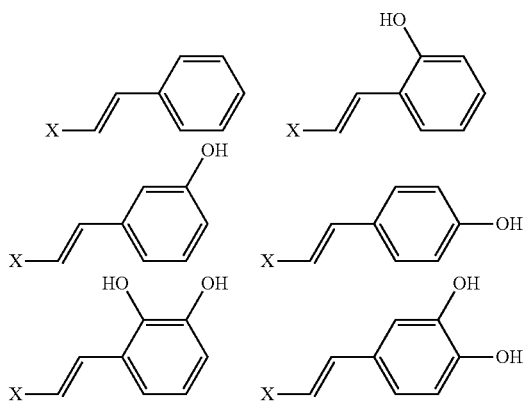

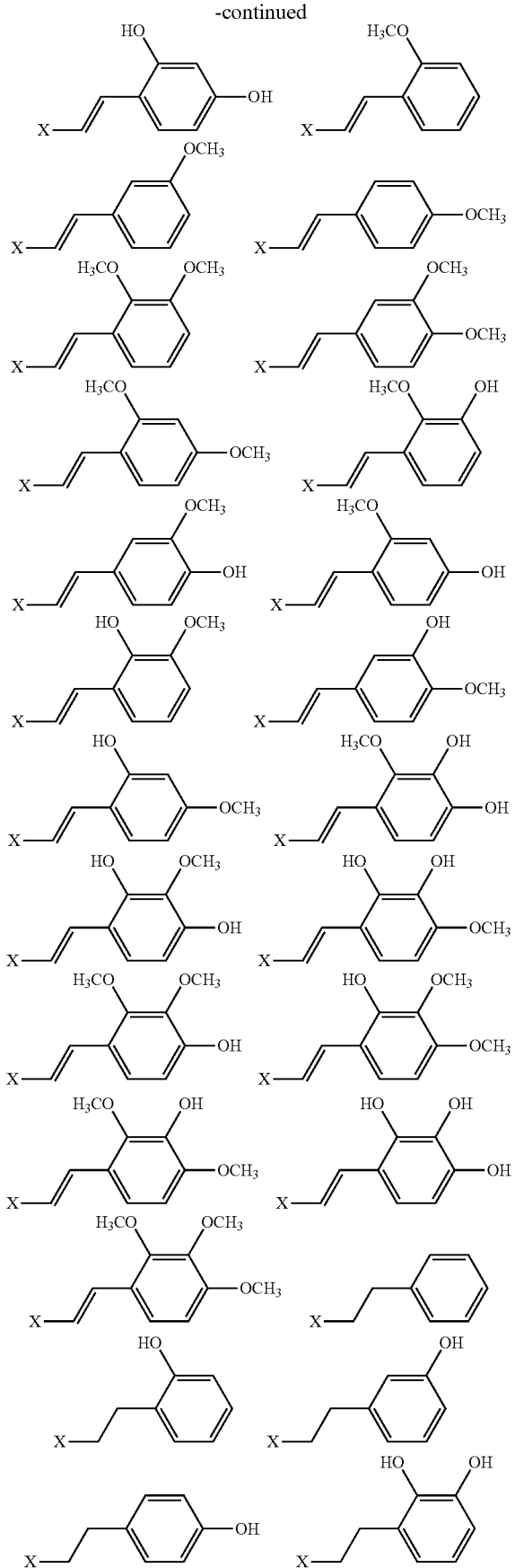
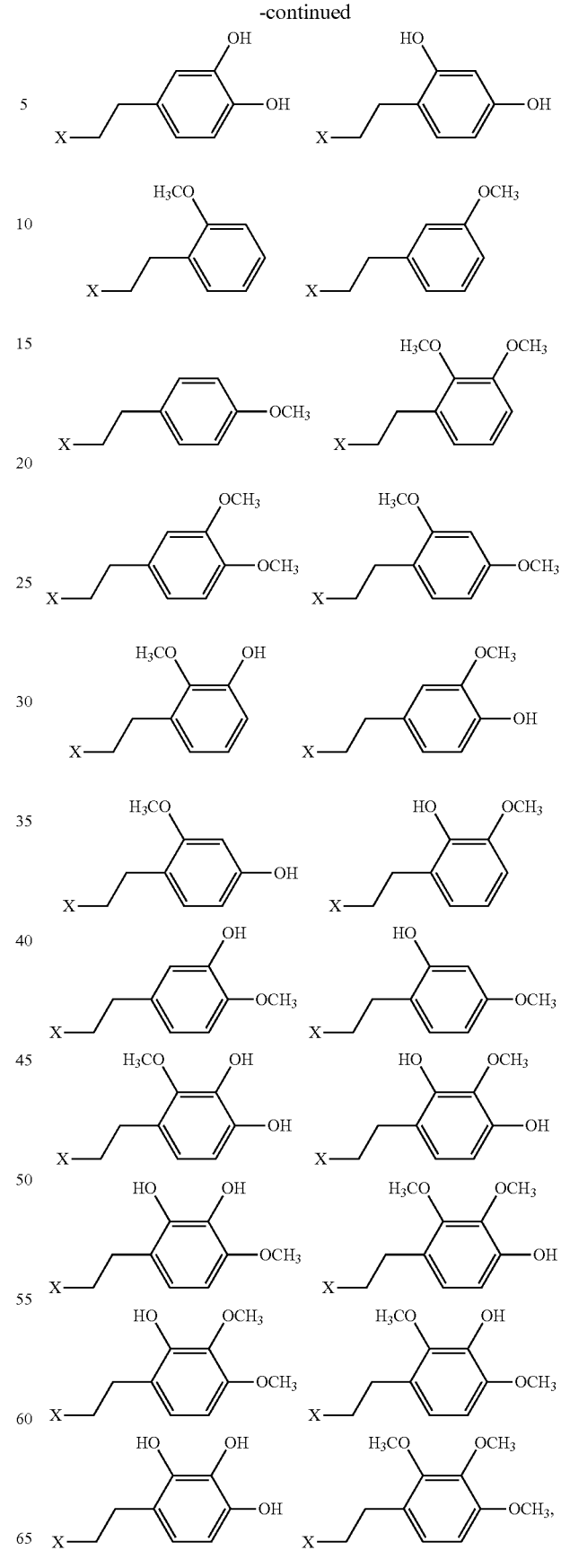

wherein X is

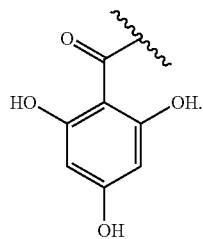 [SMILES: *C(=O)c1c(O)cc(O)cc1O]

The methods to produce a compound of Formula (VIII) include culturing cells engineered to express an enzyme that is at least 80% identical to PmOMT4 (SEQ ID NO: 5). The methods to produce a compound of Formula (VIII) include culturing cells engineered to express an enzyme that is at least 80% identical to PmOMT1 (SEQ ID NO: 6). In certain embodiments, the enzyme is at least 80%, 85%, 90%, 95%, or 100% identical to PmOMT4 (SEQ ID NO: 5). In certain embodiments, the enzyme is at least 80%, 85%, 90%, 95%, or 100% identical to PmOMT1 (SEQ ID NO: 6). In certain embodiments, the enzyme is purified before reacting with a compound of Formula (VII). In certain embodiments, the enzyme is partially purified before reacting with a compound of Formula (VII).

In certain embodiments, the enzyme that is at least 80% identical to PmOMT4 (SEQ ID NO: 5) is a component in a fusion protein. In certain embodiments, the enzyme that is at least 80% identical to PmOMT1 (SEQ ID NO: 6) is a component in a fusion protein. A fusion protein may be created by joining two or more gene or gene segments that code for separate proteins. Translation of this fusion gene results in a single or multiple polypeptides with functional properties derived from each of the original proteins. A polyfunctional protein is a single protein that has at least two different activities, wherein that functionality is a native biological function or the result of an engineered enzyme fusion. Thus, a fusion protein may include multiple activities such as those described herein for the kavalactone or flavokavain pathway enzymes described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ID NO: 6), cytochrome P450 enzyme PmMDB1 (at least 80% identical to SEQ ID NO: 7), and NADPH-dependent reductase PmRDCT10 (at least 80% identical to SEQ ID NO: 8)).

The enzyme that is at least 80% identical to PmOMT4 (SEQ ID NO: 5) is heterologous to the host cell. The enzyme that is at least 80% identical to PmOMT1 (SEQ ID NO: 6) is heterologous to the host cell. In certain embodiments, the enzyme that is at least 80% identical to PmOMT4 (SEQ ID NO: 5) is recombinantly produced. In certain embodiments, the enzyme that is at least 80% identical to PmOMT1 (SEQ ID NO: 6) is recombinantly produced. In certain embodiments, the enzyme that is at least 80% identical to PmOMT4 (SEQ ID NO: 5) is obtained from a wildtype organism. In certain embodiments, the enzyme that is at least 80% identical to PmOMT4 (SEQ ID NO: 5) is obtained from a mutant organism. In certain embodiments, the enzyme that is at least 80% identical to PmOMT4 (SEQ ID NO: 5) is obtained from a genetically-modified organism. In certain embodiments, the enzyme that is at least 80% identical to PmOMT1 (SEQ ID NO: 6) is obtained from a wildtype organism. In certain embodiments, the enzyme that is at least 80% identical to PmOMT1 (SEQ ID NO: 6) is obtained from a mutant organism. In certain embodiments, the enzyme that is at least 80% identical to PmOMT1 (SEQ ED NO: 6) is obtained from a genetically-modified organism. In certain embodiments, the organism is a non-human organism. In certain embodiments, the non-human organism is selected from group consisting of bacteria, yeast, and plant. In certain embodiments, the organism is a plant. In certain embodiments, the plant is *Piper methysticum*.

A nucleic acid encoding the enzyme may be introduced into the cell in a vector (e.g., plasmids, viral vectors, cosmids, and artificial chromosomes). In certain embodiments, the nucleic acid is cDNA derived from the amino acid sequence of the enzyme that is at least 80% identical to PmOMT4 (SEQ ID NO: 5). In certain embodiments, the nucleic acid is cDNA derived from the amino acid sequence of the enzyme that is at least 80% identical to PmOMT1 (SEQ ID NO: 6). In some embodiments multiple cDNAs comprising sequences complementary to different genes (e.g., 2, 3, 4, 5, or more genes) described herein (i.e., 4-coumarate-CoA ligase Pm4CL1 (at least 80% identical to SEQ ID NO: 1), styrylpyrone synthase PmSPS1 (at least 80% identical to SEQ ID NO: 2), PmSPS2 (at least 80% identical to SEQ ID NO: 3), PmCHS (at least 80% identical to SEQ ID NO: 4), methyltransferase PmOMT4 (at least 80% identical to SEQ ID NO: 5), methyltransferase PmOMT1 (at least 80% identical to SEQ ED NO: 6), cytochrome P450 enzyme PmMDB1 (at least 80% identical to SEQ ID NO: 7), and NADPH-dependent reductase PmRDCT10 (at least 80% identical to SEQ ID NO: 8)), are introduced into the same cell individually, or together, or as part of a single nucleic acid.

The host cells expressing the enzyme that is at least 80% identical to PmOMT4 (SEQ ID NO: 5) may be prokaryotic cells, such as bacterial cells (e.g., *Escherichia coli* cells), or eukaryotic cells, such as yeast cells or plant cells. The host cells expressing the enzyme that is at least 80% identical to PmOMT1 (SEQ ID NO: 6) may be prokaryotic cells, such as bacterial cells (e.g., *Escherichia coli* cells), or eukaryotic cells, such as yeast cells or plant cells. In certain embodiments, the host cell is capable of expressing two or more kavalactone or flavokavain pathway enzymes described herein. In certain embodiments, the host cell is a bacteria cell and is a wildtype, mutant, recombinant, or genetically engineered form of *Escherichia coli*. In certain embodiments, the host cell is a yeast cell and is a wildtype, mutant, recombinant, or genetically engineered form of *Saccharomyces cerevisiae*. In certain embodiments, the host cell is a plant cell and is a wildtype, mutant, recombinant, or genetically engineered form of *Nicotiana benthamiana*.

In certain embodiments, the method for producing a compound of Formula (VIII) utilizes a compound of Formula (I), or a salt thereof, as the starting material and comprises the steps: condensing a compound of Formula (I), or a salt thereof, with coenzyme A (CoA) using an enzyme that is at least 80% identical to Pm4CL1 (SEQ ID NO: 1) to produce a compound of Formula (II); reacting a compound of Formula (II), or a salt thereof, with malonyl-CoA using an enzyme that is at least 80% identical to PmCHS (SEQ ID NO: 4) to produce a compound of Formula (VII); and methylating a compound of Formula (VII), or a salt thereof, with S-adenosylmethionine using an enzyme that at least 80% identical to PmOMT4 (SEQ ID NO: 5).

In certain embodiments, the method for producing a compound of Formula (VIII) utilizes a compound of Formula (I), or a salt thereof, as the starting material and comprises the steps: condensing a compound of Formula (I), or a salt thereof, with coenzyme A (CoA) using an enzyme that is at least 80% identical to Pm4CL1 (SEQ ID NO: 1) to produce a compound of Formula (II); reacting a compound of Formula (II), or a salt thereof, with malonyl-CoA using an enzyme that is at least 80% identical to PmCHS (SEQ ID NO: 4) to produce a compound of Formula (VII); and methylating a compound of Formula (VII), or a salt thereof, with S-adenosylmethionine using an enzyme that at least 80% identical to PmOMT1 (SEQ ID NO: 6).

In Vitro Reactions

In vitro reactions are utilized in the present disclosure. In certain embodiments, the reactions use water as a solvent. In certain embodiments, the reaction is performed at room temperature. In certain embodiments, the reaction is performed for 10 minutes to 24 hours. In certain embodiments, the reaction is performed for 2 hours.

The components of the reactions may include one of more of the following: buffer; $MgCl_2$; ATP; CoA; malonyl-CoA; a compound of Formula (I), Formula (II), Formula (III), Formula (IV), or Formula (VII); S-adenosylmethionine; NADPH; and an enzyme described herein. In certain embodiments, the buffer is potassium phosphate of pH=7.6. In certain embodiments, the concentration of the buffer is 50 mM. In certain embodiments, the concentration of the $MgCl_2$ is 2.5 mM. In certain embodiments, the concentration of the ATP is 3 mM. In certain embodiments, the concentration of CoA is 2 mM. In certain embodiments, the concentration of malonyl CoA is 3 mM. In certain embodiments the concentration of the compound described herein is 0.5 mM. In certain embodiments, the concentration of S-adenosylmethionine is 2 mM. In certain embodiments, the concentration of NADPH is 6 mM. In certain embodiments, the concentration of an enzyme described herein is 10 μg/ml final concentration of each enzyme used in the reaction.

EXAMPLES

In order that the invention described herein may be more fully understood, the following examples are set forth. The examples described in this application are offered to illustrate the methods, compositions, and systems provided herein and are not to be construed in any way as limiting their scope.

Example 1. Activity of Pm4CL1, PmSPS1, PmSPS2, and PmCHS

Figure 4:
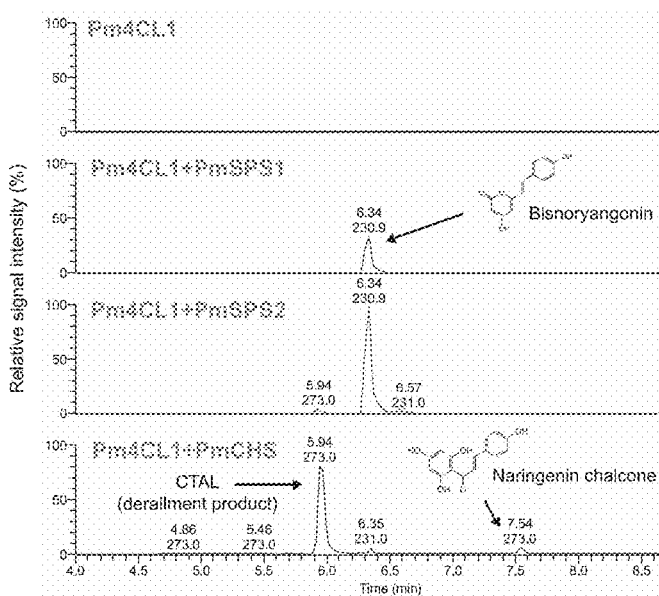
FIG. 4 shows the in vitro enzymatic production of bisnoryangonin (kavalactone intermediate with 6-styryl-4-hydroxy-2-pyrone backbone) and naringenin chalcone (flavokavain intermediate with chalcone backbone) using purified recombinant PmSPS1, PmSPS2, and PmCHS enzymes from p-coumaric acid. CTAL (p-coumaroyltriacetic acid lactone is a known in vitro derailment byproduct of chalcone synthase (CHS), which is not produced in vivo.

Using purified recombinant enzymes expressed in *Escherichia coli*, we have shown the activity of PmSPS1, PmSPS2, and PmCHS in vitro (FIG. 4). This assay used p-coumaric acid as a substrate and utilized the purified 4-coumarate-CoA ligase Pm4CL1 to produce p-coumaroyl-CoA.

Figure 5:
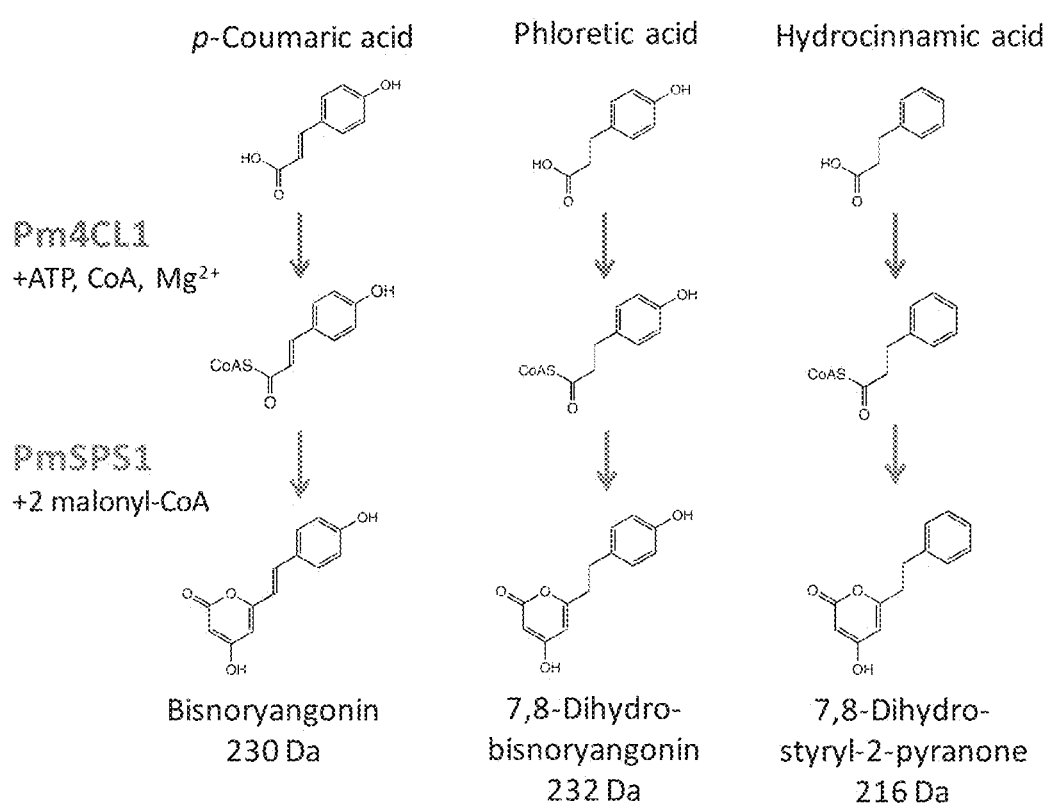
FIG. 5 shows the enzymatic production of compounds with a 6-styryl-4-hydroxy-2-pyrone backbone from carboxylic acid compounds with single bond or double bond at the 7,8-position: p-coumaric acid, phloretic acid, and hydrocinnamic acid.
Figure 6:
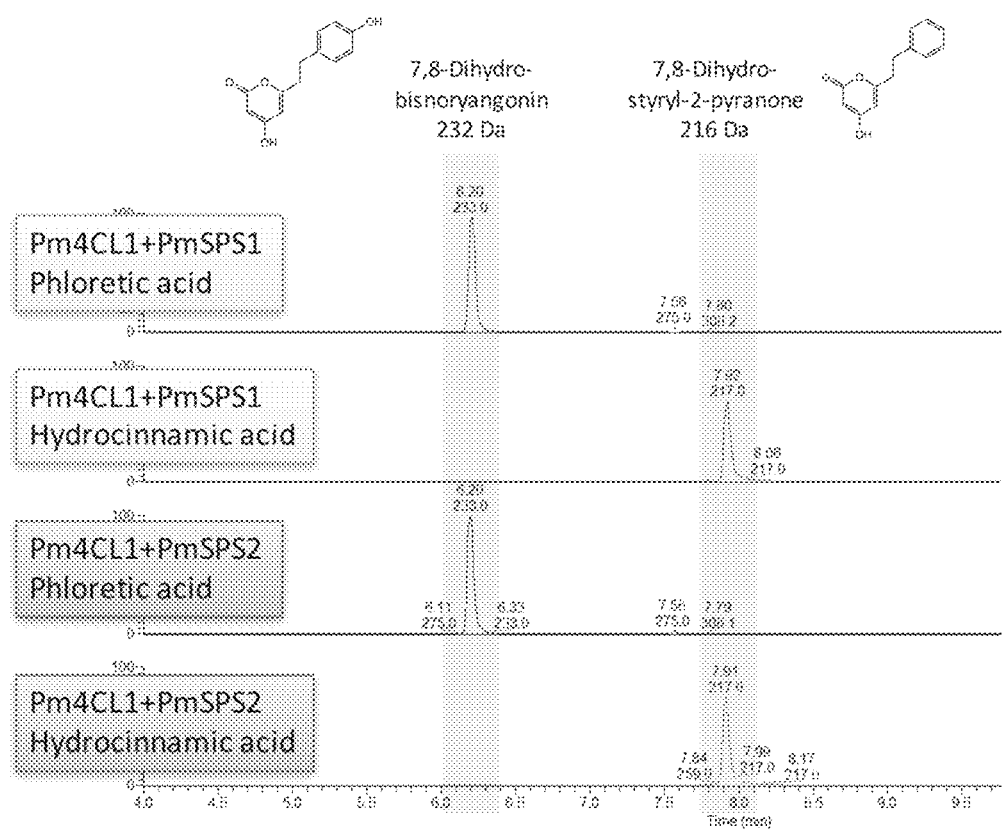
FIG. 6 shows the in vitro enzymatic production starting from phloretic acid and hydrocinnamic acid of compounds with a 6-styryl-4-hydroxy-2-pyrone backbone and single bond at the 7,8-position.

The PmSPS1 and PmSPS2 enzymes can also utilize substrates derived from cinnamic acid variants phloretic acid and hydrocinnamic (phenylpropanoic) acid, which include a single bond instead of the double bond present in cinnamic acid (FIG. 5). This results in a 6-styryl-4-hydroxy-2-pyrone backbone with a single bond at $C_7$-$C_8$ position, which can be used to produce reduced kavalactones, such as 7,8-dihydrokavain or 7,8-dihydroyangonin. This activity was verified using in-vitro enzyme assays monitored by LC-MS (FIG. 6).

Example 2. Activity of PmOMT4 and PmOMT1

Two methyltransferases, PmOMT4 and PmOMT1, add methyl groups to hydroxyl groups at various positions of the 6-styryl-4-hydroxy-2-pyrone backbone. PmOMT4 is the key methyltransferase that adds a methyl group to the 4-position, as seen in all kavalactones. In addition, PmOMT4 can methylate the $C_{11}$ and $C_{12}$ positions (if hydroxyl groups are present there), as found, for example, in 11-methoxyyangonin (FIG. 7). On the other hand, PmOMT1 adds a methyl group to the $C_{10}$ position, as found, for example, in 10-methoxyyangonin (FIG. 7).

Figure 8:
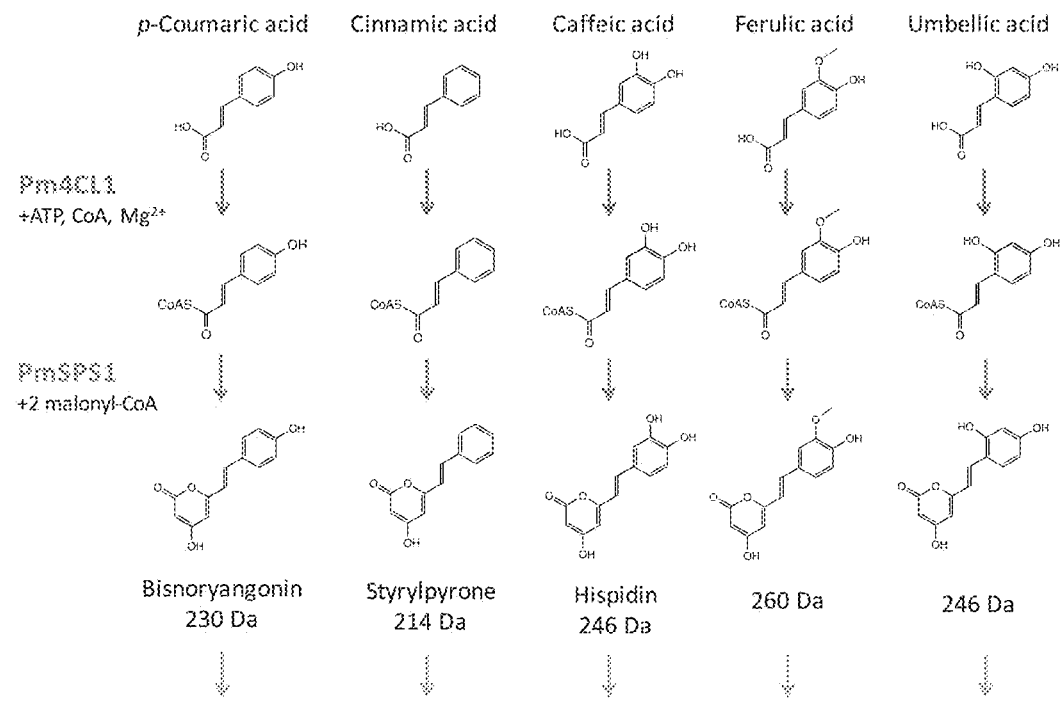
FIG. 8 shows liquid chromatography-mass spectrometry (LC-MS) results (m/z at retention time) of final products of enzymatic processes using different substrates and a combination of PmCL1, PmSPS1, and two methyltransferases PmOMT4 and PmOMT1.

The target hydroxyl sites of PmOMT1 and PmOMT4 were determined by coupled enzyme assays using different starting substrates (variants of cinnamic acid with different hydroxy modifications on the aromatic ring). The enzyme assay utilized Pm4CL1 and PmSPS1 to produce the 6-styryl-4-hydroxy-2-pyrone backbone, and increase in mass after adding the methyltransferases was monitored by LC-MS (FIG. 8).

Example 3. Activity of PmRDCT10

Figure 9:
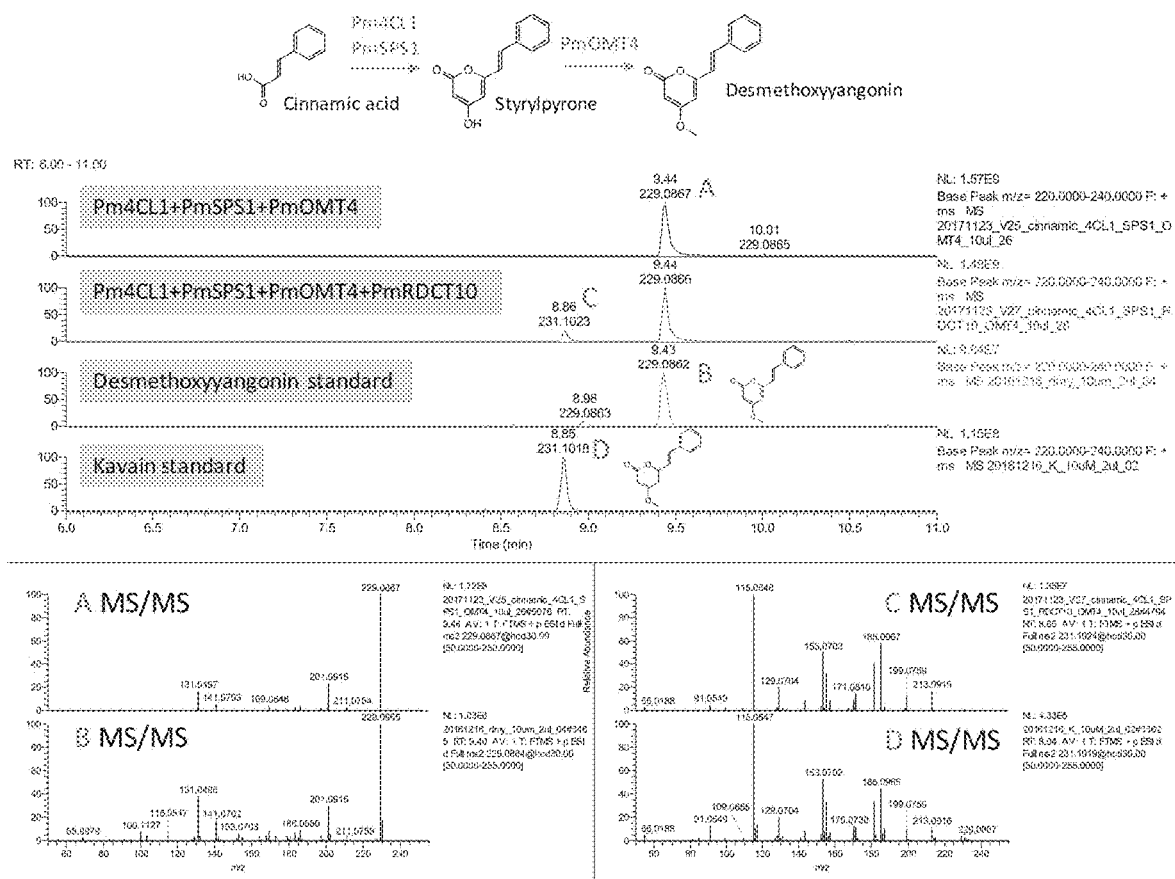
FIG. 9 shows the results of an in vitro enzyme assay demonstrating the activity of PmRDCT10 to reduce the $C_5$-$C_6$ double bond in kavalactones. While the combination of Pm4CL1, PmSPS1, and PmOMT4 is sufficient to produce the kavalactone desmethoxyyangonin from cinnamic acid, PmRDCT10 is required to produce kavain, which carries a single bond at the $C_5$-$C_6$ position. The identity of desmethoxyyangonin and kavain was confirmed with pure standards, including their retention times and utilizing tandem mass spectrometry (MS/MS) as shown in the bottom panel.

The $C_5$-$C_6$ double bond in kavalactones can be reduced into a single bond by an NADPH-dependent reductase PmRDCT10, as demonstrated by another in vitro enzyme assay (FIG. 9). This reaction is essential to produce reduced kavalactones such as kavain or methysticin.

Example 4. Activity of PmMDB1

Figure 10:
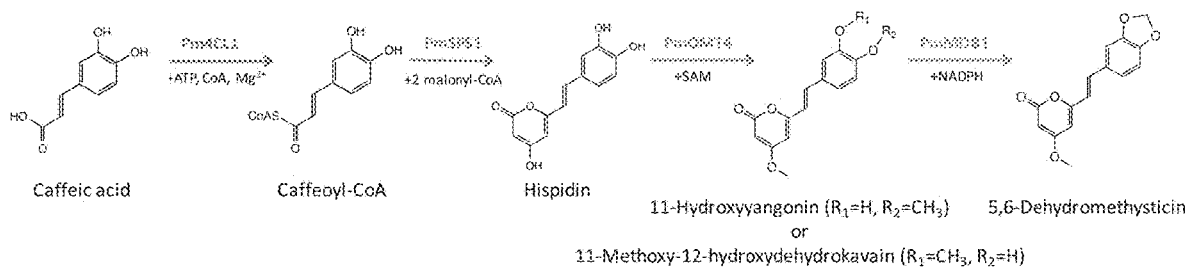
FIG. 10 shows the pathway to produce methylenedioxy bridge-containing kavalactones such as 5,6-dehydromethysticin starting from caffeic acid.

The methylenedioxybridge bridge found at the $C_{11}$-$C_{12}$ position in several kavalactones (methysticin, dihydromethysticin, or dehydromethysticin) is formed by a cytochrome P450 enzyme PmMDB1, which belongs to the CYP719 family (FIG. 10).

Figure 11:
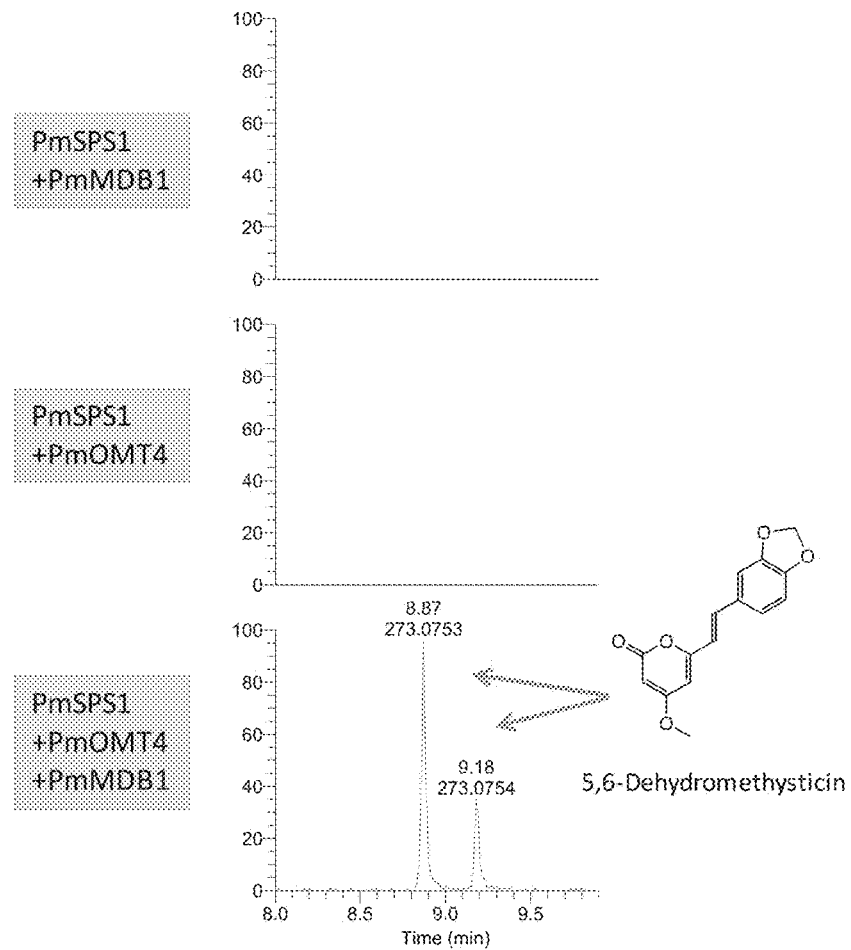
FIG. 11 shows the LC-MS traces of mass 273.075 m/z corresponding to $[C_{15}H_{12}C_5+H]^+$ ion of 5,6-dehydromethysticin in *Agrobacterium*-infiltrated *N. benthamiana* leaves. Each leaf was infiltrated with a mixture of agrobacterial strains carrying plasmids with the indicated enzymes.
Figure 12:
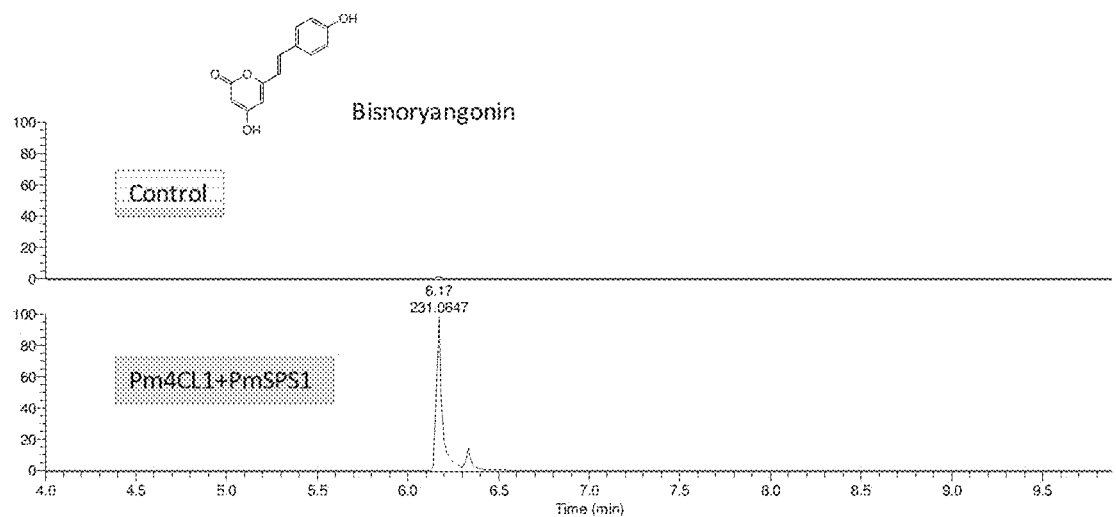
FIG. 12 shows the production of bisnoryangonin in vivo in *E. coli*. The *E. coli* BW27784 strain carrying expression plasmids with the indicated enzymes was incubated for 24 hours in the presence of 1 mM p-coumaric acid.
Figure 13:
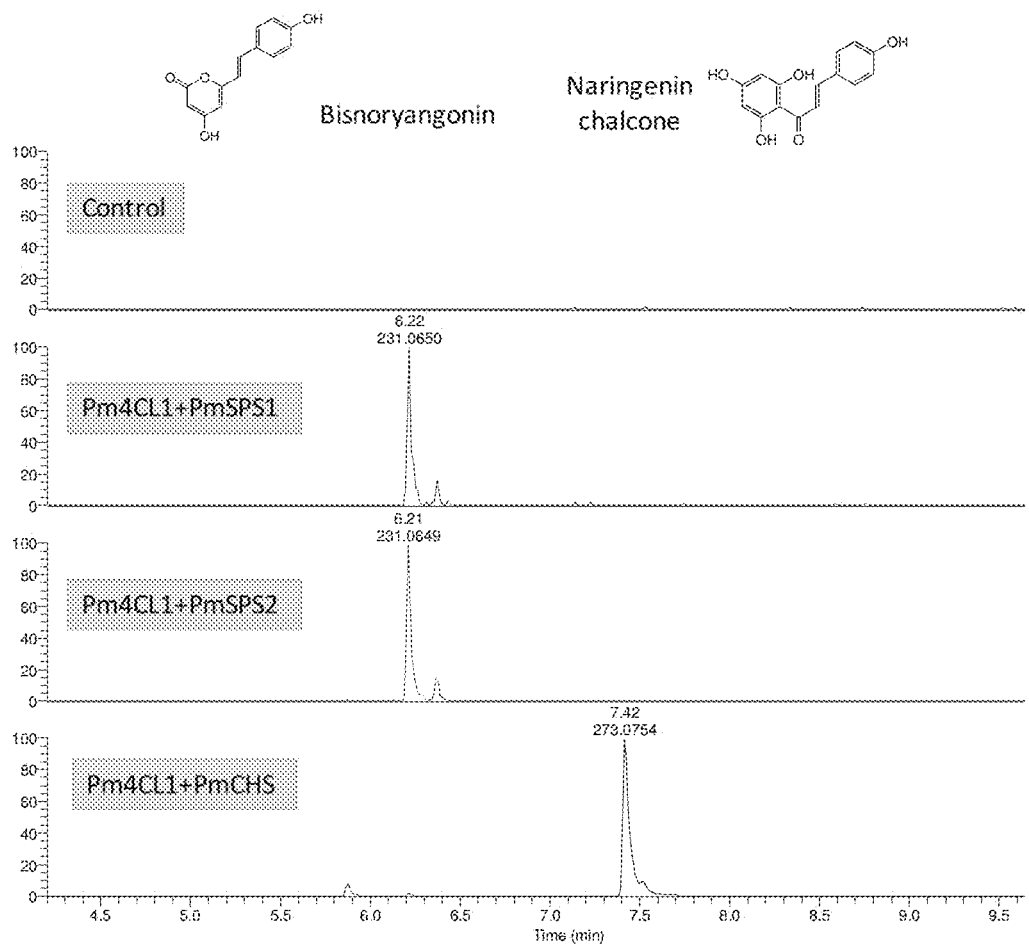
FIG. 13 shows the production of bisnoryangonin and naringenin chalcone in vivo in the baker's yeast *S. cerevisiae*. The yeast strain BY4743 carrying expression plasmids with the indicated enzymes was incubated for 2 days in the presence of 2 mM p-coumaric acid.
Figure 14:
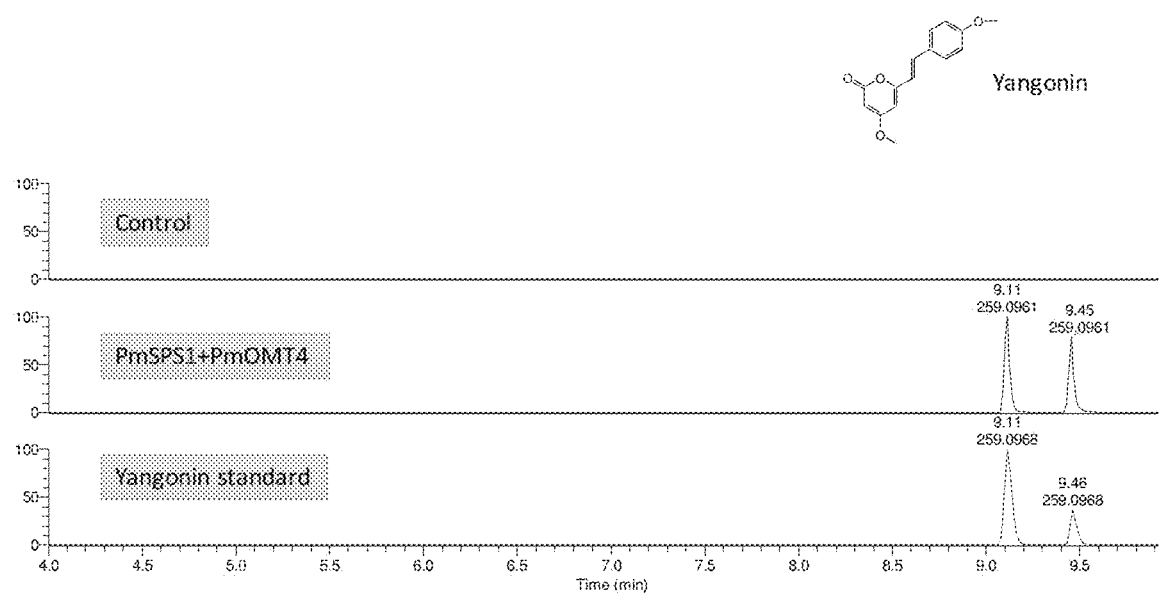
FIG. 14 shows the production of the kavalactone yangonin in vivo in the plant *Nicotiana benthamiana* through *Agrobacterium*-mediated infiltration. This assay utilized the native *Nicotiana* 4CL enzyme.

The activity of PmMDB1 was confirmed by *Agrobacterium*-mediated heterologous expression in *Nicotiana benthamiana* (FIG. 11). This assay utilized the native *Nicotiana* 4CL.

Example 5. Enzyme Amino Acid Sequences

Pm4CL1 (SEQ ID NO: 1):
MKMVVDTIATDRCVYRSKLPDIEIKNDMSLHNYCFQNIGAYRDNPCLING

STGEVYTYGEVETTARRVAAGLHRMGVQQREVIMILLPNSPEFVFAFLGA

SFRGAMSTTANPFYTPQEIAKQVKASGAKLIVTMSAYVDKVRDLAEERGV

KVVCVDAPPPGCSHFSELSGADESELPEVDIDPDDVVALPYSSGTTGLPK

GVMLTHRSQVTSVAQQVDGENPNLYFRPDDVLLCVLPLFHIYSLNSVLFC

GLRVGAAILIMQKFEITALMELVQKYKVTIAPIVPPIVLAIAKSPLVDKY

DLSSIRTVMSGAAPMGKELEDAVRAKLPNAKLGQGYGMTEAGPVLSMCLA

FAKEPFEIKSGSCGTVVRNAQLKIVDPETGAYLPRNQPGEICIRGSQIMK

GYLNDAAATQRTIDKEGWLHTGDIGYVDDDEELFIVDRLKEIIKYKGFQV

APAELEAILITHPNIADAAVVPMKDEAAGEVPVAFVVTSNGSVISEDEIK

QFISKQVVFYKRINRVFFVDSIPKAPSGKILRKDLRGRLAAGIPK

PmSPS1 (SEQ ID NO: 2):
MSKTVEDRAAQRAKGPATVLAIGTATPANVVYQTDYPDYYFRVTKSEHMT

KLKNKFQRMCDRSTIKKRYMVLTEELLEKNLSLCTYMEPSLDARQDILVP

EVPKLGKEAADEAIAEWGRPKSEITHLIFCTTCGVDMPGADYQLTKLLGL

RSSVRRTMLYQQGCFGGGTVLRLAKDLAENNAGARVLVVCSEITTAVNFR

```
GPSDTHLDLLVGLALFGDGAAAVIVGADPDPTLERPLFQIVSGAQTILPD

SEGAINGHLREVGLTIRLLKDVPGLVSMNIEKCLMEAFAPMGIHDWNSIF

WIAHPGGPTILDQVEAKLGLKEEKLKSTRAVLREYGNMSSACVLFILDEV

RKRSMEEGKTTTGEGFDWGVLFGFGPGFTVETVVLHSMPIPKADEGR

PmSPS2 (SEQ ID NO: 3):
MSKMVEEHWAAQRARGPATVLAIGTANPPNVLYQADYPDFYFRVTKSEHM

TQLKEKYKRICDKSAIRKRHLHLTEELLEKNPNICAHMAPSLDARQDIAV

VEVPKLAKEAATKAIKEWGRPKSDITHLIFCTTCGVDMPGADYQLTTLLG

LRPTVRRTMLYQQGCFAGGTVLRHAKDFAENNRGARVLAVCSEFTVMNFS

GPSEAHLDSMVGMALFGDGASAVIVGADPDFAIERPLFQLVSTTQTIVPD

SDGAIKCHLKEVGLTLHLVICNVPDLISNNMDKILEEAFAPLGIRDWNSI

FWTAHPGGAAILDQLEAKLGLNKEKLKTTRTVLREYGNMSSACVCFVLDE

MRRSSLEEGKTTSGEGLEWGILLGFGPGLTVETVVLRSVPISTAN

PmCHS (SEQ ID NO: 4):
MSKTVEEIWAAQRARGPATVLAIGTAAPANVVYQADYPDYYFRITKSEHM

TELKEKFRRMCDKSMITKRHMHLSEELLKNNPDICAYMAPSLDARQDMVV

VEVPKLGKEAAAKAIKEWGRPKSAITHLIFCTTSGVDMPGADFQLTKLLG

LCPSVRRTMLYQQGCFAGGTVLRLAKDLAENNAGARVLVVCSETTAVTFR

GPSETHLDSMVGQALFGDGASAIIVGADPDPVIERPLFQIVSAAQTILPD

SDGAIDGHLREVGLTFHLLKDVPGLISKNIEKSLKEAFAPLGIDDWNSIF

WIVHPGGPAILDQVEAKLRLKVEKLKTTRTVLSEYGNMSSACVLFILDEM

RRNSMEEGKATTGEGLHWGVLFGFGPGLTVETVVLHSLPIAEAN

PmOMT4 (SEQ ID NO: 5):
MEQAVFKDQSPSRDDIDEELFQSALYLSTAVVTVPAAIMAANDLDVLQII

AKAGPGAHLSPTEIVSHLPTRNPNAAAALHRILRVLASHSILECSSRCEG

EAKYGLRPVCKFFLNDKDGVSLNAMPSFVQSRVFIDSWQYMKDAVLEGVV

PFEKAYGMPFYQFQAVNTKFKETFAKAMAAHSTLVVKICMLDTYNGFEGL

TELMDVAGGTGSTLNLIVSKYPQIKGTNFDLICHVIEAAPNYPGVKHLSG

DMFDSIPSAKNIIMKWILHNWSDEHCVKLLKNCYTSLPEFGKLIVVDSIV

GEDVDAGUTTTNVFGCDFTMLTFFPNAKERTREEFQDLAKASGFSTFKPI

CCAYGVWVMEFHK

PmOMT1 (SEQ ID NO: 6):
MNDQELHGYSQNAQPQLWNLLLSFINSMSLKCAVELGIPDIIHSHAQTPI

NITDLAASIPIPPNKTSQFRRLMRLLVHSNVFSVHKREDGDEGFLLTPMS

RILVTSNDNNGGNLSPFVSMMVDPSLVSPWHFLGQWLKGNDTQGTPFRMC

HGEEMWDWANKYPDFNKICFNMAMVCDSQYLMKIIVKKCATAFEGKRSLI

DVGGGTGGAARSIAEAFPDIQEVSVLDLPHVVAGLPNDSRVICFVGGDMF

HTIPPADVVLLKAIFHGWNDEECIKILKNCKICAIPSKEEGGKVMILDMV

VNSAPGDHMITEDQYFMDLMMITYARGLERDENEWKKLFKDAGFTSYKIT

HGLGTSSLIELYP

PmMDB1 (SEQ ID NO: 7):
MEQAQWVDPTLLPAFVGIIFFFLGMFFGRSSLGAGKGAAPRSTSSTEWPD

GPPKLPIIGNLHQLNKGGELVHHNLAKLAQSYDRAMTIWVGSWGPMIVVS

DADLAWEVLVTKSPDFAGRVLSKLSHLFNANYNTVVAYDAGPQWQSLRRG

LQHGPLGPAHVSAQARFHEEDMICLLVSDMMRAAQKGGSNGVVEPLAYVR

RATIRFLSRLCFGEAFNDEAFVEGMDEAVEETIGATGHARILDAFYFTRH

LPIIRRSFIDTVNAKKKIESLVRPLLSRPAPPGSYLHFLLSTDAPENMII

FRIFEVYLLGVDSTASTTTWALAFLVSNQQAQEKLHNELAQYCASQNNQI

IKADDVGKLSYLLGVVKETMRMKPIAPLAVPHKTLICETMLDGKRVAAGT

TVVVNLYAVHYNPKLWPEPEQFRPERFVVGASGGNGGGSSEYMLQSYLPF

GGGMRSCAGMEVGKLQVAMVVANLVMAFKWLPEEEGKMPDLAEDMTFVLM

MKKPLAAKIVPRA

PmRDCT10 (SEQ ID NO: 8):
METERKSRICVTGAGGFVASWVVKLFLSKGYLVHGTVRDLGEEKTAHLRK

LEGAYHNLQLFKADLLDYESLLGAITGCDGVLHVATPVPSSKTAYSGTEL

VKTAVNGTLNVLRACTEAKVKKVIYVSSTAAVLVNPNLPKDKIPDEDCWT

DEEYCRTTPFFLNWYCIAKTAAEKNALEYGDKEGINVISICPSYIFGPML

QPTINSSNLELLRLMKGDDESIENKFLLMVDVRDVAEAILLLYEKQETSG

RYISSPHGMRQSNLVEKLESLQPGYNYHICNFVDIKPSWTMISSEKLKKL

GWKPRPLEDTISETVLCFEEHGLLENE
```

Example 6. cDNA Sequences cDNA Sequence Encoding for Pm4CL1 (SEQ ID NO: 9)

```
cDNA Sequence Encoding for Pm4CL1
                                                    (SEQ ID NO: 9)
ATGAAGATGGTAGTAGACACTATTGCTACTGATCGATGTATACCGGTCTAAGCTGCCGGACATTGAGATCAAGAACGACAT GTCGTTGCACAATTATTGTTTCCAGAACATTGGTGCTTACCGGGACAATCCTTGTCTCATCAATGGCAGCACCGGCGAGGTGT ACACGTACGGCGAGGTGGAGACGACGGCGAGGAGGGTGGCCGCCGGCTGCACCGGATGGGGGTGCAGCAGCGGGAGGTGATC ATGATCCTCCTCCCCAACTCGCCGGAGTTCGTCTTCGCCTTTCCTCGGCGCCTCCTTCCGCGGGGCCATGTCCACCACCGCCA ACCCCTTCTACACGCCGCAGGAGATCGCCAAGCAGGTCAAGGCCTCCGGCGCGAAGCTCATCGTCACCATGTCCGCCTACGTC GACAAGGTCAGGGACCTGGCCGAGGAGCGCGGCGTCAAAGTGGTGTGCGTCGACGCGCCGCCCCCGGGTGCTCCCACTTCTC CGAGCTGTCCGGCGCCGACGAGTCGGAGCTGCCCGAGGTGGATATTGACCCCGACGACGTGGTGGCGCTGCCATACTCCTCCG GCACCACCGGCCTCCCTAAAGGAGTGATGCTCACACACCGCAGCCAGGTGACGAGCGTTGCCCAGCAAGTCGACGGCGAGAAC
```

-continued

CCGAATCTATACTTCCGGCCAGACGACGTCCTGCTCTGCGTTCTTCCCCTCTTCCACATCTACTCCCTCAACTCGGTGCTCTT

CTGCGGCCTGCGCGTCGGGGCGGCGATCCTCATCATGCAGAAGTTCGAGATCACGGCGCTGATGGAGCTGGTGCAGAAGTACA

AGGTGACCATTGCGCCCATCGTTCCGCCCATCGTTCTTGCCATCGCCAAGAGCCCGCTCGTCGACAAGTACGACTTGTCGTCC

ATTCGGACGGTGATGTCCGGCGCCGCCCCGATGGGGAAGGAGCTCGAAGACGCCGTCCGGGCCAAGCTTCCCAACGCCAAGCT

CGGCCAGGGCTATGGGATGACGGAGGCAGGGCCAGTGCTGTCCATGTGrnGGCCTTCGCCAAGGAGCCCTTCGAGATCAAGTC

TGGTTCTTGCGGCACCGTGGTCAGGAACGCCCAGCTCAAGATCGTCGACCCAGAAACCGGTGCCTACCTGCCCAGAAACCAAC

CCGGCGAAATTTGCATCCGAGGCTCCCAAATCATGAAAGGGTATCTTAATGACGCGGCGGCTACGCAGAGGACGATCGACAAG

GAAGGGTGGCTGCACACCGGCGACATTGGCTATGTCGACGACGACGAGGAGCTCTTCATTGTCGATAGGTTGAAGGAGATCAT

TAAGTACAAGGGCTTCCAAGTCGCCCCTGCCGAGCTCGAAGCCATTCTCATTACTCACCCTAACATTGCTGATGCCGCTGTTG

TCCCGATGAAAGATGAGGCAGCAGGGGAAGTGCCAGTGGCATTTGTGGTGACCTCCAATGGATCAGTCATCAGTGAGGATGAG

ATCAAGCAGTTCATTAGCAAGCAGGTGGTGTTCTACAAGCGAATCAATCGAGTCTTTTTCGTTGATTCAATTCCTAAAGCACC

CTCTGGGAAGATTTTGAGGAAGGATTTGAGGGGAAGATTGGCAGCTGGTATACCCAAGTAG cDNA Sequence Encoding for PmSPS1

(SEQ ID NO: 10)

ATGTCGAAGACGGTGGAGGATCGGGCAGCGCAGCGGGCAAAGGGGCCGGCAACAGTGCTGGCCATCGGCACGGCTACGCCGGC

CAATGTGGTGTACCAGACCGATTTATCCGGACTACTACTTCAGGGTCACCAAGAGCGAGCATATGACCAAACTCAAGAACAAG

TTTCAACGCATGTGCGACAGGTCGACGATAAAGAAGAGGTACATGGTTTTGACAGAGGAGCTGCTAGAGAAGAATCTGAGTTT

GTGCACCTACATGGAACCCTCCCTCGACGCCCGCCAAGACATTCTCGTGCCGGAGGTCCCCAAGCTCGGCAAGGAGGCCGCCG

ACGAGGCCATCGCCGAATGGGACGCCCCAAGTCGGAAATCACCCACCTCATCTTTTGCACTACCTGCGGCGTCGACATGCCC

GGCGCCGACTACCAGCTCACCAAGCTCCTCGGTCTCCGCTCCTCCGTCCGTCGCACCATGCTCTATCAGCAGGGATGCTTTGG

CGGAGGCACCGTTCTCCGCCTCGCCAAGGACCTCGCCGAGAACAACGCTGGTGCCCGCGTCCTCGTCGTCTGCTCCGAGATCA

CCACTGCCGTCAACTTCCGAGGGCCTTCCGACACCCACCTCGACTTATTGGTCGGCTTAGCCCTGTTCGGCGACGGTGCGGCC

GCGGTCATAGTCGGTGCGGATCCAGATCCTACCCTCGAGCGGCCGCTCTTTCAAATCGTATCTGGAGCACAGACGATTTCTAC

CGGACTCGGAGGGGCCATCAACGGCCATCTCCGGGAGGTGGGGCTAACCATCCGCCTACTCAAGGACGTACCTGGGCTTGTG

TCGATGAACATTGAGAAGTGCCTCATGGAGGCGTTTGCACCGATGGGCATCCACGACTGGAACTCCATCTTTTGGATAGCCCA

TCCCGGGGGGCCCACCATACTAGACCAAGTGGAGGCCAAGCTGGGTCTAAAGGAGGAGAAGCTCAAGTCGACGAGGGCTGTTC

TGAGGGAGTATGGCAACATGTCTAGCGCCTGTGTCTTGTTCATACTGGACGAGGTAAGGAAGAGGAGCATGGAGGAGGGGAAG

ACGACAACCGGTGAGGGGTTCGATTGGGGAGTTCTATTCGGCTTTGGGCCTGGCTTCACAGTGGAGACCGTCGTCTTGCACAG

CATGCCCATCCCCAAAGCCGATGAAGGCAGATAA cDNA Sequence Encoding for PmSPS2

(SEQ ID NO: 11)

ATGTCGAAGATGGTGGAGGAGCATTGGGCAGCGCAGCGGGCGAGGGACCGGCGACAGTGCTGGCCATCGGCACTGCAAATCC

TCCCAATGTGTTGTACCAGGCAGATTATCCCGACTTCTACTTTAGGGTCACCAAGAGTGAGCACATGACCCAGCTAAAGGAGA

AGTTTAAACGTATATGTGATAAGTCAGCAATAAGAAAGCGCCACCTCCATCTAACCGAGGAGCTGCTGGAGAAGAACCCTAAC

ATATGTGCACACATGGCCCCCTCCCTCGACGCCCGGCAAGACATTGCGGTGGTGGAGGTCCCCAAGCTAGCCAAAGAAGCTGC

AACCAAGGCCATCAAGGAGTGGGGGCGACCCAAGTCCGACATCACCCACCTCATCTTCTGCACCACCTGCGGCGTGGACATGC

CCGGCGCCGACTACCAACTCACCACGCTCCTCGGCCTCCGCCCCACGGTCCGCCGCACCATGCTCTACCAACAGGGCTGCTTC

GCCGGCGGCACAGTCCTTCGCCATGCCAAGGACTTCGCCGAGAACAATAGGGGTGCTCGTGTCCTCGCCGTCTGCTCGGAGTT

CACCGTCATGAACTTCAGCGGACCGTCGGAGGCCCACTTAGACAGCATGGTCGGTATGGCGCTGTTCGGTGATGGCGCCTCGG

CTGTCATCGTCGGCGCCGATCCTGACTTTGCCATTGAACGACCGCTCTTTCAACTGGTTTCTACAACACAAACTATTGTCCCG

GACTCGGACGGAGCCATCAAGTGCCATCTCAAGGAGGTGGGCCTAACCCTGCATCTCGTTAAGAATGTACCAGATCTCATATC

AAATAACATGGACAAGATCCTCGAAGAGGCATTTGCACCATTGGGCATCAGAGATTGGAACTCAATCTTTTGGACAGCTCATC

CAGGTGGAGCAGCCATACTCGACCAGTTGGAGGCCAAGCTCGGTCTGAACAAGGAGAAGCTCAAGACTACAAGAACAGTTCTG

-continued

AGGGAGTATGGAAACATGTCCAGCGCCTGTGTTTGTTTCGTCCTGGACGAGATGAGGAGAAGTAGCTTGGAGGAGGGGAAGAC

AACGTCCGGGGAAGGGTTGGAATGGGGAATTCTGCTAGGGTTTGGGCCTGGGTTGACAGTGGAGACAGTCGTCTTGCGTAGCG

TACCCATCTCGACAGCCAATTAA cDNA Sequence Encoding for PmCHS (SEQ ID NO: 12)

ATGTCGAAGACCGTAGAGGAGATTTGGGCGGCGCAGCGGGCGAGGGGACCAGCCACGGTGCTGGCCATCGGCACTGCTGCGCC

GGCCAATGTGGTGTACCAGGCCGATTATCCGGACTACTACTTTAGGATCACCAAGAGCGAGCACATGACAGAGCTCAAGGAGA

AGTTCCGACGAATGTGTGACAAGTCGATGATAACGAAGCGGCACATGCACTTGTCGGAGGAGCTGTTGAAAAACAACCCTGAC

ATCTGTGCCTACATGGCCCCTTCCCTCGACGCCCGCCAAGATATGGTCGTGGTGGAGGTACCCAAGCTCGGCAAGGAGGCGGC

CGCCAAGGCCATCAAGGAATGGGGCCGCCCAAAGTCGGCCATCACCCACCTCATCTTCTGCACCACCTCCGGCGTCGACATGC

CCGGCGCCGATTTCCAGCTCACCAAGCTACTCGGCCTCTGCCCCTCCGTTCGCCGCACCATGCTCTACCAGCAGGGCTGCTTC

GCCGGCGGTACGGTTCTCCGCCTTGCCAAGGACCTCGCCGAGAACAATGCGGGCGCGAGGGTCCTCGTCGTCTGCTCCGAGAT

CACCGCCGTCACCTTCCGCGGCCCCTCGGAGACTCACCTCGATAGCATGGTCGGCCAGGCCCTGTTCGGTGATGGTGCCTCTG

CCATCATCGTCGGTGCCGACCCCGACCCCGTCATAGAAAGGCCACTCTTTCAAATTGTATCTGCGGCTCAGACCATCCTTCCC

GACTCGGATGGGGCAATAGACGGCCATCTCCGAGAAGTGGGTCTAACCTTCCACCTCCTCAAGGACGTACCTGGGCTCATCTC

AAAGAACATCGAGAAGAGCCTAAAGGAGGCGTTTGCACCGCTGGGCATCGACGACTGGAACTCGATATTTTGGATTGTTCATC

CAGGCGGGCCGGCCATTCTAGACCAGGTGGAGGCGAAGCTGCGTCTGAAAGTGGAGAAGCTGAAGACAACGAGAACAGTTTTG

AGTGAGTACGGGAATATGTCGAGCGCTTGCGTGTTGTTCATACTTGACGAGATGAGGAGGAACAGCATGGAAGAAGGGAAGGC

GACGACCGGTGAAGGGTTACATTGGGGAGTTTTGTTTGGTTTTGGGCCGGGCTTGACAGTGGAGACGGTCGTCTTGCATAGTT

TGCCCATCGCCGAGGCCAACTAA cDNA Sequence Encoding for PmOMT4

(SEQ ID NO: 13)

ATGGAGCAAGCTGTGTTCAAAGACCAATCCCCAAGCAGGGATGATATTGATGAAGAGCTCTTTCAATCTGCTCTATATCTTAG

CACTGCGGTTGTCACCGTGCCGGCGGCAATCATGGCTGCAAATGACCTTGACGTGCTGCAGATAATTGCCAAAGCTGGCCCAG

GTGCTCACCTATCTCCGACAGAGATTGTCAGCCACCTTCCCACCCGTAACCCTAATGCCGCGGCGGCGCTTCACCGGATACTC

CGAGTACTAGCCAGCCACTCCATCCTTGAATGCTCGTCGAGATGCGAGGGCGAGGCAAAATATGGATTAAGGCCGGTGTGCAA

GTTCTTTCTCAATGATAAGGATGGTGTCTCCTTGAATGCCATGCCATCCTTCGTTCAAAGTAGAGTTTTTATAGATAGCTGGC

AATATATGAAAGATGCTGTTCTTGAGGGGGTAGTCCCCTTTGAGAAAGCCTATGGTATGCCTTTTTATCAGTTTCAAGCAGTG

AACACCAAATTCAAAGAAACCTTCGCCAAAGCCATGGCTGCTCACTCAACTTTGGTAGTAAAAAAGATGCTTGACACATACAA

TGGGTTTGAGGGACTCACTGAGTTGATGGATGTTGCTGGTGGAACCGGTTCCACCCTCAACCTCATTGTCTCCAAATACCCAC

AAATCAAAGGCACAAACTTTGATCTCAAACATGTCATTGAGGCCGCACCAAACTACCCTGGGGTGAAGCATTTGAGTGGGGAC

ATGTTTGATAGCATTCCAAGTGCAAAGAACATTATTATGAAGTGGATACTACATAATTGGAGCGACGAGCACTGTGTAAAACT

CCTCAAGAACTGCTACACTTCCTTACCAGAATTTGGGAAGTTGATTGTGGTTGATTCCATTGTGGGTGAGGATGTTGATGCTG

GTTTGACGACAACAAATGTCTTTGGATGCGACTTCACAATGCTAACTTTCTTCCCCAATGCAAAAGAGAGGACCCGTGAAGAA

TTCCAAGACCTGGCCAAAGCTAGTGGCTTCTCAACGTTCAAACCGATCTGCTGCGCCTATGGCGTGTGGGTTATGGAATTTCA

CAAATAA cDNA Sequence Encoding for PmOMT1

(SEQ ID NO: 14)

ATGAATGATCAAGAGTTGCATGGATACTCACAAAATGCTCAACCTCAGCTATGGAACCTCCTGTTGAGCTTCATAAATTCCAT

GTCCCTTAAGTGTGCAGTGGAGTTGGGCATCCCCGATATAATACATAGCCATGCCCAAACACCAATCAACATAACCGACCTTG

CTGCCTCCATACCCATTCCCCAAACAAAACAAGCCAATTCCGCCGACTCATGCGCCTCCTGGTTCACTCCAACGTCTTTTCC

GTCCATAAACGTGAGGATGGTGATGAGGGGTTCCTCCTAACTCCTATGTCCAGGATCCTTGTCACGTCGAACGACAATAATGG

AGGTAACTTGTCACCCTTTGTTTCCATGATGGTTGATCCGTCCCTGGTGTCTCCATGGCACTTCCTTGGTCAATGGCTCAAAG

-continued

GCAATGACACCCAAGGCACACCATTTCGCATGTGCCATGGTGAAGAAATGTGGGACTGGGCCAACAAGTACCCGGACTTCAAC

AAGAAGTTCAACATGGCGATGGTCTGTGACAGCCAGTATTTAATGAAAATTATTGTGAAGAAGTGCGCCACTGCCTTTGAAGG

CAAGAGGTCCCTGATTGACGTCGGTGGCGGGACTGGTGGCGCCGCACGGTCTATTGCCGAAGCATTTCCAGACATACAGGAGG

TGTCTGTATTGGATCTTCCTCATGTGGTTGCAGGTTTGCCCAATGACTCGAGGGTGAAGTTTGTTGGAGGAGACATGTTCCAC

ACCATCCCTCCCGCTGATGTTGTCTTATTGAAGGCGATTTTTCATGGTTGGAATGATGAGGAGTGCATCAAGATATTGAAGAA

CTGCAAGAAGGCAATTCCAAGCAAGGAAGAGGGAGGCAAGGTGATGATATTGGACATGGTGGTCAATTCCGCCCCGGGTGACC

ATATGATTACAGAAGATCAATATTTTATGGATTTGATGATGATAACCTACGCAAGAGGATTGGAGAGAGACGAGAATGAATGG

AAGAAGCTGTTTAAAGATGCAGGTTTCACATCGTACAAGATCACCCACGGGCTTGGAACGAGTTCGCTTATCGAGCTCTACCC

TTAG cDNA Sequence Encoding for PmMDB1
(SEQ ID NO: 15)
ATGGAGCAAGCTCAATGGGTCGACCCAACTCTGCTCCCTGCATTTGTGGGCATCATCTTCTTCTTCCTTGGCATGTTCTTTGG AAGGAGTTCTTTGGGAGCTGGGAAGGGTGCAGCGCCTAGAAGCACCAGTTCTACCGAGTGGCCAGACGGCCCTCCAAAGCTGC CCATCATCGGCAACCTGCACCAGCTCAACAAAGGCGGGGAGCTGGTCCACCACAACCTCGCCAAGCTCGCCCAGTCCTACGAC CGCGCCATGACCATCTGGGTCGGCAGCTGGGGCCCCATGATCGTCGTCAGCGACGCCGACCTTGCATGGGAGGTCCTCGTCAC CAAGTCGCCGGATTCGCCGGCCGGGTGCTCTCCAAGCTCTCGCACTTGTTCAACGCCAACTACAACACCGTCGTCGCCTACGA CGCCGGGCCGCAATGGCAGTCGCTCCGGCGAGGTCTGCAGCACGGGCCGCTCGGCCCCGCCCATGTTTCTGCGCAGGCTCGTT TCCACGAAGAAGACATGAAGCTCCTGGTGAGCGACATGATGAGAGCAGCACAGAAAGGTGGTAGCAATGGAGTGGTTGAACCT CTGGCCTATGTCCGGCGAGCCACTATCCGATTTCTGTCTCGTCTATGCTTTGGGGAGGCCTTCAACGACGAGGCGTTCGTGGA GGGGATGGACGAAGCAGTGGAGGAGACCATCGGAGCCACTGGCCATGCACGCATCCTCGACGCCTTCTACTTCACTCGCCACC TCCCTATCATCCGCCGCAGCTTCATAGATACCGTCAACGCCAAGAAGAAGATCGAGAGCCTTGTCCGGCCGTTGCTCTCCCGG CCGGCGCCACCGGGGTCTTACCTCCACTTCCTCCTTTCCACCGACGCGCCGGAGAATATGATCATCTTTCGAATATTCGAAGT CTACTTGCTGGGCGTGGACAGCACCGCCTCCACCACCACATGGGCTCTCGCCTTCCTCGTCTCCAACCAACAGGCGCAGGAGA AGCTCCACAATGAGCTCGCCCAGTACTGCGCCAGCCAGAACAATCAGATCATCAAAGCAGACGACGTCGGAAAGCTGTCGTAC CTGCTCGGGGTAGTGAAGGAGACGATGAGGATGAAGCCGATAGCGCCGCTGGCCGTCCCCCACAAGACGCTCAAGGAGACGAT GCTCGACGGAAAGAGGGTGGCGGCGGGAACGACGGTGGTAGTGAACCTCTATGCCGTCCACTACAACCCGAAGCTATGGCCGG AGCCGGAGCAGTTCCGCCCGGAGAGGTTCGTGGTCGGCGCCAGCGGCGGCAATGGTGGGGGGTCTTCCGAGTACATGCTGCAG TCGTACCTGCCCTTTGGAGGGGGGATGAGGTCCTGCGCAGGGATGGAGGTGGGAAAGTTGCAGGTGGCGATGGTCGTGGCCAA CCTTGTGATGGCATTTAAATGGTTGCCGGAGGAGGAGGGGAAGATGCCGGACCTGGCTGAAGACATGACCTTCGTGCTCATGA

TGAAGAAGCCATTGGCTGCCAAAATCGTTCCACGTGCATGA cDNA Sequence Encoding for PmRDCT10
(SEQ ID NO: 16)
ATGGAGACTGAGAGGAAGTCCAGGATCTGTGTCACCGGGGCAGGAGGCTTTGTAGCCTCTTGGGTCGTCAAGCTTTTCCTCTC CAAAGGTTATCTTGTCCATGGCACTGTCAGAGACCTCGGAGAAGAGAAGACTGCCCATTTGAGGAAGTTGGAGGGTGCGTACC ATAATCTGCAGCTGTTCAAGGCTGACTTGTTGGATTATGAGTCCTTGCTCGGGGCCATTACTGGCTGCGATGGAGTTCTCCAT GTTGCAACTCCTGTTCCTTCGAGTAAAACTGCTTATTCCGGAACTGAGTTGGTCAAGACTGCTGTGAATGGAACTCTGAATGT GCTCAGGGCATGTACAGAGGCAAAAGTGAAAAAGGTCATCTATGTTTCATCTACTGCCGCTGTTTTGGTGAATCCTAATTTAC CCAAGGATAAAATCCCGGACGAAGATTGTTGGACAGACGAAGAGTACTGCAGGACAACTCCGTTCTTCCTGAATTGGTATTGC ATCGCCAAAACAGCAGCCGAAAAGAATGCCTTGGAATATGGAGATAAAGAAGGGATCAACGTTATATCTATTTGCCCTTCATA CATCTTTGGACCTATGCTTCAACCGACAATTAATTCAAGCAACTTGGAATTGTTGAGGCTAATGAAAGGAGATGACGAAAGCA TAGAAAACAAATTTCTGCTGATGGTGGATGTGCGAGATGTTGCTGAAGCAATTTTACTATTATATGAGAAGCAAGAAACATCA GGGAGATACATTTCTTCGCCGCATGGTATGCGACAAAGCAACTTGGTTGAGAAGCTGGAGAGCCTGCAGCCGGGCTACAATTA

```
TCATAAGAACTTTGTGGATATTAAACCTAGTTGGACAATGATCAGCTCAGAAAAGCTCAAGAAACTTGGTTGGAAACCTAGAC

CACTTGAGGACACTATTTCTGAAACAGTGCTGTGTTTTGAAGAGCATGGTTTGCTGGAAAATGAATAG
```

REFERENCES

1. Y. N. Singh, Kava: an overview. *Journal of Ethnopharmacology* 37, 13-45 (1992).
2. V. Lebot, J. Levesque, The Origin And Distribution Of Kava (*Piper methysticum* Forst. F., Piperaceae): A Phytochemical Approach. *Allertonia* 5, 223-281 (1989).
3. J. Sarris, E. LaPorte, I. Schweitzer, Kava: A Comprehensive Review of Efficacy, Safety, and Psychopharmacology. *Australian & New Zealand Journal of Psychiatry* 45, 27-35 (2011).
4. K. Shinomiya et al, Effects of kava-kava extract on the sleep-wake cycle in sleep-disturbed rats. *Psychopharmacology* 180, 564-569 (2005).
5. S. Caimey, P. Maruff, A. R. Clough, The neurobehavioural effects of kava. *Australian and New Zealand Journal of Psychiatry* 36, 807-662 (2002).
6. H. C. Chua et al., Kavain, the Major Constituent of the Anxiolytic Kava Extract, Potentiates $GABA_A$ Receptors: Functional Characteristics and Molecular Mechanism. *PLoS One* 11, e0157700 (2016).
7. A. Ligresti, R. Villano, M. Allara, I. Ujvary, V. Di Marzo, Kavalactones and the endocannabinoid system: The plant-derived yangonin is a novel CB1 receptor ligand. *Pharmacological Research* 66, 163-169 (2012).
8. L. D. Dinh et al., Interaction of various *Piper methysticum* cultivars with CNS receptors in vitro. *Planta Med* 67, 306-311 (2001).
9. N. Abu, The flavokawains: uprising medicinal chalcones. *Cancer Cell Int* 12, (2013).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method for producing a compound of Formula (V), the method comprising:
reducing a compound of Formula (IV), or a salt thereof, with a reducing agent using an enzyme having an amino acid sequence that is at least 90% sequence identical to the amino acid sequence of PmRDCT10 polypeptide of SEQ ID NO: 8 to produce a compound of Formula (V), or a salt thereof:

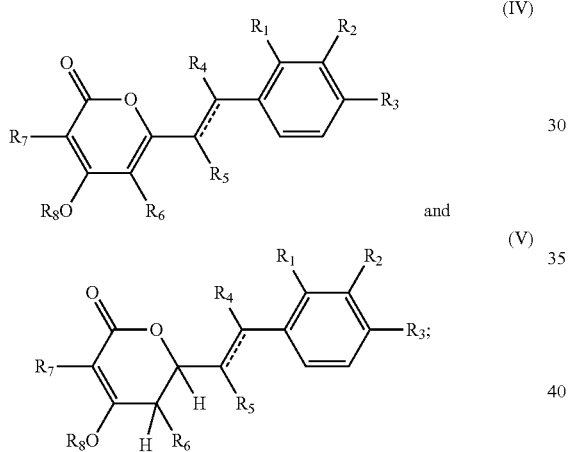

wherein:
= is a single bond or a double bond;
each of $R_1$, $R_2$, $R_3$, $R_6$, and $R_7$ independently is hydrogen, substituted or unsubstituted, cyclic or acyclic aliphatic, or —ORx, or $R_1$ and $R_2$ are combined to form a ring, or $R_2$ and $R_3$ are combined to form a ring, wherein Rx is hydrogen or substituted or unsubstituted, cyclic or acyclic aliphatic;
each of $R_4$ and $R_5$ independently is hydrogen or substituted or unsubstituted, cyclic or acyclic aliphatic; and $R_8$ is hydrogen or substituted or unsubstituted, cyclic or acyclic aliphatic.

2. The method of claim 1, wherein = is a single bond.

3. The method of claim 1, wherein = is a double bond.

4. The method of claim 1, wherein each of $R_1$, $R_2$, and $R_3$ is independently selected from the group consisting of hydrogen, —OH, and —OCH$_3$.

5. The method of claim 1, wherein $R_4$ and $R_5$ are hydrogen.

6. The method of claim 1, wherein $R_1$, $R_2$, and $R_3$ are hydrogen.

7. The method of claim 6, wherein each of $R_6$ and $R_7$ is independently selected from the group consisting of hydrogen, OH, and —OCH$_3$.

8. The method of claim 7, wherein each of $R_6$ and $R_7$ is hydrogen.

9. The method of claim 8, wherein $R_8$ is —CH$_3$ or hydrogen.

10. The method of claim 1, wherein the reducing agent is NADPH or NADH.

11. The method of claim 1, wherein the enzyme is a purified enzyme or a partially purified enzyme, and the method is performed in vitro.

12. The method of claim 1, wherein the enzyme is in a cell, and the enzyme is heterologous to the cell containing the enzyme, and the method is performed in the cell.

13. The method of claim 1, wherein the method further comprises, prior to the step of reducing a compound of Formula (IV), or a salt thereof, with a reducing agent, the steps of:
condensing a compound of Formula (I), or a salt thereof, with coenzyme A (CoA) using an enzyme having an amino acid sequence that is at least 90% sequence identical to the amino acid sequence of Pm4CL1 polypeptide of SEQ ID NO: 1 (Pm4CL1) to produce a compound of Formula (II), or a salt thereof:

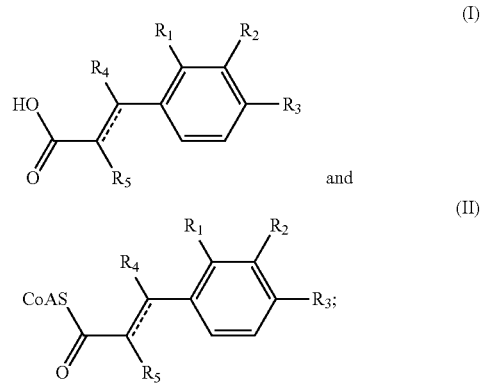

reacting a compound of Formula (II), or a salt thereof, with malonyl-CoA using an enzyme having an amino acid sequence that is at least 90% sequence identical to the amino acid sequence of PmSPS1 polypeptide of SEQ ID NO: 2 or an enzyme that is at least 90% sequence identical to the amino acid sequence of PmSPS2 polypeptide of SEQ ID NO: 3 to produce a compound of Formula (III), or a salt thereof:

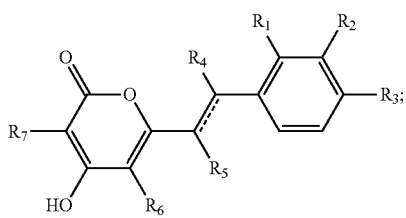
(III)

and reacting the compound of Formula (III), or a salt thereof, with an enzyme having an amino acid sequence that is at least 90% sequence identical to the amino acid sequence of PmOMT1 polypeptide of SEQ ID NO: 6 to produce a compound of Formula (IV), or a salt thereof, in which $R_8$ is hydrogen.

14. The method of claim 13, wherein the method is performed in a cell comprising an enzyme having an amino acid sequence that is at least 90% sequence identical to the amino acid sequence of Pm4CL1 polypeptide of SEQ ID NO: 1;

an enzyme having an amino acid sequence that is at least 90% sequence identical to the amino acid sequence of PmSPS1 polypeptide of SEQ ID NO: 2 (PmSPS1) or an enzyme having an amino acid sequence that is at least 90% sequence identical to the amino acid sequence of PmSPS2 polypeptide of SEQ ID NO: 3;

an enzyme that is at least 90% sequence identical to the amino acid sequence of PmOMT1 polypeptide of SEQ ID NO: 6; and an enzyme that is at least 90% sequence identical to the amino acid sequence of PmRDCT10 polypeptide of SEQ ID NO: 8;

wherein the enzymes are heterologous to the cell.

15. The method of claim 14, wherein the cell is a yeast cell or a bacterial cell.

16. The method of claim 15, wherein the method produces a compound of Formula (V), or a salt thereof, in which ═ is a single bond or double bond;

each of $R_1$, $R_2$, $R_3$, $R_4$, $R_5$, $R_6$, and $R_7$, is hydrogen; and $R_8$ is hydrogen or —$CH_3$.

* * * * *

UNITED STATES PATENT AND TRADEMARK OFFICE
CERTIFICATE OF CORRECTION

PATENT NO. : 11,739,354 B2  
APPLICATION NO. : 17/190872  
DATED : August 29, 2023  
INVENTOR(S) : Tomás Pluskal et al.

Page 1 of 1

It is certified that error appears in the above-identified patent and that said Letters Patent is hereby corrected as shown below:

In the Claims

In Claim 12, at Column 134, Lines 26-27, the text: "wherein the enzyme is in a cell, and the enzyme" is replaced with: --wherein the enzyme is in a cell, the enzyme--.

In Claim 13, at Column 134, Lines 37-38, the text: "polypeptide of SEQ ID NO: 1 (Pm4CL1) to produce a" is replaced with: --polypeptide of SEQ ID NO: 1 to produce a--.

Signed and Sealed this  
First Day of April, 2025

Coke Morgan Stewart  
*Acting Director of the United States Patent and Trademark Office*